US009850534B2

United States Patent
Davis et al.

(10) Patent No.: US 9,850,534 B2
(45) Date of Patent: *Dec. 26, 2017

(54) METHODS FOR CREATING BILAYERS FOR USE WITH NANOPORE SENSORS

(71) Applicant: GENIA TECHNOLOGIES, INC., Mountain View, CA (US)

(72) Inventors: Randall Davis, Pleasanton, CA (US); Roger Chen, Saratoga, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/376,836

(22) PCT Filed: Feb. 15, 2013

(86) PCT No.: PCT/US2013/026514
§ 371 (c)(1),
(2) Date: Aug. 5, 2014

(87) PCT Pub. No.: WO2013/123450
PCT Pub. Date: Aug. 22, 2013

(65) Prior Publication Data
US 2015/0337366 A1 Nov. 26, 2015

Related U.S. Application Data

(60) Provisional application No. 61/599,871, filed on Feb. 16, 2012, provisional application No. 61/600,398, filed on Feb. 17, 2012.

(51) Int. Cl.
*C12Q 1/68* (2006.01)
*C12N 15/11* (2006.01)
(Continued)

(52) U.S. Cl.
CPC .......... *C12Q 1/6869* (2013.01); *C12N 15/111* (2013.01); *G01N 33/48721* (2013.01);
(Continued)

(58) Field of Classification Search
CPC .......... C11Q 1/68; G01N 27/32; G01N 33/48; G01N 33/54; G01N 15/06; G01N 27/00; C12Q 1/68; A61K 9/1272; A61K 49/0084
See application file for complete search history.

(56) References Cited

U.S. PATENT DOCUMENTS 5,756,355 A * 5/1998 Lang .................. G01N 33/5432
204/194
8,124,191 B2 * 2/2012 Ervin ..................... H01B 1/122
427/299
(Continued)

FOREIGN PATENT DOCUMENTS

EP 2219032 A1 8/2010
JP 2006-312141 A 11/2006
(Continued)

OTHER PUBLICATIONS

J. Nivala, D. B. Marks and M. Akeson, "Unfoldase-mediated protein translocation through an a-hemolysin nanopore," Nature Biotechnology, 2013, DOI: 10.1038/nbt.2503.

*Primary Examiner* — Narayan Bhat
(74) *Attorney, Agent, or Firm* — FisherBroyles, LLP; Victoria L. Boyd

(57) ABSTRACT

The present disclosure provides biochips and methods for making biochips. A biochip can comprise a nanopore in a membrane (e.g., lipid bilayer) adjacent or in proximity to an electrode. Methods are described for forming the membrane and inserting the nanopore into the membrane. The biochips and methods can be used for nucleic acid (e.g., DNA) sequencing. The present disclosure also describes methods for detecting, sorting, and binning molecules (e.g., proteins) using biochips.

44 Claims, 43 Drawing Sheets

(51) Int. Cl.
*G01N 33/487* (2006.01)
*G01N 33/543* (2006.01)

(52) U.S. Cl.
CPC ...... *G01N 33/5432* (2013.01); *C12N 2310/11* (2013.01); *C12N 2310/16* (2013.01); *C12N 2310/3517* (2013.01); *C12N 2320/10* (2013.01); *C12N 2320/32* (2013.01)

(56) References Cited

U.S. PATENT DOCUMENTS

| | | | |
|---|---|---|---|
| 2009/0167288 A1* | 7/2009 | Reid | G01N 33/48721 324/72 |
| 2010/0196203 A1 | 8/2010 | Sanghera et al. | |
| 2010/0320094 A1 | 12/2010 | White et al. | |
| 2011/0193249 A1 | 8/2011 | Chen et al. | |
| 2012/0255862 A1* | 10/2012 | Dunnam | B82Y 5/00 204/543 |

FOREIGN PATENT DOCUMENTS

| | | |
|---|---|---|
| KR | 10-2010-0031498 A | 3/2010 |
| WO | 2007047498 A2 | 4/2007 |
| WO | 200907734 A2 | 6/2009 |
| WO | 2011097028 A1 | 8/2011 |
| WO | 2012009578 A2 | 1/2012 |

* cited by examiner

701 Flowing in a lipid solution comprising at least one type of lipid through each of the flow channels

702 Depositing the lipids on the surface of electrodes

703 Smoothing and thinning the deposited lipids with a follow-on bubble in each of the flow channels

704 Filling each of the flow channels with a buffer solution, the buffer solution being electrically conductive

705 Measuring currents through the electrodes to determine if a lipid bilayer is formed over each of the electrodes

706 If the lipid bilayers are formed on the electrodes, applying a stimulus through at least one of the electrodes to insert pores in the bilayers

*FIG. 7*

- A  Electrodes
- B1 Hydrophobic/Lipophillic Surface
- B2 Semiconductor substrate
- C  Solvent/Lipid
- D  Lipid Bilayer
- E  Pore
- F  Conductive solution (salt soluition)
- G  Peltier device for electronic temperature control

METHODS FOR CREATING BILAYERS FOR USE WITH NANOPORE SENSORS

CROSS-REFERENCE

This application claims the benefit of U.S. Provisional Patent Application No. 61/599,871, filed Feb. 16, 2012, and U.S. Provisional Patent Application No. 61/600,398, filed Feb. 17, 2012, each of which is incorporated herein by reference in its entirety.

BACKGROUND

Nucleic acid sequencing is a process that may be used to provide sequence information for a nucleic acid sample. Such sequence information may be helpful in diagnosing and/or treating a subject. For example, the nucleic acid sequence of a subject may be used to identify, diagnose and potentially develop treatments for genetic diseases. As another example, research into pathogens may lead to treatment for contagious diseases. Molecular detection (e.g., of proteins) may also be helpful in diagnosing and/or treating a subject.

There are methods available which may be used to sequence a nucleic acid and/or detect molecules. Such methods, however, are expensive and may not provide sequence information within a time period and at an accuracy that may be necessary to diagnose and/or treat a subject.

SUMMARY

Nanopores can be used to sequence polymers including nucleic acid molecules and/or detect molecules such as proteins. Examples of polymers include deoxyribonucleic acid (DNA) and ribonucleic acid (RNA). Recognized herein is the need for improved methods for nucleic acid molecule identification, nucleic acid sequencing and molecular detection. Described herein are methods for forming a lipid bilayer (also "bi-layer" herein) and inserting a nanopore into the bilayer in proximity to a sensor.

In some instances, the polymer (e.g., nucleic acid) is passed through the nanopore and various subunits of the polymer (e.g., adenine (A), cytosine (C), guanine (G), thymine (T) and/or uracil (U) bases of the nucleic acid) may affect the current flowing through the nanopore. As described herein, the various subunits can be identified by measuring the current at a plurality of voltages applied across the nanopore and/or membrane.

In an aspect, a method for forming a membrane (e.g., lipid bilayer) for use in a nanopore sensor comprises (a) directing a buffer solution in flow channel comprising an electrode having a material layer thereon, wherein the buffer solution is electrically conductive, and wherein the material layer comprises one or more constituents of the membrane (e.g., lipids); (b) bringing the buffer solution in contact with the material layer; (c) measuring a current through the electrode to determine if at least a portion of the material layer has formed a membrane (e.g., lipid bilayer) over all or a portion of the electrode; and (d) based on the determination of (c), applying a stimulus to the electrode to induce the at least the portion of the material layer to form the membrane adjacent to the electrode.

In some embodiments, one or more voltages are applied to the electrodes in (c).

In some embodiments, the voltage is high enough to break the bilayer over the electrode.

In some embodiments, the stimulus is applied simultaneously to all the electrodes.

In some embodiments, the stimulus comprises at least one of a liquid flow over the surface of the electrode, a sequential flow of one or more different liquids over the surface of the electrode, the flow of one or more bubbles over the surface of the electrode, an electrical pulse, sonication pulse, pressure pulse, or sound pulse.

In some embodiments, the material layer comprising one or more porin proteins comprises one or more surfactants at a concentration less than the critical micelle concentration of the surfactant.

In some embodiments, the flow channel comprises a plurality of electrodes.

In some embodiments, the material layer comprises a lipid. In some cases, the material layer comprises at least two, three, four, five, or ten types of lipids.

In some embodiments, the material layer comprises a pore protein.

In some embodiments, the pore protein is *mycobacterium smegmatis* porin A (MspA), alpha-hemolysin, any protein having at least 70% homology to at least one of *smegmatis* porin A (MspA) or alpha-hemolysin, or any combination thereof.

In some embodiments, the method further comprises, after (d), applying an electrical stimulus through the electrode to facilitate the insertion of the pore protein in the membrane (e.g., lipid bilayer).

In some embodiments, the membrane and the pore protein together exhibit a resistance of about 1 G$\Omega$ or less.

In some embodiments, the membrane without a pore protein exhibits a resistance greater than about 1 G$\Omega$.

In some embodiments, a pressure of the buffer solution is selected such that the material layer forms the membrane without the stimulus.

In some embodiments, the method further comprises, prior to (a), generating the material layer adjacent to the electrode.

In some embodiments, the generating operation comprises: directing a lipid solution comprising one or more lipids through the flow channel; and depositing the material layer on the electrode.

In some embodiments, the lipid solution comprises an organic solvent.

In some embodiments, the organic solvent comprises decane.

In some embodiments, the buffer solution comprises an ionic solution.

In some embodiments, the ionic solution comprises a chloride anion.

In some embodiments, the ionic solution comprises sodium acetate.

In some embodiments, the method further comprises, after (a): directing a bubble through the flow channel; and bringing the bubble in contact with the material layer to smooth and/or thin the material layer.

In some embodiments, the bubble is a vapor bubble.

In some embodiments, the method further comprises: flowing a pore protein solution adjacent to the material layer to deposit a pore protein in the material layer; and thinning the material layer with ionic solution and/or another bubble in the flow channel.

In some embodiments, lipids can be selected from the group consisting of diphytanoylphosphatidylcholine (DPhPC), palmitoyl-oleoyl-phosphatidyl-choline (POPC), dioleoyl-phosphatidyl-methylester (DOPME), dipalmitoyl-phosphatidylcholine (DPPC), phosphatidylcholine, phosphatidylethanolamine, phosphatidylserine, phosphatidic acid, phosphatidylinositol, phosphatidylglycerol and sphingomyelin.

In some embodiments, a surface of the electrode that is exposed to the flow channel is hydrophilic.

In some embodiments, the electrode is disposed adjacent to one or more hydrophobic surfaces of the flow channel.

In some embodiments, the one or more hydrophobic surfaces are silanized.

In some embodiments, the flow channel is formed in a chip.

In some embodiments, the electrode is formed in a surface of the flow channel.

In some embodiments, the flow channel is sealed.

In some embodiments, the one or more flow channels comprise a plurality of flow channels.

In some embodiments, the plurality of flow channels are fluidically separated from one another with the aid of guide rails along the plurality of flow channels.

In some embodiments, the electrode is an individually addressable electrode.

In an aspect, a method for forming a membrane (e.g., lipid bilayer) for use in a nanopore sensing device comprises: (a) providing a chip comprising a plurality of electrodes and material layers adjacent to the plurality of electrodes, wherein each of the material layers comprises one or more constituents (e.g., lipids) of the membranes; (b) contacting the material layers with a buffer solution, wherein the buffer solution is electrically conductive; (c) applying a stimulus to at least a subset of the plurality of electrodes to induce the material layers to form membranes adjacent to the plurality of the electrodes; and (d) repeating steps (b) and (c), as needed, until at least about 20% of the plurality of electrodes deactivate at a voltage pulse between about −100 millivolts (mV) and −1000 mV applied to the plurality of electrodes.

In some embodiments, the plurality of electrodes are each individually addressable.

In some embodiments, steps (b) and (c) are repeated as needed until at least about 60% of the plurality of electrodes deactivate at the applied voltage pulse.

In some embodiments, the applied voltage pulse is between about −400 mV and −700 mV.

In some embodiments, the stimulus comprises at least one of a liquid flow over the surface of the electrode, a sequential flow of one or more different liquids over the surface of the electrode, the flow of one or more bubbles over the surface of the electrode, an electrical pulse, sonication pulse, pressure pulse, or sound pulse.

In some embodiments, each of the material layers comprises a pore protein.

In some embodiments, the pore protein is *mycobacterium smegmatis* porin A (MspA), alpha-hemolysin, any protein having at least 70% homology to at least one of *smegmatis* porin A (MspA) or alpha-hemolysin, or any combination thereof.

In some embodiments, the method further comprises, after (c), applying an electrical stimulus through at least a subset of the electrodes to facilitate the insertion of the pore protein in each of the lipid bilayers.

In some embodiments, the method further comprises: contacting the plurality of electrodes with a lipid solution to form the material layers, wherein the lipid solution comprises the lipid.

In some embodiments, the lipid solution comprises an organic solvent.

In some embodiments, the organic solvent comprises decane.

In some embodiments, the buffer solution comprises an ionic solution.

In some embodiments, the ionic solution comprises a chloride anion.

In some embodiments, the ionic solution comprises sodium acetate.

In some embodiments, the method further comprises, between steps (a) and (b), directing a bubble adjacent to each of the material layers.

In some embodiments, the electrodes are sealed in one or more flow channels of the chip.

In an aspect, a method for detecting a target molecule comprises: (a) providing a chip comprising a nanopore in a membrane that is disposed adjacent or in proximity to a sensing electrode; (b) directing a nucleic acid molecule through the nanopore, wherein the nucleic acid molecule is associated with a reporter molecule, wherein the nucleic acid molecule comprises an address region and a probe region, wherein the reporter molecule is associated with the nucleic acid molecule at the probe region, and wherein the reporter molecule is coupled to a target molecule; (c) sequencing the address region while the nucleic acid molecule is directed through the nanopore to determine a nucleic acid sequence of the address region; and (d) identifying, with the aid of a computer processor, the target molecule based upon a nucleic acid sequence of the address region determined in (c).

In some embodiments, in (b), the probe molecule in (b) is held in the pore by the binding of a reporter molecule to the probe region of the nucleic acid molecule.

In some embodiments, up to three bases of the nucleic acid molecule are identified when the rate of progression of the nucleic acid molecule through the nanopore is reduced.

In some embodiments, up to five bases of the nucleic acid molecule are identified when the rate of progression of the nucleic acid molecule through the nanopore is reduced.

In some embodiments, the rate of progression of the nucleic acid molecule through the nanopore is reduced upon the interaction of the reporter molecule with the nanopore.

In some embodiments, in (b), a rate of progression of the nucleic acid molecule through the nanopore is stopped or stalled.

In some embodiments, the method further comprises, prior to (d), determining whether a rate of progression of the nucleic molecule through the nanopore has been reduced.

In some embodiments, in (d), the target molecule is identified if it is determined that the rate of progression of the nucleic acid molecule through the nanopore has been reduced.

In some embodiments, in (d), the target molecule is identified based upon a correlation between (i) a nucleic acid sequence of the address region and an association and (ii) a rate of progression of the nucleic acid molecule through the nanopore.

In some embodiments, the nanopore is individually addressable.

In some embodiments, the nucleic acid molecule is single-stranded.

In some embodiments, the method further comprises trapping the nucleic acid molecule in the nanopore.

In some embodiments, the nucleic acid molecule is trapped in the nanopore with the aid of bulky structures formed at one or more end portions of the nucleic acid molecule.

In some embodiments, the nucleic acid molecule is trapped in the nanopore with the aid of bulky structures affixed to one or more end portions of the nucleic acid molecule.

In some embodiments, the method further comprises reversing a direction of flow of the nucleic acid molecule through the nanopore.

In some embodiments, the method further comprises re-sequencing at least a portion of the address region upon reversing the direction of flow of the nucleic acid molecule.

In some embodiments, the reporter molecule comprises an antibody or aptamer at an end portion of the reporter molecule, and wherein the antibody or aptamer is associated with the target molecule.

In some embodiments, address region and probe region have known nucleic acid sequences.

In some embodiments, the reporter molecule comprises a nucleic acid sequence that is complimentary to a nucleic acid sequence of the probe region.

In some embodiments, the nucleic acid molecule is associated with the reporter molecule prior to being directed through the.

In some embodiments, prior to (b), the nucleic acid molecule is threaded through the nanopore, and wherein, in (b), the reporter molecule is associated with the nucleic acid molecule that has been threaded through the nanopore.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein) of which:

In FIG. 1A, the nanopore is disposed upon the electrode; in FIG. 1B, the nanopore is inserted in a membrane over a well; and in FIG. 1C; the nanopore is disposed over a protruding electrode;

FIG. 2A shows the detection of a molecule; FIG. 2B shows the detection of portions of a polymer molecule; FIG. 2C shows the detection of tag molecules for nucleic acid sequencing; and FIG. 2D shows the detection of the tag while the nucleotide is being incorporated;

FIG. 7 shows an example of a method for forming a lipid layer over the electrodes on one or more flow channels of the sensor chip;

DETAILED DESCRIPTION

Figure 1A:
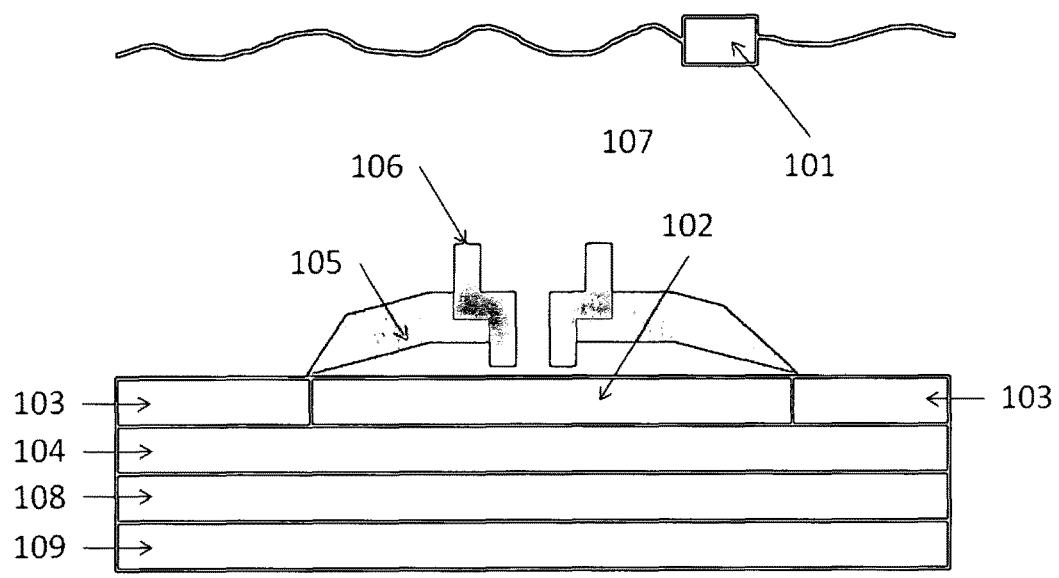
FIGS. 1A, 1B and 1C show examples of nanopore detectors.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The term "nanopore," as used herein, generally refers to a pore, channel or passage formed or otherwise provided in a membrane. A membrane may be an organic membrane, such as a lipid bilayer, or a synthetic membrane, such as a membrane formed of a polymeric material. The membrane may be a polymeric material. The nanopore may be disposed adjacent or in proximity to a sensing circuit or an electrode coupled to a sensing circuit, such as, for example, a complementary metal-oxide semiconductor (CMOS) or field effect transistor (FET) circuit. In some examples, a nanopore has a characteristic width or diameter on the order of 0.1 nanometers (nm) to about 1000 nm. Some nanopores are proteins. Alpha hemolysin is an example of a protein nanopore.

The term "polymerase," as used herein, generally refers to any enzyme or other molecular catalyst that is capable of catalyzing a polymerization reaction. Examples of polymerases include, without limitation, a nucleic acid polymerase or a ligase. A polymerase can be a polymerization enzyme.

The term "nucleic acid," as used herein, generally refers to a molecule comprising one or more nucleic acid subunits. A nucleic acid may include one or more subunits selected from adenosine (A), cytosine (C), guanine (G), thymine (T) and uracil (U), or variants thereof. A nucleotide can include A, C, G, T or U, or variants thereof. A nucleotide can include any subunit that can be incorporated into a growing nucleic acid strand. Such subunit can be an A, C, G, T, or U, or any other subunit that is specific to one or more complementary A, C, G, T or U, or complementary to a purine (i.e., A or G, or variant thereof) or a pyrimidine (i.e., C, T or U, or variant thereof). A subunit can enable individual nucleic acid bases or groups of bases (e.g., AA, TA, AT, GC, CG, CT, TC, GT, TG, AC, CA, or uracil-counterparts thereof) to be resolved. In some examples, a nucleic acid is deoxyribonucleic acid (DNA) or ribonucleic acid (RNA), or variants or derivatives thereof. A nucleic acid may be single-stranded or double stranded.

The term "polynucleotide" or "oligonucleotide," as used herein, generally refers to a polymer or oligomer comprising one or more nucleotides. A polynucleotide or oligonucleotide may comprise a DNA polynucleotide or oligonucleotide, a RNA polynucleotide or oligonucleotide, or one or more sections of DNA polynucleotide or oligonucleotide and/or RNA polynucleotide or oligonucleotide.

As generally used herein, a "nucleotide" or "base" can be a primary nucleotide or a nucleotide analog. A primary nucleotide is deoxyadenosine mono-phosphate (dAMP), deoxycytidine mono-phosphate (dCMP), deoxyguanosine mono-phosphate (dGMP), deoxythymidine mono-phosphate (dTMP), adenosine mono-phosphate (AMP), cytidine mono-phosphate (CMP), guanosine mono-phosphate (GMP) or uridine mono-phosphate (UMP). A nucleotide analog is an analog or mimic of a primary nucleotide having modification on the primary nucleobase (A, C, G, T and U), the deoxyribose/ribose structure, the phosphate group of the primary nucleotide, or any combination thereof. For example, a nucleotide analog can have a modified base, either naturally existing or man-made. Examples of modified bases include, without limitation, methylated nucleobases, modified purine bases (e.g. hypoxanthine, xanthine, 7-methylguanine, isodG), modified pyrimidine bases (e.g. 5,6-dihydrouracil and 5-methylcytosine, isodC), universal bases (e.g. 3-nitropyrrole and 5-nitroindole), non-binding base mimics (e.g. 4-methylbezimidazole and 2,4-diflurotoluene or benzene), and no base (abasic nucleotide where the nucleotide analog does not have a base). Examples of nucleotide analogs having modified deoxyribose (e.g. dideoxynucleosides such as dideoxyguanosine, dideoxyadenosine, dideoxythymidine, and dideoxycytidine) and/or phosphate structure (together referred to as the backbone structure) includes, without limitation, glycol nucleotides, morpholinos, and locked nucleotides.

The term "test polymer," as used herein, generally refers to a polymer molecule that passes through or adjacent to a nanopore for detection purposes. The test polymer may comprise multiple building blocks that have similar chemical structures. Examples of test polymers include, without limitation, test polynucleotides, test peptides/proteins, and test carbohydrates. A test polynucleotide can be a single-stranded test polynucleotide (i.e., ss test polynucleotide) or a double-stranded test polynucleotide (i.e., ds test polynucleotide). Examples of building blocks include, without limitation, nucleotides, amino acids, and monosaccharides.

The term "sample polynucleotide," as used herein, generally refers to a nucleic acid molecule which can comprise a polynucleotide of interest, such as, for example, a single-stranded ("ss") sample polynucleotide (ss sample polynucleotide) or a double-stranded ("ds") sample polynucleotide (i.e., ds sample polynucleotide, such as, e.g. ds sample DNA, ds sample RNA, and ds sample DNA-RNA hybrid). A sample polynucleotide can be a natural polynucleotide obtained from a biological sample or a synthetic polynucleotide. The synthetic polynucleotide may be a polynucleotide obtained by modification of a natural polynucleotide, such as pre-processed polynucleotide intended for use in polynucleotide identification and/or sequencing. Examples of such pre-processings include, without limitation, enrichment of the sample polynucleotide for desired fragments, paired-end processing, mated pair read processing, epigenetic pre-processing including bisulfide treatment, focused fragment analysis via PCR, PCR fragment sequencing, and short polynucleotide fragment analysis.

The term "test polynucleotide," as used herein, generally refers to a polynucleotide molecule that passes through or adjacent to a nanopore for detection purposes. A test polynucleotide can be a single-stranded test polynucleotide (i.e., ss test polynucleotide) and a double-stranded test polynucleotide (i.e., ds test polynucleotide, such as, e.g. ds test DNA, ds test RNA, and ds test DNA-RNA hybrid). A ss test polynucleotide, as used herein, comprises a section of ss polynucleotide that is to be bound by a speed bump in a method described herein. A ss test polynucleotide may further comprise a sample polynucleotide and other functional moieties (e.g., pre-bulky structure, identifiers and isolation tags).

The term "pre-bulky structure", as used herein, generally refers to a molecular structure in a polynucleotide molecule which can form a bulky structure under certain conditions (e.g., at certain temperature, presence/absence of certain compound(s)). Examples of pre-bulky structures include oligonucleotide structures. A pre-bulky structure can be a ss polynucleotide or a ds polynucleotide.

The term "bulky structure", as used herein, generally refers to a structure (e.g., nucleotide) formed from a pre-bulky structure in a ss test polynucleotide molecule. The bulky structure can slow or stall the test polynucleotide molecule in a nanopore at a working condition until the working condition is changed to another condition wherein the bulky structure is converted to the pre-bulky structure or other structures that may stall the test polynucleotide molecule. Examples of bulky structures include, without limitation, 2-D and 3-D structures such as polynucleotide duplex structures (RNA duplex, DNA duplex or RNA-DNA hybrid), polynucleotide hairpin structures, multi-hairpin structures and multi-arm structures. In another embodiment the pre-bulky structure forms a bulky structure via interaction with a ligand specific to the pre-bulky structure. Examples of such pre-bulky structure/ligand pair include, without limitation, biotin/streptavidin, antigen/antibody, and carbohydrate/antibody.

In an embodiment, the bulky structure is formed from an oligonucleotide pre-bulky structure, e.g., an oligonucleotide structure formed from a pre-bulky structure in a ss test polynucleotide molecule. Examples of polynucleotide or oligonucleotide bulky structures include, without limitation, hairpin nucleic acid strands, hybridized antisense nucleic acid strands, multiple arms and three dimensional DNA or RNA molecules that are self-hybridized. In another embodiment, the bulky structure is formed via interactions of a pre-bulky structure/ligand pair as described herein.

The term "duplex," as used herein, generally refers to a duplex structure, section, region or segment. A duplex can include an RNA duplex, DNA duplex or a DNA-RNA duplex structure, section, region or segment.

The term "speed bump," as used herein, generally refers to a molecule, such as an oligonucleotide, that forms a complex with a binding segment of a test polynucleotide molecule. In an example, when a test polynucleotide molecule travels through or adjacent to a nanopore under an applied electric potential, the complex formed between a speed bump and the binding segment slows or stalls the test polynucleotide molecule in or adjacent to the nanopore for a dwelling time long enough for the nanopore detector to obtain a signal from the test polynucleotide molecule, which signal can provide structure or sequence information for the test polynucleotide molecule. After the dwelling time, the complex dissociates and the test polynucleotide molecule moves forward through the nanopore.

The term "known speed bump," as used herein, generally refers to a speed bump that specifically binds to a known sequence in a ss test polynucleotide. Because the binding segment on the ss test polynucleotide (the known sequence) is known, the speed bump structure can also be known (e.g. complementary to the known sequence on the ss test polynucleotide).

The term "random speed bump pool," as used herein, generally refers to a collection of speed bumps that can bind to all or substantially all sections of a test polynucleotide molecule or a fragment thereof. An example of random speed bump pool comprises oligonucleotides having universal nucleobases which base-pair with all primary nucleobases (A, T, C, G and U). Another example of random speed bump pool comprises oligonucleotides of a given length having all possible combinations of primary nucleobases. Another example of random speed bump pool comprises oligonucleotides of a given length having every possible combination of primary nucleobases and universal nucleobases. Another example of random speed bump pool comprises speed bumps having universal nucleobases at designated positions and all combinations of primary nucleobases at the other positions. Another example of random speed bumps is a combination of ss speed bumps, which form duplex sections with ss test polynucleotide, and the duplex sections have about the same melting temperatures. These ss speed bumps may have the same or different lengths, and/or the same or different nucleotides.

The term "stopper," as used herein, generally refers to a structure that can form a stopper-test polynucleotide complex with the test polynucleotide and stop the flow of the stopper-test polynucleotide complex before the constriction area of the nanopore for the dwelling time. The stopper can be part of the test polynucleotide, or a separate structure (e.g. a speed bump described herein, and an antisense strand of the test polynucleotide formed in the presence of a nucleotide polymerase), or an enzyme that can bind to the test polynucleotide and, in some cases, move the test polynucleotide through the nanopore.

The term "identifier," as used herein, generally refers to a known sequence or structure in a test polynucleotide that can be detected or identified by the method described herein. Examples of identifiers include, without limitation, direction identifiers, reference signal identifiers, sample source identifiers, and sample identifiers. The identifiers may comprise one or more nucleotides or structures that provide distinctive electrical signals that are identifiable. Examples of such nucleotides and structures include, without limitation, isodG, isodC, methylated nucleotides, locked nucleic acids, universal nucleotides, and abasic nucleotides. In some embodiments, an abasic nucleotide provides a stronger signal than a primary nucleotide. Thus, the electrical signal detected by a nanopore for a sequence comprising both abasic nucleotides and primary nucleotides may provide a signal more intense than the electrical signal obtained from primary nucleotide only sequences. For example, a 4 to 5 base sequence comprising about 25% abasic nucleotides may provide a signal more than twice as strong as a 4 to 5 base sequence comprising only primary nucleotides. The more abasic nucleotides the sequence have, the stronger electrical signal the sequence. Thus, identifiers may provide electrical signals of a desired intensity (e.g., about twice, about 3, 4, 5, 6, 7, 8, 9, or about 10 times stronger than that of primary oligonucleotides having the same length) by changing the amount of abasic nucleotides in the identifier sequences.

Figure 17:
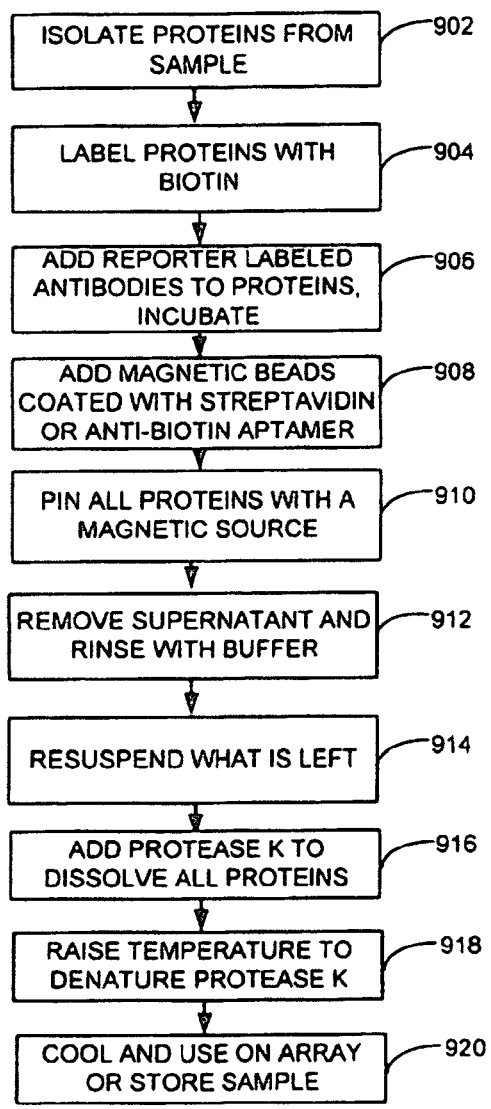
FIG. 17 is a process flow for detecting, identifying, counting, binning, and/or collecting target protein molecules using nanopore trapped probe molecule.

The term "direction identifier," as used herein, generally refers to a known sequence positioned at least 0, 1, 2, 3, 4, 5, 6, 7, 8, 9, 10, 11, 12, 13, 14, 15, 16, 17, 18, 19, 20, or 50 bases from a bulky structure formed from a pre-bulky structure (the shaded section in the ss test polynucleotide molecule as depicted in FIG. 17). In some examples, when a bulky structure is formed, it can stop a ss test polynucleotide molecule from flowing through a nanopore within which the ss test polynucleotide molecule is incorporated. In an example, when the bulky structure is stalled, slowed or stopped inside or adjacent to the nanopore, a set of electrical signals may be obtained, which can provide sequence information of the sequence that is in front of the bulky structure and the first base pair of the bulky structure, in the flow direction of the ss test polynucleotide molecule. When the sequence is known, such electrical signals can, without limitation: (1) verify that the pre-bulky structure has properly formed into the bulky structure such that the bulky structure stops the ss test polynucleotide molecule from flowing through the nanopore; (2) indicate that the ss test polynucleotide molecule has reached one end of the single strand section of the ss test polynucleotide, and/or (3) serve as a reference or calibration read to base line other electrical signals obtained in the same nanopore. In some embodiments, the direction identifier comprises one or more nucleotides or structures that provide distinctive electrical signals that are readily identified. Examples of such nucleotides and structures include, without limitation, isodG, isodC and abasic nucleotides.

The term "reference signal identifier," as used herein, generally refers to a known sequence in a test polynucleotide, which when detected or identified by the methods described herein, can serve as a reference or calibration read to base line other electrical signals obtained in the same nanopore.

The term "sample source identifier," as used herein, generally refers to a known sequence in a test polynucleotide, which when detected or identified by the methods described herein, can be used to identify the source of the sample polynucleotide.

The term "sample identifier," as used herein, generally refers to a known sequence in a test polynucleotide, which when detected or identified by the methods described herein, can be used to identify the individual sample polynucleotide.

The term "linker identifier," as used herein, generally refers to a known sequence in a test polynucleotide, which when detected or identified by the methods described herein, can be used to indicate the transition between the sample polynucleotide section and the antisense polynucleotide section. In an example, when the linker identifier is detected or identified, the sample/antisense polynucleotide section has passed through the nanopore.

"Probe source identifier", as used herein, is a known sequence in a probe polynucleotide, when detected or identified by the method described herein, is used to identify the source that the probe polynucleotide is from.

"Probe identifier", as used herein, is a known sequence in a probe polynucleotide, when detected or identified by the method described herein, is used to identify the individual sample polynucleotide.

The "Binding Site for Reporter Molecule" section binds to a reporter molecule as described herein. In some embodiments, the reporter molecule comprises DNA, RNA or any combinations thereof.

"Reporter identifier", as used herein, is a known sequence in a probe polynucleotide, when detected or identified by the method described herein, is used to indicate the binding of reporter molecule to the probe polynucleotide.

Nanopore Detection

Provided herein are systems and methods for identifying a molecule or portion thereof with a nanopore. A method for identifying a species, such as a molecule or portion thereof, with a nanopore can comprise providing a biochip (also "chip" herein) comprising at least one nanopore in a membrane that is disposed adjacent or in proximity to an electrode. The electrode can be adapted to detect a current passing through the nanopore. The method can further include inserting a molecule or portion thereof into the nanopore and varying a voltage applied across the nanopore and/or across the membrane. In some cases, the method includes measuring the current at a plurality of voltages to identify the molecule or portion thereof. In some embodiments, the current at a plurality of voltages comprises an electronic signature and further comprises comparing the electronic signature to a plurality of reference electronic signatures to identify the molecule or portion thereof.

The nanopore may be formed or otherwise embedded in a membrane disposed adjacent to a sensing electrode of a sensing circuit, such as an integrated circuit. The integrated circuit may be an application specific integrated circuit (ASIC). In some examples, the integrated circuit is a field effect transistor or a complementary metal-oxide semiconductor (CMOS). The sensing circuit may be situated in a chip or other device having the nanopore, or off of the chip or device, such as in an off-chip configuration. The semiconductor can be any semiconductor, including, without limitation, Group IV (e.g., silicon) and Group III-V semiconductors (e.g., gallium arsenide).

FIG. 1 shows an example of a nanopore detector (or sensor) having temperature control, as may be prepared according to methods described in U.S. Patent Application Publication No. 2011/0193570, which is entirely incorporated herein by reference. With reference to FIG. 1A, the nanopore detector comprises a top electrode 101 in contact with a conductive solution (e.g., salt solution) 107. A bottom conductive electrode 102 is near, adjacent, or in proximity to a nanopore 106, which is inserted in a membrane 105. In some instances, the bottom conductive electrode 102 is embedded in a semiconductor 103 in which is embedded electrical circuitry in a semiconductor substrate 104. A surface of the semiconductor 103 may be treated to be hydrophobic. A sample being detected goes through the pore in the nanopore 106. The semiconductor chip sensor is placed in package 208 and this, in turn, is in the vicinity of a temperature control element 109. The temperature control element 109 may be a thermoelectric heating and/or cooling device (e.g., Peltier device). In some instances, the bilayer spans and covers the electrode 202.

Multiple nanopore detectors may form a nanopore array. A nanopore array can include one or more nanopore detectors. In some cases, a nanopore array includes at least 1, 2, 3, 4, 5, 6, 7, 8, 9, 10, 100, 1000, 10000, or 100,000 nanopore detectors. An individual nanopore detector can include one or more nanopores adjacent to a sensing electrode (e.g., bottom conductive electrode 102). In some cases, an individual nanopore detector includes at least 1, 2, 3, 4, 5, 6, 7, 8, 9, 10, or 100 nanopores adjacent to a sensing electrode.

Figure 1B:
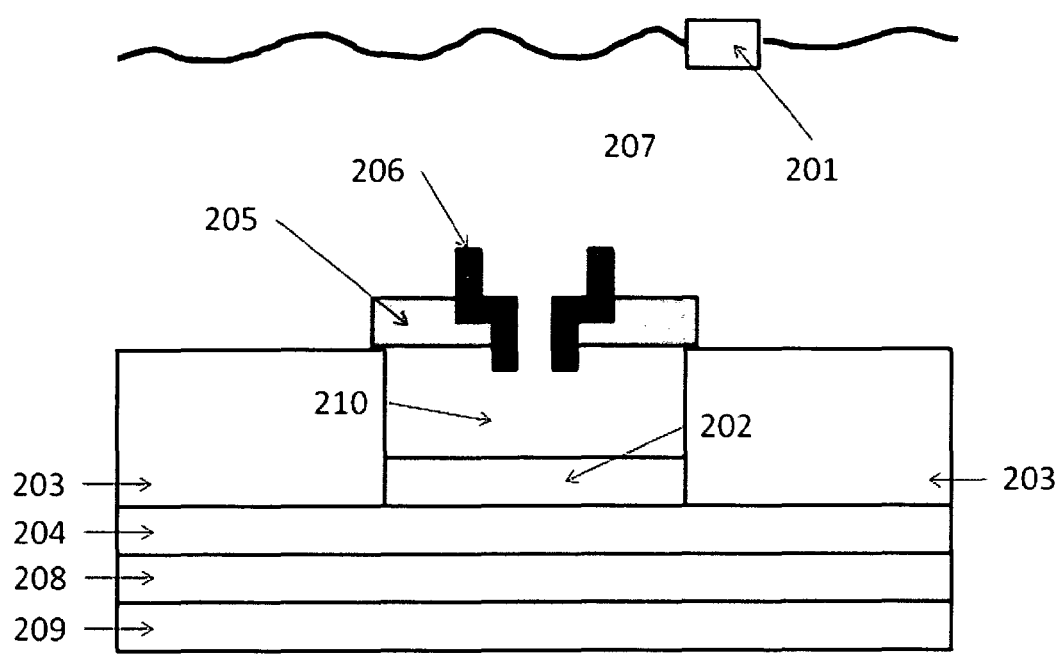
Figure 1C:
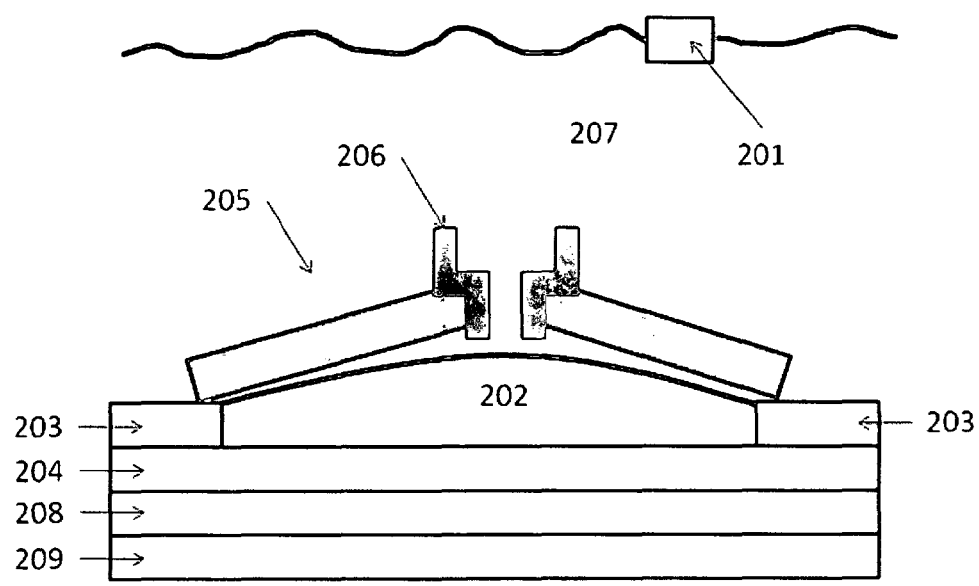

With reference to FIG. 1B, where like numerals represent like elements, the membrane 105 can be disposed over a well 110, where the sensor 102 forms part of the surface of the well. FIG. 1C shows an example in which the electrode 102 protrudes from the treated semiconductor surface 103.

In some examples, the membrane 105 forms on the bottom conductive electrode 102 and not on the semiconductor 103. The membrane 105 in such a case may form coupling interactions with the bottom conductive electrode 102. In some cases, however, the membrane 105 forms on the bottom conductive electrode 102 and the semiconductor 103. As an alternative, the membrane 105 can form on the semiconductor 103 and not on the bottom conductive electrode 102, but may extend over the bottom conductive electrode 102.

Many different types of molecules or portions thereof can be detected by the methods and/or devices described herein. FIG. 2 shows some examples of molecules that can be detected and methods for sequencing polymers including nucleic acids. In some cases, the molecule 201 passes through the nanopore 202 from the cis side 203 (away from the electrode) to the trans side 204 (toward to the electrode) of the membrane 205.

Figure 2A:
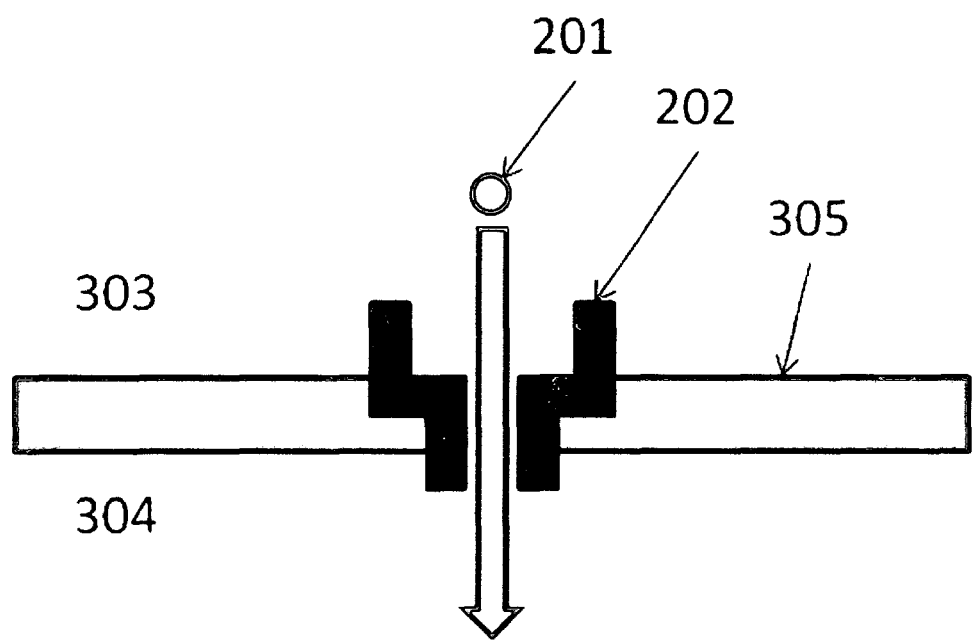
FIGS. 2A, 2B, 2C and 2D show examples of molecules that can be detected with nanopores.
Figure 2B:
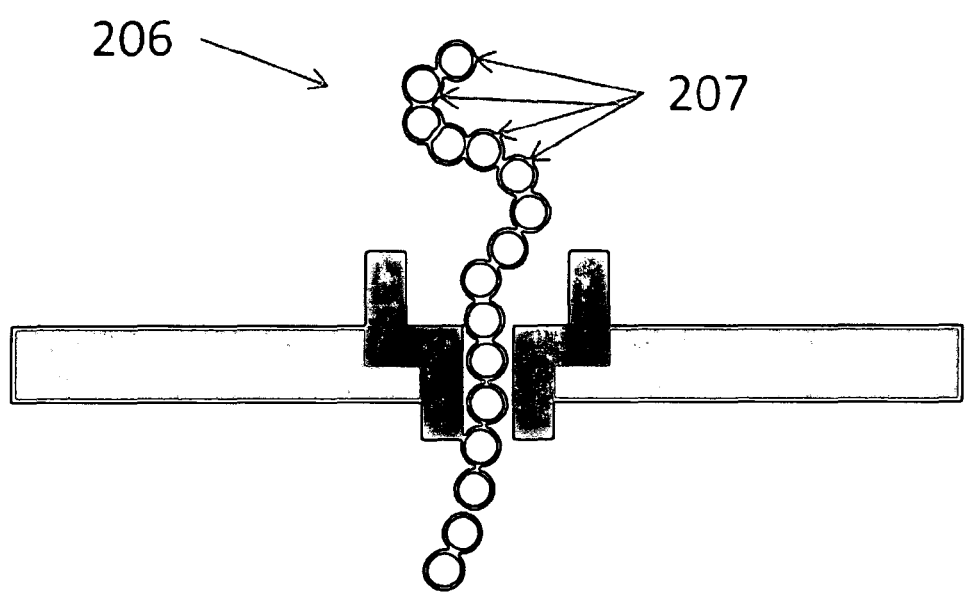

As seen in FIG. 2B, the molecule can be a polymer molecule 206 and portions of the polymer molecule 207 can be identified as the polymer molecule passes through the nanopore. The polymer molecule can be a biological molecule such as a nucleic acid or a protein. In some embodiments, the polymer molecule is a nucleic acid and the portions of the polymer molecule are nucleic acids or groups of nucleic acids (e.g., 2, 3, 4, 5, 6, 7, or 8 nucleic acids). In some embodiments, the polymer molecule is a polypeptide and the portions of the polypeptide are amino acids or groups of nucleic acids (e.g., 2, 3, 4, 5, 6, 7, or 8 amino acids).

In some cases, as a nucleic acid or tag flows through or adjacent to the nanopore, the sensing circuit detects an electrical signal associated with the nucleic acid or tag. The nucleic acid may be a subunit of a larger strand. The tag may be a byproduct of a nucleotide incorporation event or other interaction between a tagged nucleic acid and the nanopore or a species adjacent to the nanopore, such as an enzyme that cleaves a tag from a nucleic acid. The tag may remain attached to the nucleotide. A detected signal may be collected and stored in a memory location, and later used to construct a sequence of the nucleic acid. The collected signal may be processed to account for any abnormalities in the detected signal, such as errors.

Figure 2C:
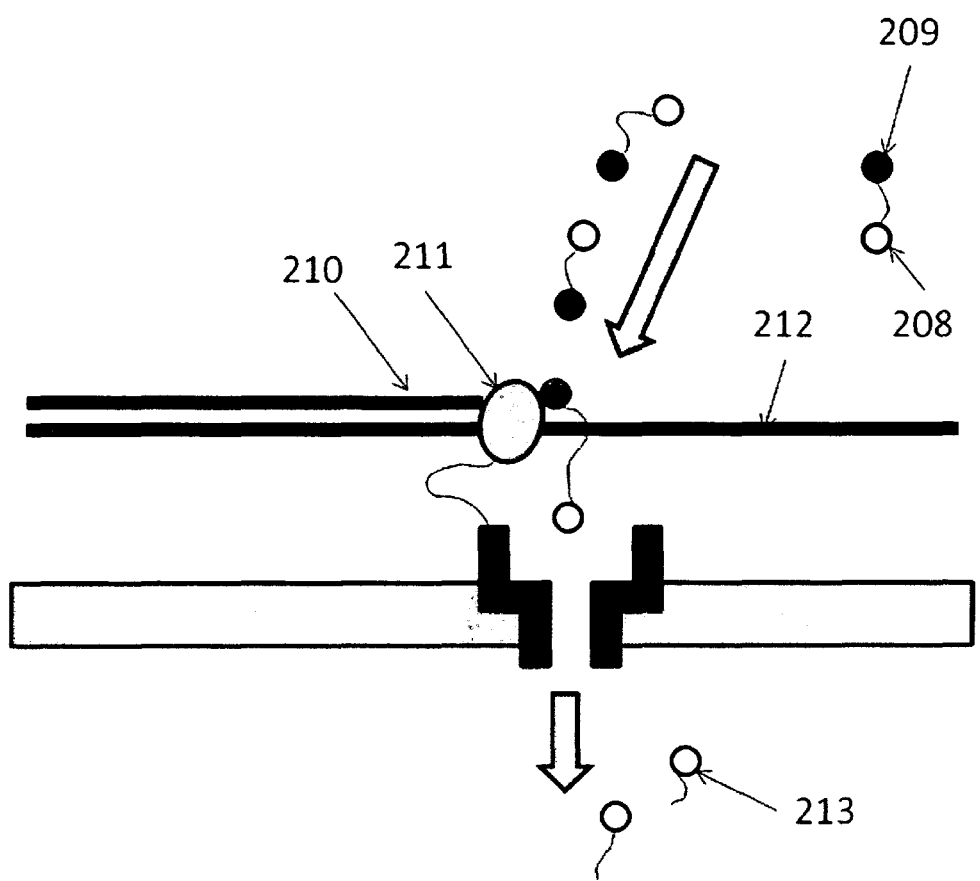
Figure 2D:
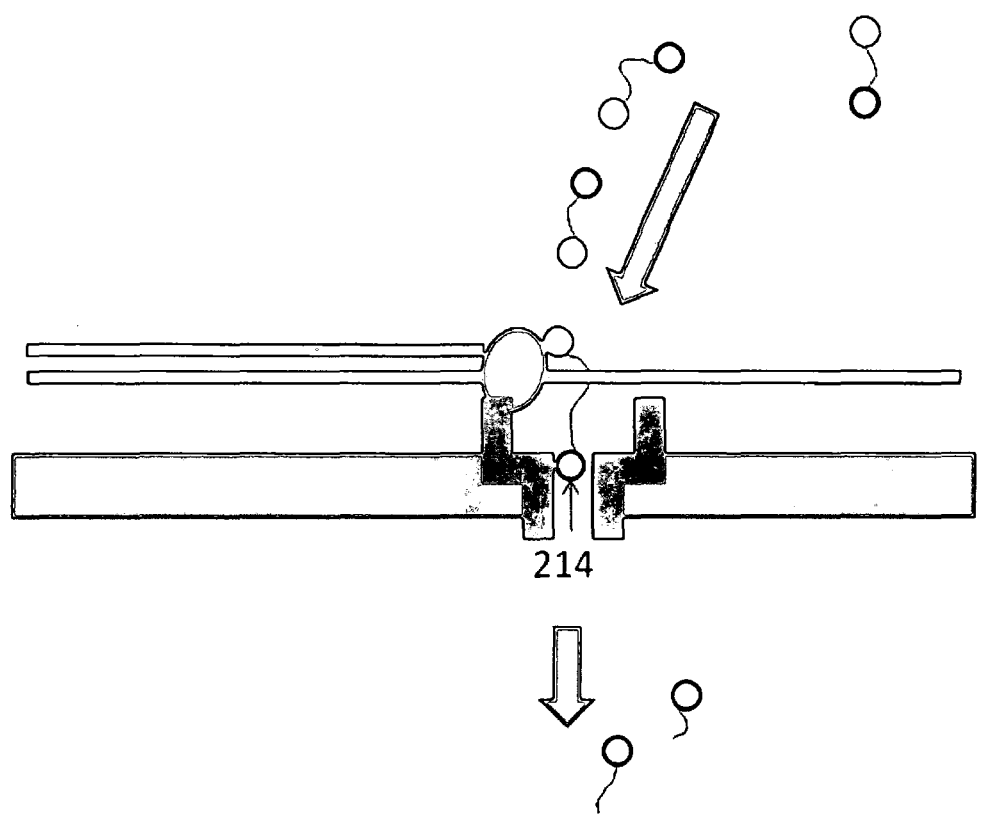

As seen in FIG. 2C, in some embodiments, the molecule 208 (e.g., a "tag molecule") is bound to a nucleotide 209. The molecule can be identified while the nucleotide is being incorporated into a growing nucleic acid chain 210 (e.g., by a polymerase 211). The nucleotide can be incorporated according to base pair matching with a template nucleic acid 212. If different tags are bound to each of the different nucleotides (e.g., A, C, T and G), the sequence of the template nucleic acid can be determined by detecting the tag molecules with the nanopore (e.g., without the template nucleic acid passing through the nanopore). In some embodiments, the molecule is released 213 from the nucleotide upon incorporation of the nucleotide into a growing nucleic acid chain. As shown in FIG. 2D, the molecule can be detected while the nucleotide is being incorporated into the growing strand and/or before being released from the nucleotide 214. In some cases, the address region of the probe or reporter region is sequenced using tags.

Device Setup

Figure 3:
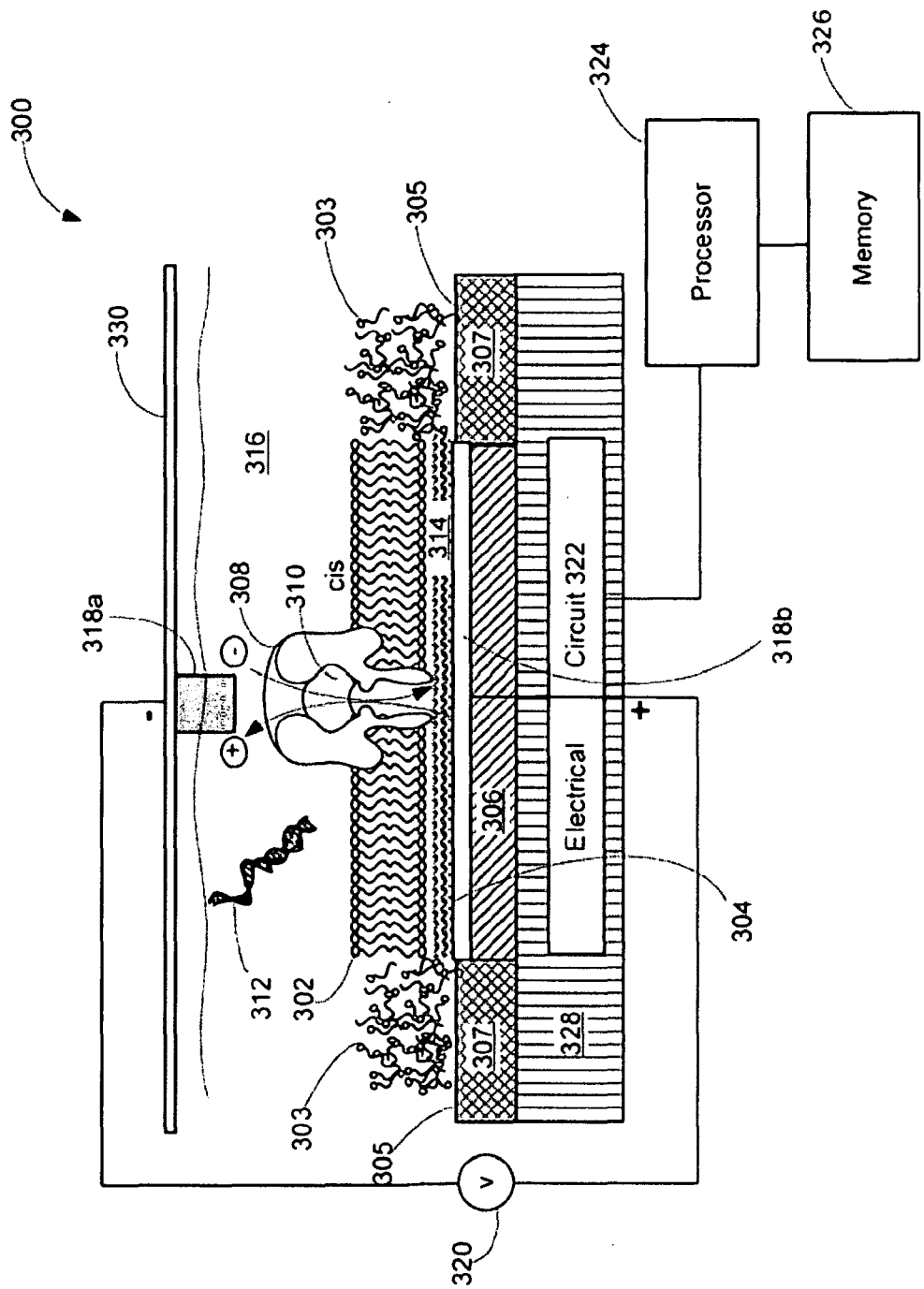
FIG. 3 shows an example of a chip set-up comprising a nanopore and not a well.

FIG. 3 schematically illustrates a nanopore device 300 (or sensor) that may be used to detect a molecule (and/or sequence a nucleic acid) as described herein. The nanopore containing lipid bilayer may be characterized by a resistance and capacitance. The nanopore device 300 includes a lipid bilayer 302 formed on a lipid bilayer compatible surface 304 of a conductive solid substrate 306, where the lipid bilayer compatible surface 304 may be isolated by lipid bilayer incompatible surfaces 305 and the conductive solid substrate 306 may be electrically isolated by insulating materials 307, and where the lipid bilayer 302 may be surrounded by amorphous lipid 303 formed on the lipid bilayer incompatible surface 305. The lipid bilayer 302 may be embedded with a single nanopore structure 308 having a nanopore 310 large enough for passing of the molecules being detected and/or small ions (e.g., $Na^+$, $K^+$, $Ca^{2+}$, $Cl^-$) between the two sides of the lipid bilayer 302. A layer of water molecules 314 may be adsorbed on the lipid bilayer compatible surface 304 and sandwiched between the lipid bilayer 302 and the lipid bilayer compatible surface 304. The aqueous film 314 adsorbed on the hydrophilic lipid bilayer compatible surface 304 may promote the ordering of lipid molecules and facilitate the formation of lipid bilayer on the lipid bilayer compatible surface 304. A sample chamber 316 containing a solution of the molecule to be detected (e.g., nucleic acid molecule, in some cases with tagged nucleotides or other components as needed) 312 may be provided over the lipid bilayer 302. The solution may be an aqueous solution containing electrolytes and buffered to an optimum ion concentration and maintained at an optimum pH to keep the nanopore 310 open. The device includes a pair of electrodes 318 (including a negative node 318a and a positive node 318b) coupled to a variable voltage source 320 for providing electrical stimulus (e.g., voltage bias) across the lipid bilayer and for sensing electrical characteristics of the lipid bilayer (e.g., resistance, capacitance, and ionic current flow). The surface of the positive electrode 318b is or forms a part of the lipid bilayer compatible surface 304. The conductive solid substrate 306 may be coupled to or forms a part of one of the electrodes 318. The device 300 may also include an electrical circuit 322 for controlling electrical stimulation and for processing the signal detected. In some embodiments, the (e.g., variable) voltage source 320 is included as a part of the electrical circuit 322. The electrical circuitry 322 may include amplifier, integrator, noise filter, feedback control logic, and/or various other components. The electrical circuitry 322 may be integrated electrical circuitry integrated within a silicon substrate 328 and may be further coupled to a computer processor 324 coupled to a memory 326.

The lipid bilayer compatible surface 304 may be formed from various materials that are suitable for ion transduction and gas formation to facilitate lipid bilayer formation. In some embodiments, conductive or semi-conductive hydrophilic materials may be used because they may allow better detection of a change in the lipid bilayer electrical characteristics. Example materials include Ag—AgCl, Au, Pt, or doped silicon or other semiconductor materials. In some cases, the electrode is not a sacrificial electrode.

The lipid bilayer incompatible surface 305 may be formed from various materials that are not suitable for lipid bilayer formation and they are typically hydrophobic. In some embodiments, non-conductive hydrophobic materials are preferred, since it electrically insulates the lipid bilayer regions in addition to separate the lipid bilayer regions from each other. Example lipid bilayer incompatible materials include for example silicon nitride (e.g., $Si_3N_4$) and Teflon, silicon oxide (e.g., $SiO_2$) silanized with hydrophobic molecules.

In an example, the nanopore device 300 of FIG. 3 is a alpha hemolysin (aHL) nanopore device having a single alpha hemolysin (aHL) protein 308 embedded in a diphytanoylphosphatidylcholine (DPhPC) lipid bilayer 302 formed over a lipid bilayer compatible silver (Ag) surface 304 coated on an aluminum material 306. The lipid bilayer compatible Ag surface 304 is isolated by lipid bilayer incompatible silicon nitride surfaces 305, and the aluminum material 306 is electrically insulated by silicon nitride materials 307. The aluminum 306 is coupled to electrical circuitry 322 that is integrated in a silicon substrate 328. A silver-silver chloride electrode placed on-chip or extending down from a cover plate 328 contacts an aqueous solution containing (e.g., nucleic acid) molecules.

The aHL nanopore is an assembly of seven individual peptides. The entrance or vestibule of the aHL nanopore is approximately 26 Angstroms in diameter, which is wide enough to accommodate a portion of a dsDNA molecule. From the vestibule, the aHL nanopore first widens and then narrows to a barrel having a diameter of approximately 15 Angstroms, which is wide enough to allow a single ssDNA molecule (or smaller tag molecules) to pass through but not wide enough to allow a dsDNA molecule (or larger tag molecules) to pass through.

In addition to DPhPC, the lipid bilayer of the nanopore device may be assembled from various other suitable amphiphilic materials, selected based on various considerations, such as the type of nanopore used, the type of molecule being characterized, and various physical, chemical and/or electrical characteristics of the lipid bilayer formed, such as stability and permeability, resistance, and capacitance of the lipid bilayer formed. Example amphiphilic materials include various phospholipids such as palmitoyl-oleoyl-phosphatidyl-choline (POPC) and dioleoyl-phosphatidyl-methylester (DOPME), diphytanoylphosphatidylcholine (DPhPC) dipalmitoylphosphatidylcholine (DPPC), phosphatidylcholine, phosphatidylethanolamine, phosphatidylserine, phosphatidic acid, phosphatidylinositol, phosphatidylglycerol, and sphingomyelin.

In addition to the aHL nanopore shown above, the nanopore may be of various other types of nanopores. Examples include γ-hemolysin, leukocidin, melittin, *mycobacterium smegmatis* porin A (MspA) and various other naturally occurring, modified natural, and synthetic nanopores. A suitable nanopore may be selected based on various characteristics of the analyte molecule such as the size of the analyte molecule in relation to the pore size of the nanopore. For example, the aHL nanopore that has a restrictive pore size of approximately 15 Angstroms.

Current Measurement

In some cases, current may be measured at different applied voltages. In order to accomplish this, a desired potential may be applied to the electrode, and the applied potential may be subsequently maintained throughout the measurement. In an implementation, an opamp integrator topology may be used for this purpose as described herein. The integrator maintains the voltage potential at the electrode by means of capacitive feedback. The integrator circuit may provide outstanding linearity, cell-to-cell matching, and offset characteristics. The opamp integrator typically requires a large size in order to achieve the required performance. A more compact integrator topology is described herein.

In some cases, a voltage potential "Vliquid" may be applied to the chamber which provides a common electrical potential (e.g., 350 mV) for all of the cells on the chip. The integrator circuit may initialize the electrode (which is electrically the top plate of the integrating capacitor) to a potential greater than the common liquid potential. For example, biasing at 450 mV may give a positive 100 mV potential between electrode and liquid. This positive voltage potential may cause a current to flow from the electrode to the liquid chamber contact. In this instance, the carriers are: (a) K+ ions which flow through the pore from the electrode (trans) side of the bi-layer to the liquid reservoir (cis) side of the bi-layer and (b) chlorine (Cl−) ions on the trans side which reacts with the silver electrode according to the following electro-chemical reaction: Ag+Cl−→AgCl+e−.

In some cases, K+ flows out of the enclosed cell (from trans to cis side of bi-layer) while Cl− is converted to silver chloride. The electrode side of the bilayer may become desalinated as a result of the current flow. In some cases, a silver/silver-chloride liquid spongy material or matrix may serve as a reservoir to supply Cl− ions in the reverse reaction which occur at the electrical chamber contact to complete the circuit.

In some cases, electrons ultimately flow onto the top side of the integrating capacitor which creates the electrical current that is measured. The electrochemical reaction converts silver to silver chloride and current will continue to flow only as long as there is available silver to be converted. The limited supply of silver leads to a current dependent electrode life in some cases. In some embodiments, electrode materials that are not depleted (e.g., platinum) are used.

Figure 4:
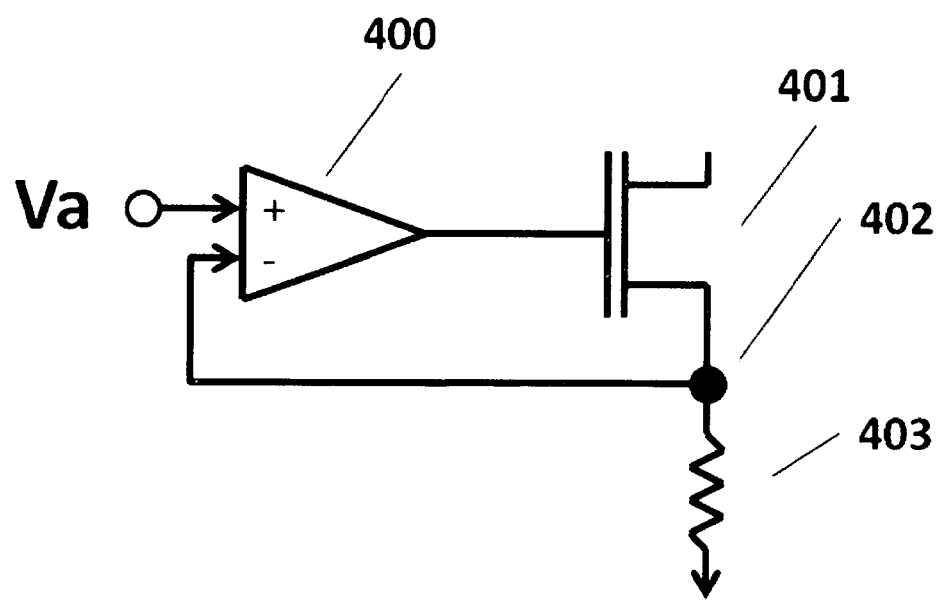
FIG. 4 shows an example of an ultra compact measurement circuit.

An example of cell circuitry is shown in FIG. 4. An applied voltage Va is applied to an opamp 1200 ahead of a MOSFET current conveyor gate 401. Also shown here are an electrode 402 and the resistance of the nucleic acid and/or tag detected by the device 403.

An applied voltage Va can drive the current conveyor gate 401. The resulting voltage on the electrode sis then Va-Vt where Vt is the threshold voltage of the MOSFET. In some instances, this results in limited control of the actual voltage applied to the electrode as a MOSFET threshold voltage can vary considerably over process, voltage, temperature, and even between devices within a chip. This Vt variation can be greater at low current levels where sub-threshold leakage effects can come into play. Therefore, in order to provide better control of the applied voltage, an opamp can be used in a follower feedback configuration with the current conveyor device. This ensures that the voltage applied to the electrode is Va, independent of variation of the MOSFET threshold voltage.

Arrays of Nanopores

Figure 5:
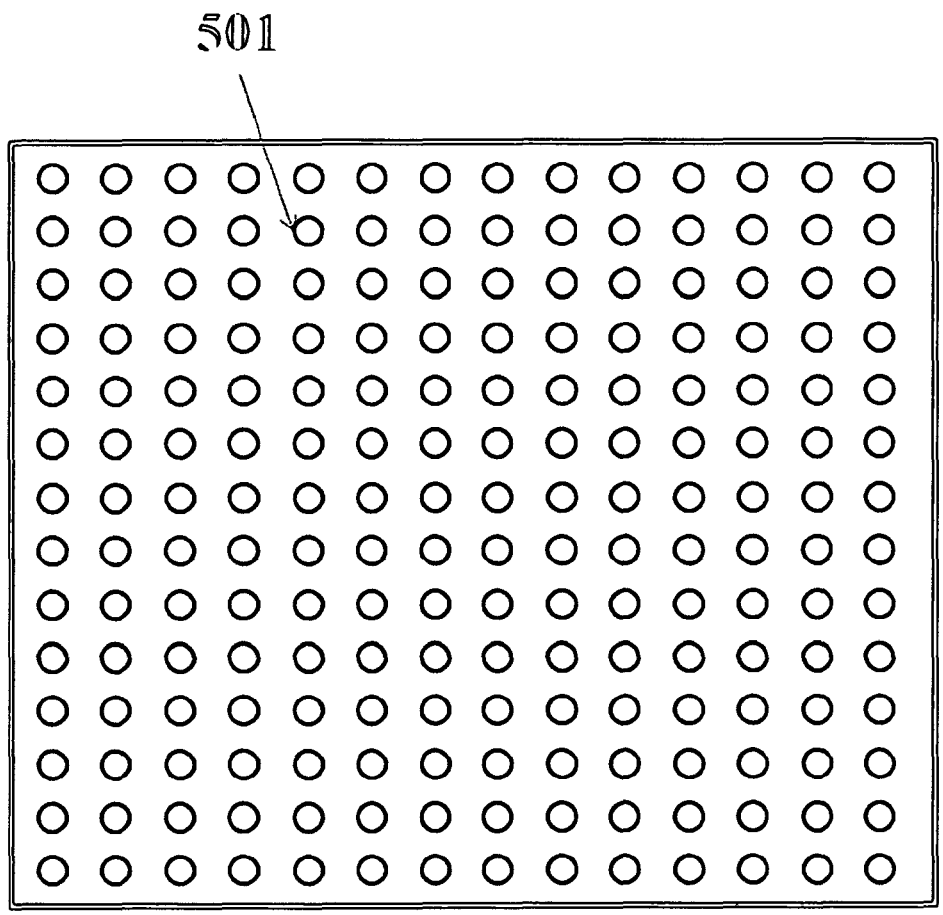
FIG. 5 shows an array of nanopore detectors.

The disclosure provides an array of nanopore detectors (or sensors) for detecting molecules and/or sequencing nucleic acids. With reference to FIG. 5, a plurality of (e.g., nucleic acid) molecules may be detected and/or sequenced sequenced on an array of nanopore detectors. Here, each nanopore location (e.g., 501) comprises a nanopore, which in some cases can be attached to a polymerase enzyme and/or phosphatase enzymes. There is also generally a sensor at each array location as described herein. In some examples, an array of nanopores attached to a nucleic acid polymerase is provided, and tagged nucleotides are incorporated with the polymerase. During polymerization, a tag is detected by the nanopore (e.g., by releasing and passing into or through the nanopore, or by being presented to the nanopore).

The array of nanopores may have any suitable number of nanopores. In some instances, the array comprises about 200, about 400, about 600, about 800, about 1000, about 1500, about 2000, about 3000, about 4000, about 5000, about 10000, about 15000, about 20000, about 40000, about 60000, about 80000, about 100000, about 200000, about 400000, about 600000, about 800000, about 1000000, and the like nanopores. In some instances, the array comprises at least 200, at least 400, at least 600, at least 800, at least 1000, at least 1500, at least 2000, at least 3000, at least 4000, at least 5000, at least 10000, at least 15000, at least 20000, at least 40000, at least 60000, at least 80000, at least 100000, at least 200000, at least 400000, at least 600000, at least 800000, or at least 1000000 nanopores.

The array of nanopore detectors may have a high density of discrete sites. For example, a relatively large number of sites per unit area (i.e., density) allows for the construction of smaller devices, which are portable, low-cost, or have other advantageous features. An individual site in the array can be an individually addressable site. A large number of sites comprising a nanopore and a sensing circuit may allow for a relatively large number of nucleic acid molecules to be sequenced at once, such as, for example, through parallel sequencing. Such a system may increase the through-put and/or decrease the cost of sequencing a nucleic acid sample.

The surface comprises any suitable density of discrete sites (e.g., a density suitable for sequencing a nucleic acid sample in a given amount of time or for a given cost). Each discrete site can include a sensor. The surface may have a density of discrete sites greater than or equal to about 500 sites per 1 mm$^2$. In some embodiments, the surface has a density of discrete sites of about 200, about 300, about 400, about 500, about 600, about 700, about 800, about 900, about 1000, about 2000, about 3000, about 4000, about 5000, about 6000, about 7000, about 8000, about 9000, about 10000, about 20000, about 40000, about 60000, about 80000, about 100000, or about 500000 sites per 1 mm$^2$. In some cases, the surface has a density of discrete sites of at least 200, at least 300, at least 400, at least 500, at least 600, at least 700, at least 800, at least 900, at least 1000, at least 2000, at least 3000, at least 4000, at least 5000, at least 6000, at least 7000, at least 8000, at least 9000, at least 10000, at least 20000, at least 40000, at least 60000, at least 80000, at least 100000, or at least 500000 sites per 1 mm$^2$.

In some examples, a test chip includes an array of 264 sensors arranged in four separate groups (aka banks) of 66 sensor cells each. Each group is in turn divided into three "columns" with 22 sensors "cells" in each column. The "cell" name is apropos given that ideally a virtual cell comprising a bi-lipid layer and inserted nanopore is formed above each of the 264 sensors in the array (although the device may operate successfully with only a fraction of the sensor cells so populated).

There is a single analog I/O pad which applies a voltage potential to the liquid contained within a conductive cylinder mounted to the surface of the die. This "liquid" potential is applied to the top side of the pore and is common to all cells in a detector array. The bottom side of the pore has an exposed electrode and each sensor cell may apply a distinct bottom side potential to its electrode. The current is then measured between the top liquid connection and each cell's electrode connection on the bottom side of the pore. The sensor cell measures the current traveling through the pore as modulated by the tag molecule passing within the pore.

Computer Systems

Figure 6:
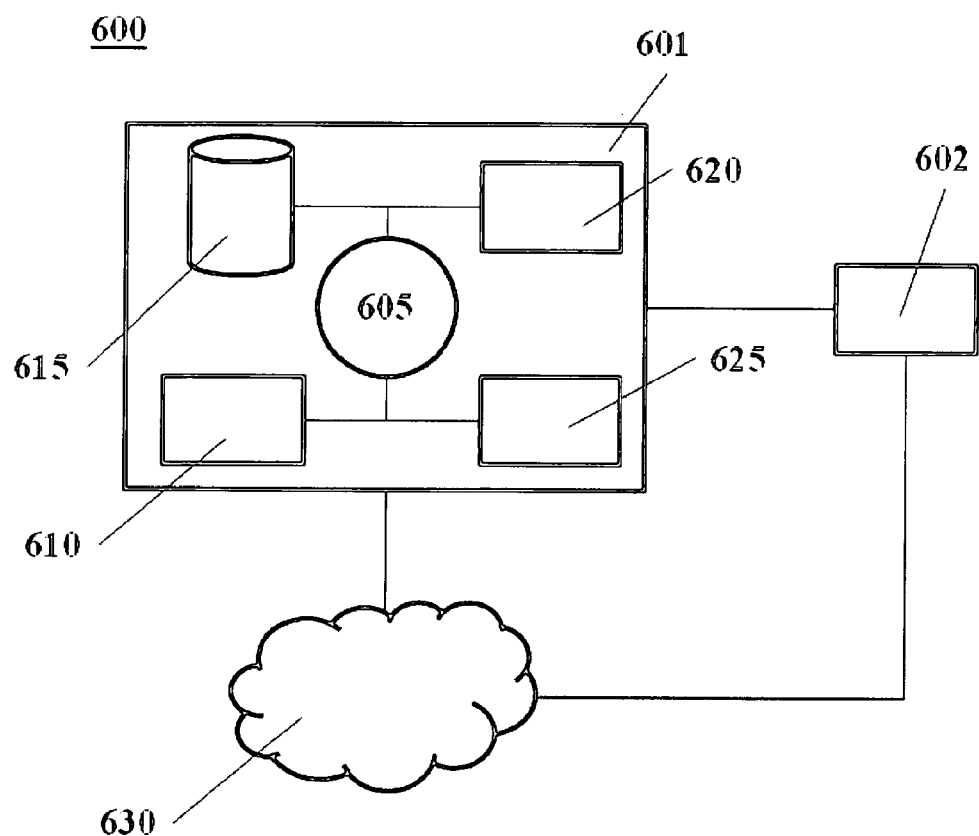
FIG. 6 shows a computer system configured to control a sequencer.

The devices, systems and methods of the disclosure may be regulated with the aid of computer systems. FIG. 6 shows a system 600 comprising a computer system 601 coupled to a nanopore detection and/or nucleic acid sequencing system 602. The computer system 601 may be a server or a plurality of servers. The computer system 601 may be programmed to regulate sample preparation and processing, and nucleic acid sequencing by the sequencing system 602. The nanopore detection and/or sequencing system 602 may be a nanopore-based sequencer (or detector), as described herein.

The computer system may be programmed to implement the methods of the disclosure. The computer system 601 includes a central processing unit (CPU, also "processor" herein) 605, which can be a single core or multi core processor, or a plurality of processors for parallel processing. The processor 605 can be part of a circuit, such as an integrated circuit. In some examples, the processor 605 can be integrated in an application specific integrated circuit (ASIC). The computer system 601 also includes memory 610 (e.g., random-access memory, read-only memory, flash memory), electronic storage unit 615 (e.g., hard disk), communications interface 620 (e.g., network adapter) for communicating with one or more other systems, and peripheral devices 625, such as cache, other memory, data storage and/or electronic display adapters. The memory 610, storage unit 615, interface 620 and peripheral devices 625 are in communication with the CPU 605 through a communications bus (solid lines), such as a motherboard. The storage unit 615 can be a data storage unit (or data repository) for storing data. The computer system 601 may be operatively coupled to a computer network ("network") with the aid of the communications interface 620. The network can be the Internet, an internet and/or extranet, or an intranet and/or extranet that is in communication with the Internet. The network can include one or more computer servers, which can enable distributed computing.

In some examples, the computer system 601 includes a field-programmable gate array (FPGA). The processor 605 in such a case may be excluded.

Methods of the disclosure can be implemented by way of machine (or computer processor) executable code (or software) stored on an electronic storage location of the computer system 601, such as, for example, on the memory 610 or electronic storage unit 615. During use, the code can be executed by the processor 605. In some cases, the code can be retrieved from the storage unit 615 and stored on the memory 610 for ready access by the processor 605. In some situations, the electronic storage unit 615 can be precluded, and machine-executable instructions are stored on memory 610.

The code can be pre-compiled and configured for use with a machine have a processer adapted to execute the code, or can be compiled during runtime. The code can be supplied in a programming language that can be selected to enable the code to execute in a pre-compiled or as-compiled fashion.

The computer system 601 can be adapted to store user profile information, such as, for example, a name, physical address, email address, telephone number, instant messaging (IM) handle, educational information, work information, social likes and/or dislikes, and other information of potential relevance to the user or other users. Such profile information can be stored on the storage unit 615 of the computer system 601. The nanopore detection and/or nucleic acid sequencing system 602 can be directly coupled to the computer system 601 or go through the cloud (e.g., internet) 630.

Aspects of the systems and methods provided herein, such as the computer system 601, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such memory (e.g., ROM, RAM) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

Formation of Bilayers

Described here are methods for creating lipid bilayers and nanopores on an array of electrodes (e.g., individually controlled) that make up a semiconductor nanopore sensor chip. The chip can be used for determining polymer sequence such as nucleic acid sequence.

Techniques for forming lipid bilayers over an array of electrodes on a semiconductor sensor chip are described herein. In an embodiment, liquids containing lipid molecules are inserted to the surface of the chip. The liquids are separated by bubbles. The lipid molecules can be distributed on the surface and the bubbles thin out the lipids to spontaneously form a lipid bilayer over each of the electrodes. Additional electrical stimulus may be applied to the electrodes to facilitate the bilayer formation. Solutions containing nanopore protein may be further applied on top of the deposited lipids. More bubbles may be rolled across the chip to facilitate the nanopore insertion into the bilayers. These techniques may occur with or without flow cells. In some cases, additional stimulus can be applied to induce bilayer or pore creation including, pressure, sonication, and/or sound pulses.

In an aspect, a method for forming a lipid bilayer for use in a nanopore sensor, comprises: (a) directing a buffer solution in flow channel comprising an electrode having a material layer thereon. The buffer solution can be electrically conductive, and the material layer can comprise one or more lipids. The method can comprise bringing the buffer solution in contact with the material layer, and applying one or more voltages to the electrodes and measuring a current through the electrodes to determine if at least a portion of the material layer has covered and sealed the electrodes and/or formed a bilayer over all or a portion of the electrode. The applied voltage may be sufficient to break the bilayer seal over the electrode and cause short circuit current flow. Based on a determination as to whether the at least the portion of the material layer has covered and sealed the electrodes and/or formed a bilayer over all or a portion of the electrode, a stimulus may be applied simultaneously to all the electrodes, groups of the electrodes, or individual electrodes to induce the at least the portion of the material layer to form the lipid bilayer adjacent to the electrode.

In some embodiments, the stimulus comprises at least one of a liquid flow over the surface of the electrode array, the sequential flow of one or more different liquids over the surface of the array, the sequential flow of any combination of one or more different liquids and bubbles over the surface of the array, an electrical pulse, sonication pulse, pressure pulse, or sound pulse. In some cases, the material layer comprises at least two types of lipids.

In some cases, the material layer comprises a pore protein. In some cases, the pore protein is *mycobacterium smegmatis* porin A (MspA) and/or alpha-hemolysin or a derivative of thereof with at least 70% homology to the amino acid sequence. In some instances, the material layer comprising one or more porin proteins includes one or more surfactants at a concentration less than the surfactant's critical micelle concentration.

In some cases, the stimulus comprises at least one of a liquid flow over the surface of the electrode array, the sequential flow of one or more different liquids over the surface of the array, the sequential flow of any combination of one or more different liquids and bubbles over the surface of the array, an electrical pulse, sonication pulse, pressure pulse, or sound pulse.

In an aspect, an automated method for creating a lipid bilayer on top of each one of multiple electrodes that make up an array of individually controlled electrodes and a method to insert a single pore into each bilayer atop each electrode in an array of individually controlled electrodes on a semiconductor sensor is described. By applying an appropriate external stimulus (e.g., electrical stimulus, pressure stimulus, sonication, or sound) to a lipid layer in close proximity to an electrode on an essentially planar surface, a bilayer can be induced to form over the electrode in an array of electrodes. Additionally, by applying an appropriate external stimulus (e.g., including electrical stimulus, pressure stimulus, sonication, or sound) to an individual electrode to the entire sensor chip that has lipid bilayers on one or more electrodes and that are covered with a solution containing nanopore proteins, a pore may be induced to insert into the bilayer. The result is that a bilayer is created automatically, without manual intervention, over multiple electrodes in an array of individually controlled electrodes in response to a stimulus and in a deterministic manner. In some cases, a single nanopore can be inserted into multiple electrode/bilayers in response to a stimulus and in a deterministic manner and therefore create a highly parallel array of individually controlled, electrical nanopore sensors. These arrays of individually controlled nanopore sensors may be created on an essentially planar semiconductor surface and that within the semiconductor material are created a portion or all of the circuitry needed to operate and control the individual electrodes.

In additional to the above ways of creating bilayers and pores, methods to create bilayers and pores on arrays of individually controlled electrical/nanopore sensors that are cost effective and simple are disclosed in this application and include; 1) activating lipid or lipid-porin protein mixes already on the sensor (pre-applied) and causing spontaneous bilayer creation or bilayer-pore creation, 2) activating lipid or lipid-porin protein mixes already on the sensor (pre-applied) and directly creating bilayers and or pores via electrical stimulation at the electrodes or stimulation to the system to create bilayers and or pores 3) activating lipid or lipid-porin protein mixes already on the sensor (pre-applied) and directly creating bilayers and or pores via contacting a bubble to or running a bubble across the surface of a sensor chip, 4) activating lipid or lipid-porin protein mixes already on the sensor (pre-applied) and distributing, and thinning the mixture on the surface of a sensor array using a bubble that prepares the surface for subsequent electrical stimulation at the electrodes or stimulation to the system to create bilayers and or pores, 5) a bubble method that applies, distributes, and thins a lipid mixture on the surface of a sensor array so that bilayers are created over multiple independent electrodes in an array, 6) a bubble method that applies, distributes, and thins a lipid mixture and therefore prepares the surface for subsequent electrical stimulation at the electrodes or stimulation to the system to create bilayers over multiple electrodes, 7) a bubble method that applies, distributes, and thins a porin protein mixture on the surface of a sensor array prepared with a lipid mixture so that pores are inserted over multiple independent electrodes in an array, 8) a bubble method that applies, distributes, and thins a porin protein mixture and therefore prepares the surface for subsequent electrical stimulation at the electrodes or stimulation to the system to create a single pore over multiple electrodes in an array, 9) a method describing the use of electrical stimulus to create a bilayer over the surface of an electrode that does not require the generation of a bubble over the surface of an electrode, 10) methods describing "stimulation to the system" mentioned above that comprise the use of sonication or pressure stimulus applied to one or more electrodes, or to the entire sensor chip, to create a bilayer and/or pore over the surface of an electrode or multiple electrodes, 11) a method of increasing the density of electrodes on a semiconductor array of electrodes for nanopore electrical sensing that is compatible with the methods for establishing bilayers and pores described above, 12) methods showing that no flow cell or an open single sensor chip containing an array of multiple electrode-nanopore sensors can support the methods identified, or a single flow cell on a single sensor chip containing an array of multiple electrode-nanopore sensors can support the methods identified above, or that multiple flow cells on a single sensor chip containing an array of multiple electrode-nanopore sensors can support the methods identified, 13) pressure of the liquid or bubble can be varied to improve successful bilayer or pore creation, and 14) temperature of the sensor chip and liquid can be varied to improve bilayer or pore creation.

There are multiple ways to create lipid bilayer and to insert the pore in the bilayer. In an embodiment, a semiconductor chip with multiple electrodes is presented. A liquid lipid solution is applied to the silanized prepared surface of the chip. The liquid lipid solution may be a solution of Decane and lipid molecules such as diphytanoylphosphatidylcholine (DPhPC). The solution may be applied on the surface by pouring, spraying, squeegee. The solution is dried down on the surface. The solution may be completely dried so that only powder form of DPhPC molecules are left. Or the solution may be dried down to a sticky state. Thus, the surface of the chip is functionalized by the pre-applied lipid molecules in a powder form or a sticky solution form. The chip is sealed and may be handled and shipped.

The semiconductor chip may contain a cover and the cover allows the user to pump in and pump out liquid across the chip. The user applies a buffer liquid, such as salt water, into the chip to activate lipid molecules. Once the dried lipid molecules contact with the buffer solution, the lipid molecules are hydrated. The pressure of the incoming buffer liquid may facilitate the spontaneous formation of a lipid bilayer on top of each electrode surface.

In all techniques described herein, the semiconductor chip may not contain a cover and the user applies a buffer liquid, such as salt water, onto the chip surface using a pipette or other instrument to activate lipid molecules. Once the dried lipid molecules contact with the buffer solution, the lipid molecules are hydrated. The pressure of the incoming buffer liquid may facilitate the spontaneous formation of a lipid bilayer on top of each electrode surface.

In another related embodiment where the semiconductor chip contains a cover, after the buffer liquid is applied into the chip, a bubble is pumped in and behind the bubble there is more buffer solution. The bubble sweeps across the chip and smoothes and thins out the newly hydrated pre-deposited lipid mix and cause the lipid molecules to sweep across the surface. After the bubble flows through, a lipid bilayer may be formed on top of each electrode surface.

In yet another related embodiment, after the bubble is applied and sweeps across the chip, an electrical signal is applied to the electrode(s) and the electrical stimulus may cause bilayer(s) to form on the electrode(s). The electrical stimulus with a voltage potential may disrupt the interface between the surface of the electrode and the lipid material around the electrodes to cause the abrupt quick formation of bilayers.

In another embodiment, the liquid lipid solution may further contain pore proteins, such as *mycobacterium smegmatis* porin A (MspA) or alpha-hemolysin. The solution containing lipid molecules and pore proteins are dried. The surface of the chip is prepared with silane molecules to make the surface hydrophobic. Lipid molecules and pore proteins in are deposited in a powder form or in a sticky state. The user may activate the chip by applying a buffer solution to the chip. The lipid molecules and the pore proteins are hydrated. A lipid layer with nanopore inserted may be spontaneously formed on top of each electrode surface.

In another related embodiment, after the buffer liquid is applied into the chip a bubble is pumped in and behind the bubble there is more buffer solution. The bubble sweeps across the chip and smoothes and thins out the newly hydrated pre-deposited lipid and pore mix and cause the lipid and/or pore molecules to sweep across the surface. After the bubble flows through, a lipid bilayer may be formed on top of each electrode surface and pore proteins are also inserted in the bilayer as nanopores.

In yet another related embodiment, after the bubble is applied and sweeps across the chip, an electrical signal is applied to the electrode and the electrical stimulus may cause bilayer to form on the electrode and nanopore to be inserted in the bilayer. The electrical stimulus with a voltage potential may disrupt the surface of the electrode and affects the lipid material around the electrodes to cause the abrupt quick formation of bilayers and nanopores in the bilayers.

In another embodiment, the semiconductor chip is just silanized and does not have any pre-applied molecules, such as lipid molecules or pore proteins, functionalizing the surface of the chip. The user first flushes the surface of the chip using salt water. Then an aliquot of lipid and Decane is inserted onto the chip. A bubble is followed to smear the lipid material and distributes and thins it out on the surface of the chip. Lipid bilayers are spontaneously created over multiple electrodes via contact and distribution of the bubble.

In another related embodiment, the lipid bilayers may not be spontaneously created after the bubble. A subsequent electrical stimulation is applied to the electrodes. The electrical pulse causes the bilayers to be formed on the electrodes.

In yet another related embodiment, after the bubble sweeps across the chip and lipid material is distributed, a salt water flow follows. After the salt water, a pore protein solution is inserted into the chip. Another bubble is followed to smear and thin the pore protein mixture on the surface of the chip so that pores are inserted over the multiple independent electrodes in an array via a form of contact or pressure from the bubble.

In still another related embodiment, after the pore protein solution and the second bubble are inserted, a subsequent electrical stimulation is applied at the electrodes to create nanopores in the lipid bilayers over the multiple electrodes in an array.

In another embodiment, an aliquot of lipid and Decane gets inserted into the chip filled or covered with an ionic solution (such as salt water). A subsequent electrical stimulation is applied to the electrodes. The electrical pulse causes the bilayers to be formed on the electrodes. In this embodiment, there is no bubble inserted to facilitate bilayer formation. The lipid is well distributed around the electrodes over the surface of the chip. A voltage applied on the electrodes causes the disruption the lipid material at the edge of the electrodes and induces formation of a lipid bilayer.

The semiconductor nanopore sensor chip may contain one or more channels through which liquid and reagents can flow. In an embodiment, each channel has two rails, one on each side of the channel. The electrodes may be on the bottom surface of the channel. The electrodes may further be on the sidewall surface of the channel (on the rails). Thus the density of electrodes for each channel may be increased by creating electrodes on the bottom and sidewall surfaces.

In an embodiment, one or more flow cells may be utilized on the semiconductor chip. Each flow cell may be used to insert solutions and bubbles for one of the channels on the chip. A flow cell is a path that liquids, bubbles and reagents can pass through. The channels on the chip acting as entire or portions of a flow cell may be independent so that the chip can process multiple different samples independently and simultaneously.

In an embodiment, there is no channel or flow cell on the chip. The chip is pre-applied with liquid lipid solution, or liquid lipid-pore mixture solution. The solution is dried to a powder form or a sticky state. A liquid buffer solution is applied to the chip to activate the lipid or lipid-pore mixture. An electrical signal is applied to the electrode and the electrical stimulus may cause bilayer to form on the electrode. The electrical stimulus with a voltage potential may disrupt the surface of the electrode and affects the lipid material around the electrodes to cause the abrupt quick formation of bilayers. Furthermore, if there is activated pore protein present, the electrical stimulus may further facilitate the insertion of pore molecules into the lipid bilayers.

In some embodiments, the pressure of the liquid or bubble may be varied to improve the bilayer or nanopore creation. In some embodiments, the temperature of the chip and the liquid may be varied to improve the bilayer or pore creation. For example, slightly cooler than room temperature may be applied when the bilayer is formed; slightly warmer than room temperature may be applied when the nanopore is inserted into the lipid bilayer.

In an embodiment, a chip may have one of the four sides of the sealed chip left open and accessible. The opposite side may also have a single hole to which a tube can contact and connect. If the chip is stood up so that it is vertical with the hole and tube at the bottom and the open end of the chip at the top, buffer liquid and reagents can be added through the top and bubbles can then be released, at a controlled pace, from the bottom and travel up the sealed cavity and flow across the chip. This system may not have trains of bubbles separating liquid fractions roll across the chip. It smoothes out any substances that are added through the open top of the packaged chip and runs down the surface of the chip inside. Conversely, it is possible to insert liquids and reagents through the single tube at the bottom of the apparatus and this may be advantageous when automated time series additions of reagents may be required.

In all techniques described herein, it is possible to couple the sensor chips to, or place the sensor chips in, an apparatus that will in an automated fashion apply any combination of liquids, reagents, bubbles, electrical stimulus pulses, pressure or pressure pulses, temperature or temperature pulses, sonication pulses, and or sound pulses to the sensor chip to cause the automated creation of bilayers, creation of pores, maintenance of bilayers and pores including their re-creation, capture and reading of the biological molecules applied to the nanopore sensor chip, and to provide real-time and/or end-point details of the status of all sensors and all characteristics of the instrument' performance. The apparatus can allow any level of operator manual intervention or to allow creation of custom tests. The apparatus may apply different signals and/or reagents or act upon the sample or chip in response to the result of a prior test signal or reagent addition allowing the apparatus to operate fully automatically. Such a system can allow the operator-free running of time-course experiments or allow the refreshing of the nanopore system to re-functionalize the surface of the sensor chip to continue testing.

In all techniques described herein, the application of a stimulus to induce creation of bilayers or creation of pores can also include the application of pressure, temperature, sonication, or sound to the chip to stimulate the desired bilayer/pore creation events.

In all techniques described herein, the semiconductor chip may not contain a cover and the user applies any and all buffers, reagents, and bubbles manually through the use of a pipette or other instrument. This manual application of these techniques can be coupled with any applied stimulus outlined herein to induce the desired bilayer and/or pore formation.

Flow cell or simple bubble system can also greatly help the insertion of pores by applying the pore protein solution evenly around the sensor chip surface and causing spontaneous pore insertion or setting up the surface so that electrical stimulus encourages the quick insertion of pores into the bilayers. A flow cell or simple bubble system can also help hydrate a dried lipid-pore-protein mix that may form both spontaneous bilayers and pores after smoothing or mixing in an appropriate buffer with or without bubbles.

FIG. 7 illustrates a sample method for forming a lipid layer over the electrodes on one or more flow channels of a sensor chip. The sensor chip may be a planar chip contains multiple electrodes embedded in, and essentially planar to, a non-conductive or semiconductor surface on which is located on the surface of flow channels. The method comprises steps of 701 flowing in a lipid solution comprising at least one type of lipids through each of the flow channels; 702 depositing the lipids on the surface of electrodes; 703 smoothing and thinning the deposited lipids with a follow-on bubble in each of the flow channels; 704 filling each of the flow channels with a buffer solution, the buffer solution being electrically conductive; 705 measuring currents through the electrodes to determine if a lipid bilayer is formed over each the electrodes; and 706 if the lipid bilayers are not formed on any of the electrodes yet, applying a stimulus (e.g., electrical stimulus) to induce the lipids on the surfaces to form lipid bilayers over the electrodes. In some cases, a voltage is applied to test bilayers and then to insert pores. In some instances, however, the voltage is not applied to create bilayers.

In some embodiments, the lipid solution may comprise at least two types of lipids. The lipid solution may further comprise at least one type of pore proteins. The pore proteins may comprise *mycobacterium smegmatis* porin A (MspA) or alpha-hemolysin. The method may further comprises step of flowing a non-lipid solution containing pore proteins over the deposited lipids in each of the flow channels; thinning the pore proteins and deposited lipids with a second bubble in each of the flow channels. The method may further comprises flowing a pore protein solution, an additional air bubble and an additional liquid solution through the flow channel, the pore protein solution and the liquid solution being separated by the air bubble; and applying an electrical stimulus through at least some of the electrodes to facilitate an insertion of the pore protein in the lipid bilayer. All the steps of flowing solutions and bubbles may be repeated in any order and combination to achieve the lipid bilayer formation and nanopore insertion in the bilayer. The lipid may be diphytanoylphosphatidylcholine (DPhPC), palmitoyl-oleoyl-phosphatidyl-choline (POPC), dioleoyl-phosphatidyl-methylester (DOPME), dipalmitoylphosphatidyl-choline (DPPC), phosphatidylcholine, phosphatidylethanolamine, phosphatidylserine, phosphatidic acid, phosphatidylinositol, phosphatidylglycerol, or sphingomyelin. The liquid lipid solution may further contain organic solvent such as Decane.

In some embodiment, the buffer solution may contain ionic solution, such as sodium chloride or potassium chloride solution. The buffer solution may further contain Ferrous Cyanide or Ascorbic Acid. In some embodiments, the pressure of the bubbles is adjusted substantially at or slightly above the atmospheric pressure to improve the bilayer formation or nanopore insertion.

Figure 8:
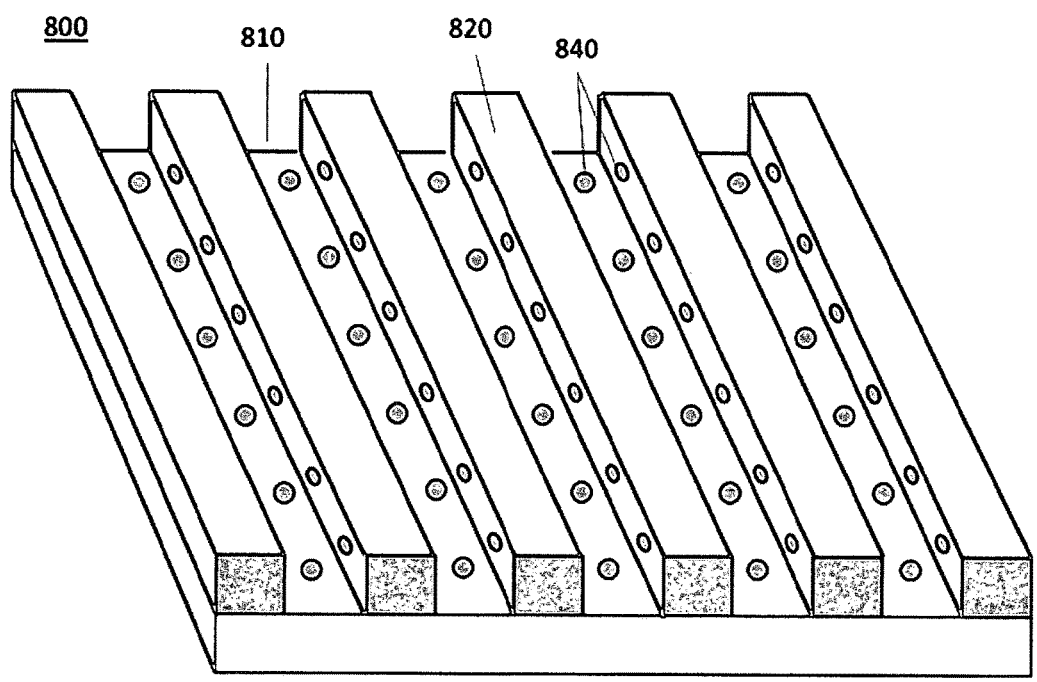
FIG. 8 shows an example of a semiconductor sensor chip.

FIG. 8 illustrates a sample semiconductor sensor chip, in accordance with an embodiment of the present disclosure. The sensor chip 800 comprises multiple flow channels 810. Each flow channel has multiple electrodes 820 embedded in, and essentially planar to, a non-conductive or semiconductor surface on which is located on the surface of the flow channels 810. The surface of the electrodes is silanized to be hydrophilic. The surface of the flow channel other than the electrodes is hydrophobic. The flow channels 810 are separated by guide rails 840 along the flow channels. The channel width may be wide enough to accommodate two or more rows of electrodes. The electrodes may be fabricated on the bottom surface of the flow channels, as well as the side walls of the guide rails, as shown in FIG. 8. In some embodiment, the top side of the flow channels may be sealed.

In an aspect, a method for forming a lipid bilayer over the electrodes on one or more flow channels of a sensor chip comprises: (a) flowing in a lipid solution comprising at least one type of lipids through each of the flow channels; (b) depositing the lipids on the surface of electrodes; (c) smoothing and thinning the deposited lipids with a follow-on bubble in each of the flow channels; (d) filling each of the flow channels with a buffer solution, the buffer solution being electrically conductive; (e) measuring currents through the electrodes to determine if a lipid bilayer is formed over each the electrodes; and (f) if the lipid bilayers are not formed on any of the electrodes yet, applying a stimulus to at least one of the electrodes to induce the lipids on the surfaces to form lipid bilayers over the electrodes. The stimulus can comprise at least one of electrical pulse, sonication pulse, pressure pulse, or sound pulse.

In some embodiments, the lipid solution comprises at least two types of lipids. In some embodiments, the lipid solution further comprises at least one type of pore proteins.

In some embodiments, the method further comprises, after (c): (c1) flowing a non-lipid solution containing pore proteins over the deposited lipids in each of the flow channels; and (c2) thinning the pore proteins and deposited lipids with a second bubble in each of the flow channels. In some embodiments, the method further comprises, after (c2): (c3) repeating steps (b), (c), (c1), or (c2) in any order or combination.

In some embodiments, the method further comprises: (g) flowing a pore protein solution, an additional air bubble and an additional liquid solution through the flow channel, the pore protein solution and the liquid solution being separated by the air bubble. In some embodiments, the method further comprises: (h) applying an electrical stimulus through at least some of the electrodes to facilitate an insertion of the pore protein in the lipid bilayer.

In some embodiments, the lipid is diphytanoylphosphatidylcholine (DPhPC), palmitoyl-oleoyl-phosphatidyl-choline (POPC), dioleoyl-phosphatidyl-methylester (DOPME), dipalmitoylphosphatidylcholine (DPPC), phosphatidylcholine, phosphatidylethanolamine, phosphatidylserine, phosphatidic acid, phosphatidylinositol, phosphatidylglycerol, or sphingomyelin.

In some cases, at least some of the liquid lipid solutions contain an organic solvent (e.g., decane). The pore proteins can comprise *mycobacterium smegmatis* porin A (MspA) or alpha-hemolysin. In some cases, the buffer solution contain ionic solution (e.g., sodium chloride or potassium chloride). In some instances, at least some of the buffer solution contains Ferrous Cyanide or Ascorbic Acid.

In some embodiments, the pressure of the bubbles is substantially at or slightly above the atmospheric pressure. In some cases, the surface of the electrodes is hydrophilic. In some instances, the surface of the flow channel other than the electrodes is hydrophobic.

In some embodiments, the method further comprises, before (a), any one or more of of: (a1) rendering the surface of the flow channel other than the electrodes hydrophobic by silanized the surface of the flow channel other than the electrodes; (a2) forming a plurality of flow channels on a surface of the chip; (a3) fabricating the electrodes on a surface of each of the flow channels; (a4) separating the flow channels by building guide rails along the flow channels; (a5) fabricating the electrodes on a side surface of each of the guide rails; and (a6) sealing the top side of each of the flow channels.

A method of creating a chip having a bilayer is to flow an ionic solution across the chip. In some cases, the flow is a "train" of interspersed lipid solution and ionic solution aliquots (e.g., alternating lipid solution and ionic solution). The flow can go through supply tubing and across the chip. The train can have approximately 5 uL of lipid and then 5 uL of ionic solution, and can be repeated 1, 2, 3, 4, 5, 6, 7, 8, 9, 10, or more times. The train of solutions can be pumped back and forth across the surface of the biochip approximately 2, 3, 4, 5, 6, 7, 8, 9, 10, or more times. The coverage and/or seal can then be electrically checked.

In some cases, the train of solutions is followed by an assembly step. In some cases, the assembly step involves flowing a bubble across the chip. In some instances, coverage of cells (electrodes), leakage or seal resistance at each electrode, and the voltage applied at which the seals and/or bilayers can be checked electrically.

In some cases, the assembly operation is repeated until approximately the following test results are attained: (1) about 190 or more electrodes are covered; (2) At least about 120 membranes (e.g., lipid layers) are popped at an applied voltage of less than −1V; (3) of the lipid layers that popped in (2), 69 or more have popped between about −300 mV to −700 mV; (4) the number of electrodes with a seal resistance less than about 50 Giga-ohms is less than 15; and (5) if the number of cells which show any recorded leakage current exceeds 50 then the median of the seal resistance is greater than 150 Giga-ohms.

If some or all of these criteria are met, then a bubble of approximately 10 uL can be flowed across the chip and a final test of (1), (4), and (5) can be performed. If this passes, then the program moves to pore insertion protocol. The program can be implemented with the aid of a computer system (e.g., upon execution by a processor), such as, for example, the computer system 601 of FIG. 6.

In some cases, the pore insertion protocol includes applying 5 uL of pore protein solution to the chip and electroporating to insert the pores into the bilayer. At the end of the electroporation operation, the chip is checked for pore yield and if the criteria are passed, sample and test reagents are applied.

In some instances, the total time for bilayer and pore insertion is, on average, 15 minutes for bilayer creation and 20 minutes for pore insertion for a total of 35 minutes.

Any number of wells can be covered by a membrane (e.g., lipid bilayer) with inserted pore (e.g., pore yield). In some cases, the pore yield is about 10%, about 20%, about 30%, about 40%, about 50%, about 60%, about 70%, about 80%, about 90%, and the like. In some cases, the pore yield is at least about 10%, at least about 20%, at least about 30%, at least about 40%, at least about 50%, at least about 60%, at least about 70%, at least about 80%, at least about 90%, and the like.

In some embodiments, the parameters applied to the electrode chip and to a test set-up are 1M KCl, pH 7.5, current fluidic flow rates, sea level atmospheric pressure, and room temperature.

Trapped Probes

In an aspect, the present disclosure provides methods of capturing, detecting, counting, sorting, binning, and enriching individual molecules (e.g., proteins) from a heterogeneous or homogeneous mixture.

Techniques for trapping, detecting, sorting, counting, isolating, collecting and/or binning of single molecules in a molecule by molecule fashion have been disclosed. In some embodiments, a probe molecule trapped in a nanopore is used for such purposes. In some embodiments, a Nanopore Readable Complex (NRC) that includes a probe molecule is used for such purposes. In some embodiments the NRC includes a probe molecule that can be captured, trapped, threaded through, and/or read by a nanopore. In some embodiments, the probe molecule ("Probe") includes one or more of the following portions: (1) a probe section or sequence that can bind to a target molecule directly or bind to a reporter molecule that binds to a target molecule; (2) variable temperature caps (VTC) attached to one or more ends of the probe molecule, the variable temperature caps are temperature sensitive and can assume bulky 2-dimensional and/or 3 dimensional structures at certain temperature ranges and linear structure at other temperature range; (4) one or more verification section(s) that can be read by a nanopore to identify the NRC, the probe molecule incorporated in the NRC, target molecule attached directly to the probe molecule or via a reporter molecule, and/or state of the NRC (e.g., where there is a reporter molecule and/or a target molecule attached to the NRC); (5) a reporter binding section for binding to a reporter molecule; (6) purification tags for subsequent isolation or purification; (7) unique address ID section; and/or (8) one or more "read switches" sections that change states/characteristics upon threading through the pore to indicate that the probe has been read by the nanopore (e.g., threaded through the nanopore for electrical signal detection).

In an aspect, a method for detecting a target molecule comprises: (a) providing a chip comprising a nanopore in a membrane that is disposed adjacent or in proximity to a sensing electrode; (b) directing a nucleic acid molecule through the nanopore. The nucleic acid molecule can be associated with a reporter molecule. The nucleic acid molecule can comprise an address region and a probe region. The reporter molecule can be associated with the nucleic acid molecule at the probe region. The reporter molecule can be coupled to a target molecule. In some cases, the method further comprises (c) sequencing the address region while the nucleic acid molecule is directed through the nanopore to determine a nucleic acid sequence of the address region; and (d) identifying, with the aid of a computer processor, the target molecule based upon a nucleic acid sequence of the address region determined in (c).

In some embodiments, the probe molecule in (b) is stopped and held in the pore by the binding of the reporter molecule to the probe region of the molecule in (b) (and the rate of progression of the probe through the nanopore may be reduced based upon the association of the reporter molecule with the nucleic acid molecule).

In some cases, up to 3, 4 or 5 bases of the nucleic acid molecule are identified when the rate of progression of the nucleic acid molecule through the nanopore is reduced. In some instances, the bound reporter completely stops the molecule that is in the pore. The hybridized complex can comprise the probe molecule in the pore and the reporter attached to the probe molecule. The reading can be accomplished by the addition of speed bumps.

In some cases, without the ends of the probe having formed bulky structures, the probe forms a bulky structure at one end so the probe will stay in the pore.

In some embodiments, the NRC also includes a reporter molecule ("Reporter") that binds to the probe molecule. The reporter molecule can be (a) any molecule that may bind to a single polymer, including peptides, proteins, nucleic acids, nucleic acid analogues, DNA, RNA, siRNA, shRNA, peptide nucleic acids, glycol nucleic acids, methylated and/or non-methylated nucleic acids, etc., and/or (b) any molecule that may bind to a multi-strand polymer, including peptide strands, proteins, nucleic acids, and other biological and chemical polymers. In some embodiments, the reporter molecule can be made unique for a particular source of a target molecule (e.g., from a particular sample) and identification of the reporter molecule can be used to identify the source of the target molecule. In some embodiments, the reporter molecule can be captured and bound to a probe molecule, and counted, sorted, collected and/or binned using the techniques disclosed herein.

In some embodiments, the Nanopore Readable Complex (NRC) allows Probe or Probe-NRC to be inserted in a pore in a unidirectional manner. In some embodiments, the NRC forms a bulky structure at one end and remains in its linear form at the other end under certain conditions. Since the formed bulky structure is too large to be threaded through the nanopore of the nanopore detector (e.g., temperature range), the NRC can only be captured and threaded through a nanopore from the linear end of the NRC, resulting in directional reading of the NRC by the nanopore. In some embodiments, directional threading and reading (e.g., from 5' end of the NRC) can provide cleaner read signals of the NRC in nanopore.

In some embodiments, the NRC is trapped in a nanopore of a nanopore detector, consequently trapping the Probe included in the NRC in the nanopore. In some embodiments, trapping the probe molecule in the nanopore allows the same probe molecule to be used repeatedly to capture, detect, characterize, sort, collect, and/or bin sample molecules.

In some embodiments, it is possible to verify whether a NRC and a probe included in the NRC is inserted correctly in a nanopore. In some embodiments, the NRC may include a leading end identifier (e.g., an unique sequence present at the leading end that can be read when the NRC is threaded to the leading end to give a distinguishable signal level) identifying the correct leading end and/or a trailing end identifier (e.g., an unique sequence present at the trailing end and can be read when the NRC is threaded to the trailing end to give a distinguishable signal level) identifying the correct trailing end. When the NRC is inserted into a nanopore of a nanopore detector, the NRC can be threaded to its trailing end and the sequence at the trailing end is read by the nanopore detector. If the sequence read matches the signal for the correct trailing end, it confirms that the NRC has been inserted correctly (e.g., inserted from the 5' end) and the trailing end cap (e.g., trailing end hairpin structure) has been properly formed. When the NRC trapped in the nanopore is threaded to its leading end and the sequence at the leading end is read by the nanopore detector, if the sequence read matches the signal for the correct leading end, it confirms that the NRC has been inserted correctly and the leading end cap (e.g., leading end hairpin structure) has been properly formed. If it is shown that the NRC has been properly inserted and the end caps have been properly formed, the Probe (included in the NRC) trapped in the nanopore is ready for use.

In some embodiments, the NRC may include "read switch" section that can be used to determine whether the probe molecule has been read once. In some embodiments, the characteristics and/or properties of the read switch alters once the probe has been read once. In some embodiments, one or more molecules or molecular fragments are attached to a probe molecule to serve as a molecular read switch. The molecule or molecular fragments fall off from the probe molecule once the probe passes through the nanopore. Thus, the presence of the molecular read switch indicates that the probe has not been read (since the probe molecule has not been threaded through the nanopore to cause the read switch to change state), the absence of the molecular switch indicates that the probe molecule has been read (since the probe has been threaded through the nanopore to cause the read switch to change state). The read switch allows quantitative analysis of probe molecules and consequently the reporter molecules and/or the sample molecules attached to the probe molecules in a sample. In some embodiments, one or more types of probe molecules are incubated with sample molecules to form probe-sample molecule complexes. The probe-sample molecule complexes can be placed on a single nanopore detector array for analysis. Each nanopore can grab one probe-sample molecule complex and read it to determine what type of probe-sample molecule/probe/sample that has been captured. Once the probe-sample molecule complex has been read, the read switch changes its state (e.g., the switch molecule falls off from the probe). The read probe-sample molecule complex is released back into the buffer surrounding the nanopore. The nanopore then grabs another probe ample molecule and read it again. If the probe-sample molecule has been read before, the read switch will not be detected. If the probe-sample molecule has not been read before, the read switch will be detected. Probe-sample molecules that have been read before can be identified and not counted, so no double counting of probe-sample will occur. In this way, a particular type of probe-sample molecules and sample molecules can be accurately counted.

In some embodiments, it is possible to determine whether the right molecule (e.g., the right sample molecule or reporter molecule) has been attached to the probe correctly. In some embodiments, since a given molecule will bind to specific region on a probe molecule. When the probe-molecule is read by a nanopore detector, it will be stalled at a position where the molecule is attached to the probe. The electrical signal read when the molecule is stalled corresponds to the structure/sequence of the section of probe in front of the molecule binding site on the probe. It can be used to identify the structure/sequence of the section of probe in front of the molecule binding site on the probe. If the structure/sequence of the probe in front of the binding site of the molecule is unique and gives distinguishable electrical signal, the electrical signal can be used to identify the molecule and determine whether the correct molecule has been bound to the probe.

In some embodiments, it is possible to identify which sample a molecule originates, even if the molecule is in a sample containing molecules from different samples. In some embodiments, sample molecules bind to probe molecules via intermediary molecules (e.g., reporter molecules), each type of molecules bind to a unique type of intermediary molecules, each type of intermediary molecules bind to a unique location on a probe molecule. If sample molecules from a first sample are allowed to bind to a first type of intermediary molecules, sample molecules from a second sample are allowed to bind to a second type of intermediary molecules, the origin of a molecule in a mixture containing molecules from the first and the second samples can be determined by determining the identity of the intermediary molecule bound to the molecule. In some embodiments, the identity of an intermediary molecule (e.g., reporter molecule) can be determined from the signal generated when the intermediary molecule is bound to a probe molecule and the sequence before the intermediary molecule binding location on the probe is read.

In some embodiments, relative counts or concentrations of a particular type of molecule from different samples can be accurately determined. For example if a first type of dehydrogenase binding intermediary molecules are incubated with a healthy tissue sample, a second type of dehydrogenase binding intermediary molecules are incubated with a diseased tissue sample. The two samples are then mixed together an analyzed using a single nanopore detector array. In some embodiments, the dehydrogenase molecules from a particular sample can be selectively counted, released, and collected without disrupting the probe molecule and/or the nanopore detector. In some embodiments, the relative concentration of the dehydrogenase molecules from the healthy sample and the diseased sample can be accurately determined by comparing the intermediary molecules from the healthy sample and diseased sample bound to the probe molecules on the nanopore array.

In some embodiments, a NRC molecule includes one or more isolation tags that help to isolate the NRC molecule and other molecules (e.g., reporter and sample molecule) attached to the NRC molecule. In some embodiments, the isolation tags are attracted to magnetic sources and can be used to pin the NRC molecules and other molecules attached to the NRC molecules to a magnetic source for isolating the NRC molecules and the other molecules attached to the NRC molecules.

In some embodiments, the probe molecule can be dissociated from reporter/sample molecule without damaging the probe molecule. In some embodiments, temperature can be increased to dissociated reporter molecule/sample molecule without damaging the probe molecule and the nanopore.

Figure 9:
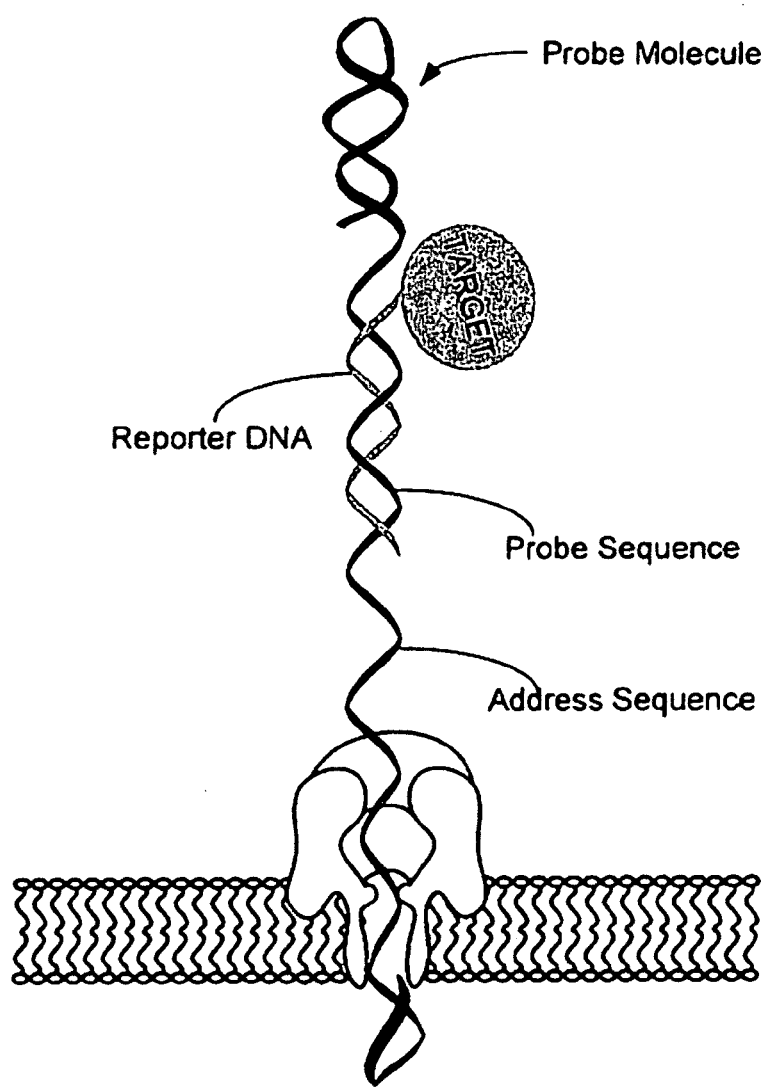
FIG. 9 illustrates an example of probe molecule trapped in a nanopore.

FIG. 9 illustrates an example of probe molecule trapped in a nanopore. The probe molecule includes a probe sequence for binding to a reporter that binds to a target molecule. The target molecule can be any suitable molecule such as proteins and peptides, etc. The probe molecule is trapped in the nanopore using bulky structures as end caps. The bulky structures may be temperature sensitive, and may form and disassociate depending on the temperature.

Figure 10:
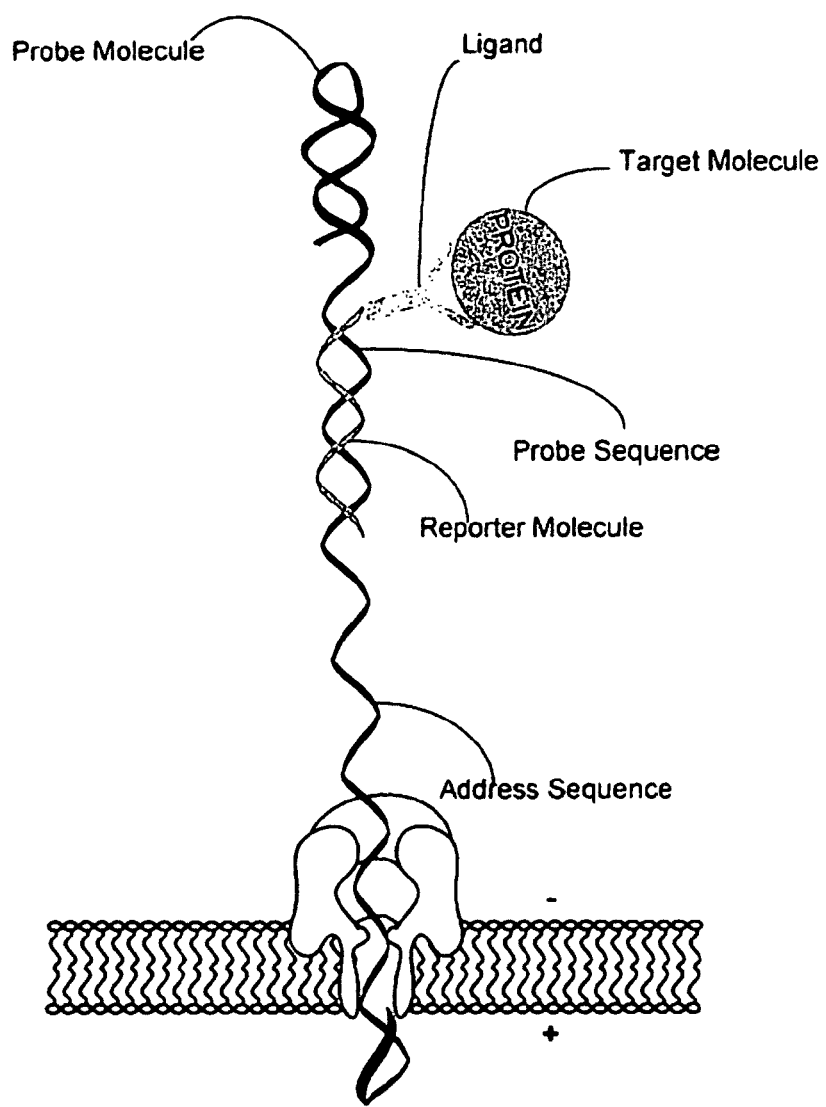
FIG. 10 illustrates an example probe molecule trapped in nanopore.

FIG. 10 illustrates an example probe molecule trapped in nanopore. In the example shown, the probe molecule includes a probe sequence for binding to a reporter molecule that binds to a ligand that binds to a target molecule. The ligand is an antibody that binds to the target molecule. The target molecule can be any suitable molecule such as proteins, peptides, bacteria, or chemical moieties, etc. The reporter molecule is a single stranded polymer sequence. The probe molecule is trapped in the nanopore using bulky structures as end caps. The bulky structures may be temperature sensitive and form and disassociate depending on the temperature. Although not illustrated, target DNA, RNA, or other nucleotide molecules can directly bind to the probe molecule at the probe sequence. The identity of the target nucleotide can be determined based on the signals generated when the sequence in front of probe molecule, the address sequence is read using a nanopore.

Figure 11:
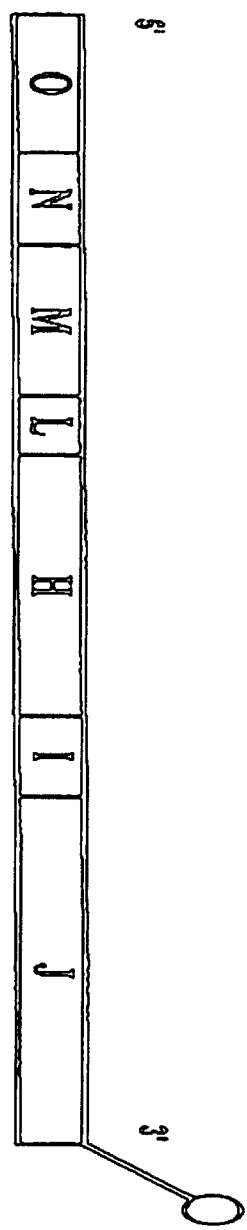
FIG. 11 illustrates an example linear sequence of a probe molecule.
Figure 12:
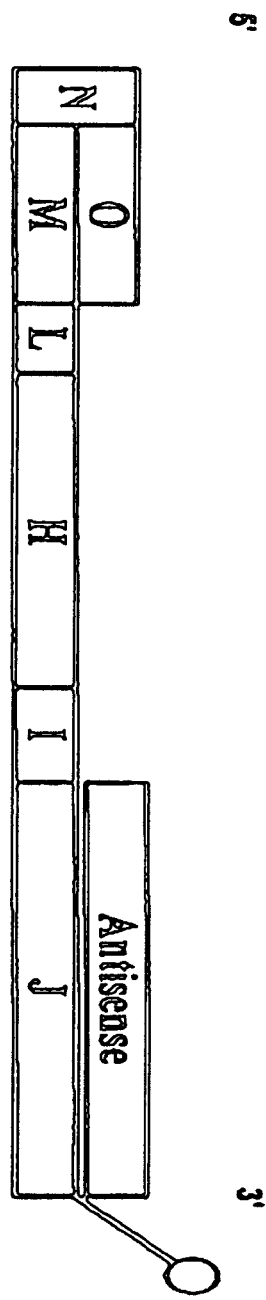
FIG. 12 illustrates an antisense strand can be bound to form a double stranded cap that is bulky enough to be excluded to from nanopore.

FIG. 11 illustrates an example linear sequence of a probe molecule. The probe molecule includes a leading end (at the 5' end) and a trailing end (at the 3' end). The trailing end includes IJ. As illustrated in FIG. 12, an antisense strand can be bound to J to form a double stranded cap that is bulky enough to be excluded to from nanopore. Alternatively J may fold and bind upon itself in a 2D or 3D conformation to form the trialing end cap. The leading end includes ONML. O folds back to bind to M to form a cap having a hairpin structure. The double stranded cap forms at a higher temperature than the leading end cap. The orientation of leading and trailing ends of the polymer can be changed by adjusting the melting temperatures of the cap. The high melting temperature cap becomes the trailing end and the low melting temperature becomes the leading end. The leading end also includes an end identifier sequence L that can be used to identify the leading end when it is read by the nanopore when the low temperature cap at the leading end is pushed against the nanopore. The trailing end includes an end identifier sequence I that can be used to identify the trailing end when it is read by the nanopore when the high temperature cap at the trailing end is pushed against the nanopore.

Figure 13:
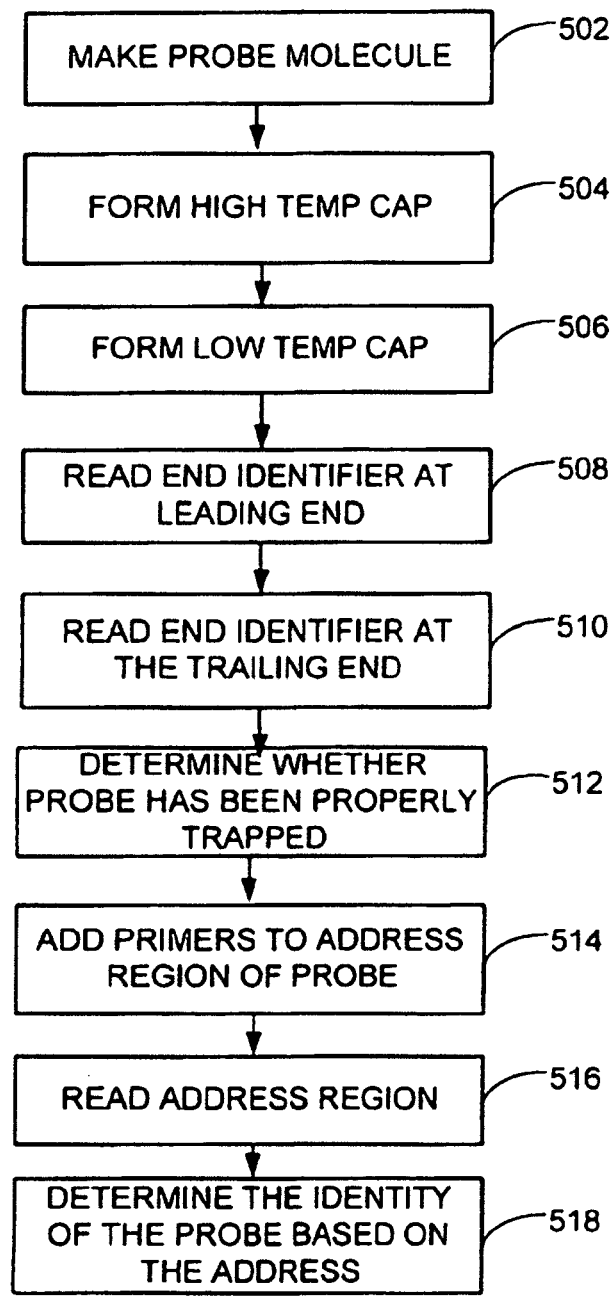
FIG. 13 illustrates a process flow for trapping and characterizing a probe molecule using a nanopore.

FIG. 13 illustrates a process flow for trapping and characterizing a probe molecule using a nanopore. At 502, probe molecule with the proper sequence is made. At 504, a high temperature cap is formed at one end of the probe, by for example lowering the temperature to below the melting temperature of the high temperature cap structure. At 506, the probe molecule is threaded through the nanopore from the leading end (low temperature cap end). At 508, the temperature is lowed to below the melting temperature of the low temperature cap structure to allow the low temperature cap to form on the leading end. At 508, the probe is pulled to one end (either leading end or trailing end), the end identifier is read. At 510, the probe is pulled to the other end and the end identifier is read. At 512, determination is made as to whether the correct end identifiers have been read, if yes, the probe has been captured in the nanopore. At 514, speed bumps are attached to an address region of the probe. At 516, the probe threaded through the nanopore so the primers attached to the address region of the probe are pushed against the nanopore. The probe sequence at the address region is read when each primer stalls the progression of the probe molecule. At 518, determination is made as to the identity of the probe molecule based on the read address sequence of the probe molecule.

Figure 14:
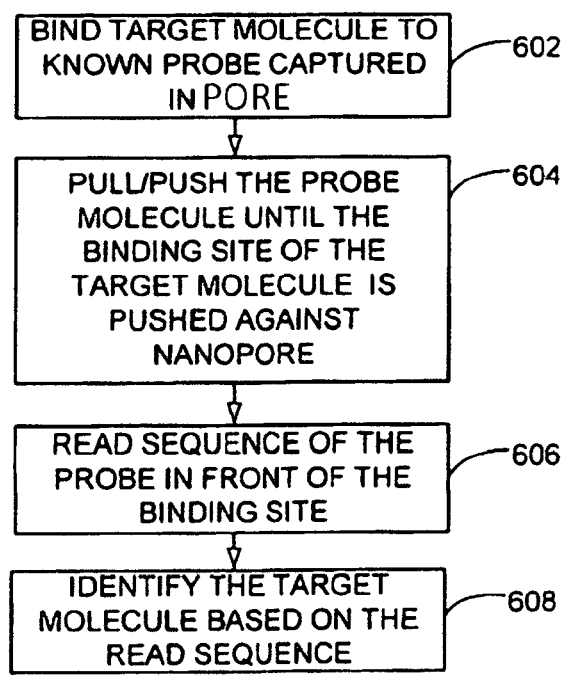
FIG. 14 is a process flow for capturing and identifying, counting, sorting and/or collecting target molecules using a nanopore trapped probe.

FIG. 14 is a process flow for capturing and identifying, counting, sorting and/or collecting target molecules using a nanopore trapped probe. At 602, target molecule is bound to a known probe captured in nanopore. The binding may be direct binding or indirect binding through an intermediate molecule or molecules. At 604, the probe molecule is pulled/pushed through the nanopore so that the probe-reporter binding site is pushed against the nanopore. At 606, sequence in front of the binding site is read. At 608, the read sequence is used to determine that a reporter-target molecule has been captured and in some instances this reading can be used to determine what sample the reporter-target came from in a multi-sample experiment. The target molecule can bind to a specific site on the probe molecule and give a unique sequence. Since the identity of the target molecule is known. The target molecule can be selective released, collected, counted, and binned for further processing and/or use. In some instances, the sequence of the probe in front of the binding site is read using sequencing by synthesis with tags (see, e.g., FIGS. 2C and 2D) 606.

Figure 15:
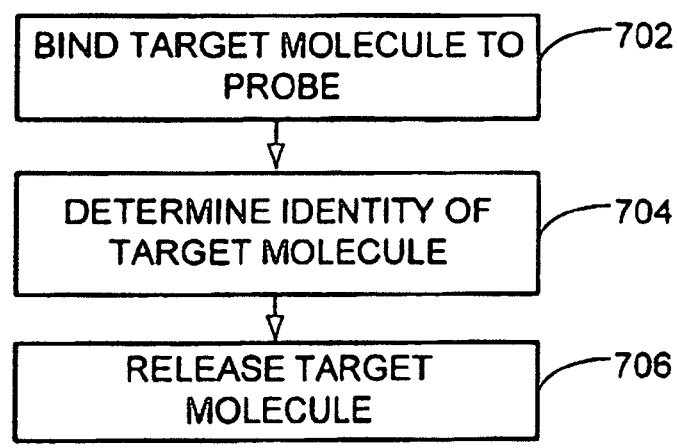
FIG. 15 is a process flow for counting, binning, collecting of target molecule using nanopore trapped probe molecule.

FIG. 15 is a process flow for counting, binning, collecting of target molecule using nanopore trapped probe molecule. At 702, target molecule is bound to a known probe molecule trapped in nanopore. At 704, the identity of the target molecule is determined based on probe sequence in front of the binding site of the reporter-target molecule on the probe. At 708, the reporter-target molecule is released from the probe to be collected, binned, and/or counted for further processing and/or use.

Figure 16:
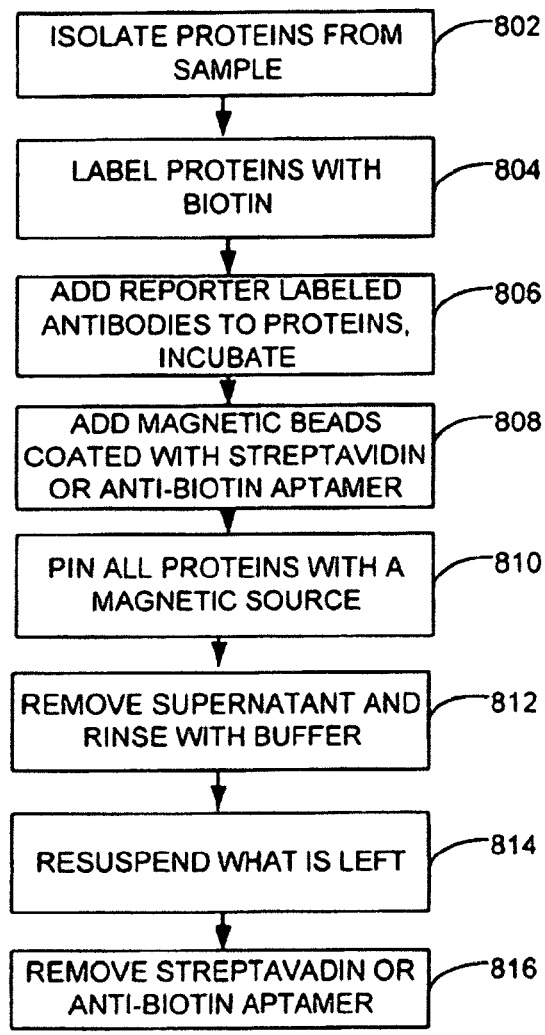
FIG. 16 is a process flow for detecting, identifying, counting, binning, and/or collecting target protein molecules using nanopore trapped probe molecule.

FIG. 16 is a process flow for detecting, identifying, counting, binning, and/or collecting target protein molecules using nanopore trapped probe molecule. At 802, proteins are isolated from sample. At 804, isolated proteins are labeled with either imino biotin, biotin, or an antiavidin RNA adptamer. At 806, reporter labeled antibody is added to the proteins and allowed to incubate and bind. At 808, all unbound antibodies and reporter DNA molecules are washed away by putting in the mixture magnetic beads coated with streptavidin or magnetic beads coated with anti-biotin RNA aptamer. At 810, you can pull all proteins to the side of your reaction tube using a magnetic source. At 812, supernatant is removed, the beads/proteins/antibody reporter DNA are rinsed with new buffer solutions a multitude of times. At 814, the sample protein molecules are released from magnetic attraction and resuspended. At 816, streptavadin/iminobiotin links can be broken by lowering the pH of the solution, or RNAase enzyme is added to destroy the antibiotin or antiavidin RNA aptamer. In some cases, 816 is captavidin, which can release molecules when the pH is changed. The result is a pool of sample proteins that are labeled with antibody and reporter molecules and no freestanding, and no non-protein bound antibodies/reporter molecules are in solution.

FIG. 17 is a process flow for detecting, identifying, counting, binning, and/or collecting target protein molecules using nanopore trapped probe molecule. At 902, proteins are isolated from sample. At 904, isolated proteins are labeled with either imino biotin, biotin, or an antiavidin RNA adptamer. At 906, reporter labeled antibody is added to the proteins and allowed to incubate and bind. At 908, all unbound antibodies and reporter DNA molecules are washed away by putting in the mixture magnetic beads coated with streptavidin or magnetic beads coated with anti-biotin RNA aptamer. At 910, you can pull all proteins to the side of your reaction tube using a magnetic source. At 912, supernatant is removed, the beads/proteins/antibody reporter DNA are rinsed with new buffer solutions a multitude of times. At 914, the sample protein molecules are released from magnetic attraction and resuspended. At 916, protease K is added to dissolve all proteins. At 918, temperature is raised to denature protease K. At 920, the sample is cooled for use on the nanopore array or stored for possible further characterization or use.

Figure 18:
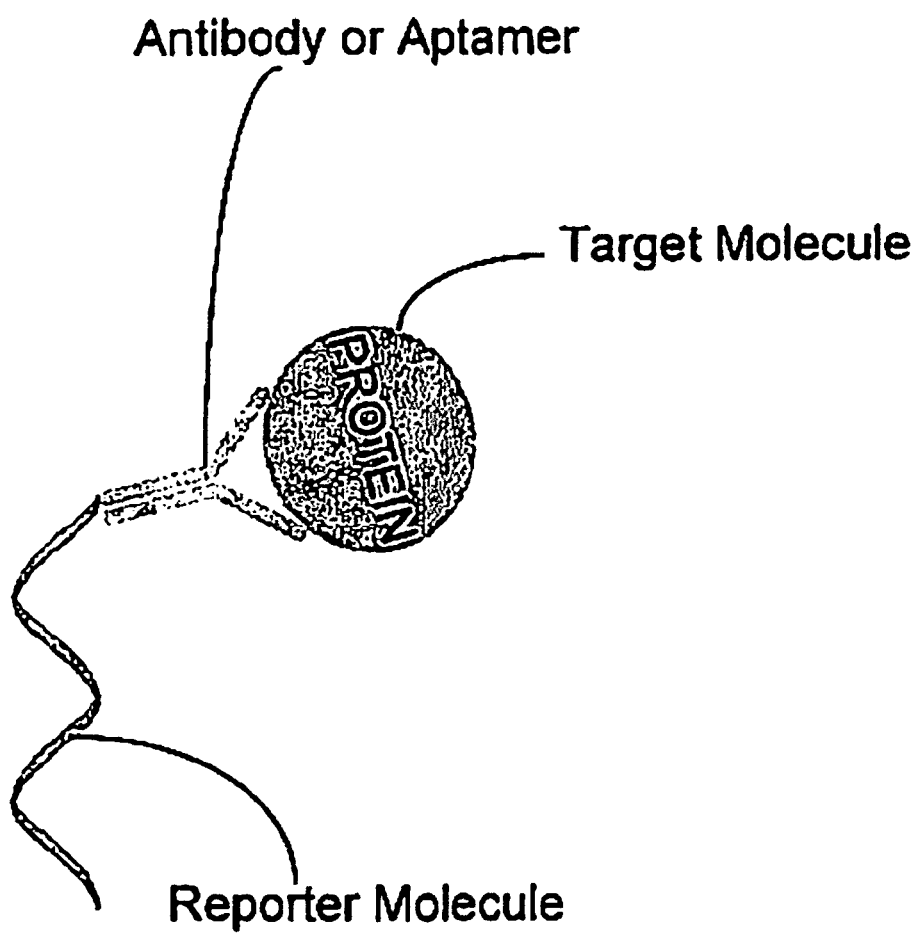
FIG. 18 illustrates the structure of a protein molecule bound to reporter labeled antibody.

FIG. 18 illustrates the structure of a protein molecule bound to reporter labeled antibody. The reporter molecule can be any molecule that can bind to the probe sequence. Example reporter molecules include DNA, RNA, cDNA, siRNA, shRNA, PNAs, GNAs, morpholinos, or any other polymer or moiety that binds to polymer probe strand.

Figure 19:
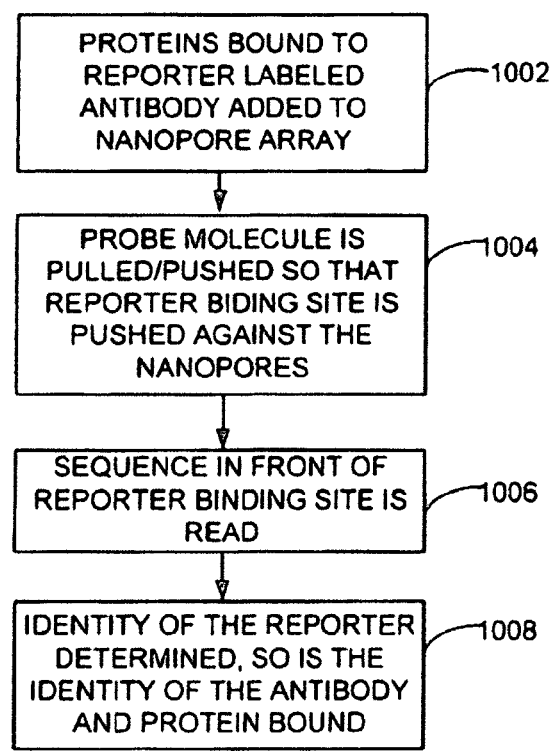
FIG. 19 is a flow process for characterizing the reporter and antibody bound target molecule (e.g., protein) using a nanopore trapped probe molecule.

FIG. 19 is a flow process for characterizing the reporter and antibody bound target molecule (e.g., protein) using a nanopore trapped probe molecule. At 1002, protein molecules bound to reporter labeled antibodies are added to nanopore array. An array of probe molecules is trapped in the nanopores of the nanopore array. The identities and location of the trapped probe molecules can be determined using techniques described above. You begin operating your nanopore arrays, pulling in probe molecules to the nanopores to be trapped and verified. At 1004, the probe molecule is pulled/pushed under for example electrical field so that the binding site of the reporter molecule is pushed against the nanopore. At 1006, the sequence in front of the reporter binding site is read. At 1008, the identity of the reporter molecule, thus the antibody bound to the reporter molecule and the protein molecule bound to the antibody can be determined based on the read probe sequence.

Figure 20:
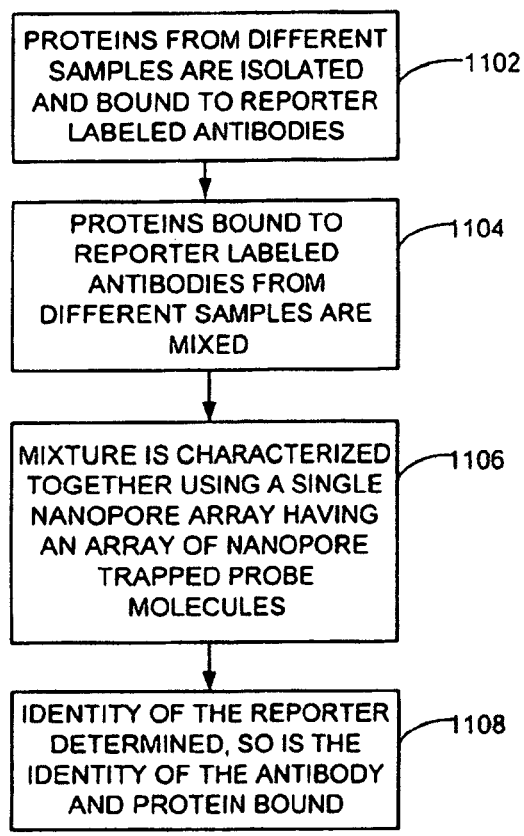
FIG. 20 is a flow process for characterizing target molecules from different samples using nanopore trapped probe molecules.

FIG. 20 is a flow process for characterizing target molecules from different samples using nanopore trapped probe molecules. Since the probe binding site of a reporter molecule is unique to the reporter molecule. If the reporter molecules for the same antibodies used for different samples are made to be different from each other, we can identify which sample the target molecule is from by looking at the signal produced when a particular reporter molecule is bound. For example, antibodies used to bind hydrogen peroxidase in sample A are labeled with reporter molecule M, antibodies for binding hydrogen peroxidase in sample B are labeled with reporter molecules N. M and N are the same except N is three nucleotides longer than M. M and N will produce different signals when they are bound to the probe molecule and when the probe sequence is read when the reporter binding site is pushed against the nanopore. The source of the proteins bound to the probe can be determined based on such signals. At 1102, proteins from different samples are isolated and bound to unique reporter labeled antibodies separately. The reporter molecules bound to a particular type of antibody are different and bound to different locations on the probe molecule for different samples. At 1104, antibody reporter-protein molecules from different samples are mixed. At 1106, antibody-reporter-protein molecules from different samples are characterized together using the same nanopore array. At 1108, the identity of the protein bound to a probe molecule trapped in nanopore can be determined from the electrical signal of the probe molecule when the probe molecule is positioned in such a way that the reporter binding site is pushed against the nanopore and the sequence in front of the reporter molecule is read. Characterizing different samples together using the same nanopore array allows superior quantitative comparison of two samples since they are subjected to the same characterization conditions. For example the number of hydrogen peroxidase from sample A and B can be counted and their ratio determined. At 1108, at the end of characterization, probe captured molecules can be selectively released, binned, counted, collected, and/or sorted for further analysis and/or use. For example, captured hydrogen peroxidase from sample A can be released from the nanopore array at the same time and collected and counted since the nanopores are individually and electrically addressable.

The target molecules can be collected and recovered at the end of characterization for further processing and/or use. Thus the techniques disclosed herein allow for real-time single molecule characterization since the characterized target molecule can be collected, counted, and isolated as the molecule is characterized.

For quantitative analysis, target molecules and target reporter molecules (whichever binds to the probe sequence) can be attached with one-time-read labels (e.g., chemical label that peels off and give a signal when the target molecule is read the first time. The one-time-read labels cannot reattach to the target molecules. The presence or absence of the signal given off when the on-time-read label is peeled off can be used to determine whether the molecule has been counted or previously characterized.

The techniques described herein can be applied to detect, count, sort, bin, and/or enrich low concentration samples, such as a few molecules at a time.

The present disclosure provides various examples for detecting molecules. In some cases, an ssDNA reporter can be attached to each protein in a solution having an unknown composition. The reporter molecule can then be pulled into a pore and stopped. A single reading can be taken identifying the protein. This method may be limited in the number of different proteins that can be identified because there is only one stop position to read.

In another example, an ssDNA reporter can be attached to each protein in a solution having unknown composition. The reporter can attach to a probe molecule that is trapped in a pore. The probe molecule may have an address region that is read either before or after hybridization with a reporter by using speed bumps. In this method, there are many more probes that can therefore be used in an array of pores. The address can allow the identification of many different strands. As an example, the probe can have 4 levels for each speed bump stop and 6 speed bump stops, giving 4096 different addresses. Using this approach, select molecules can be released from the array of nanopores and sorted, binned, and archived.

In another example, an ssDNA reporters can be attached to proteins in a solution having unknown composition. In some cases, many or all of the proteins can be isolated from the bulk supernatant. In some cases, free floating, unbound reporter molecules are washed away. The proteins may then be destroyed and/or degraded (e.g., with Protease). In some cases, this leaves only the reporter ssDNA in the reaction mix representing the original proteins that were in the original solution. These ssDNA reporters can then be placed on an array with probe ssDNA bound in the pores. In some instances, the reporters bind to the probes and the resulting stopped signal represents a catch or read of a protein. In some embodiments, the proteins no longer exist so they cannot be subsequently released from the nanopore array and sorted, binned, and archived.

In another example, the molecule in solution is not a protein. The molecule can be ssDNA for example. The binding of free DNA in solution to a trapped ssDNA probe in the pore may allow for detection of specific DNA strands and the sorting, binning, and archiving of these select strands. In some cases, the array probes are ejected from the array and collected.

Methods for detecting molecules may employ the use of speed bumps. Examples of speed bumps and uses thereof are described in U.S. Patent Publication Nos. 2012/0160681 and 2012/0160688, which are entirely incorporated herein by reference.

Figure 21:
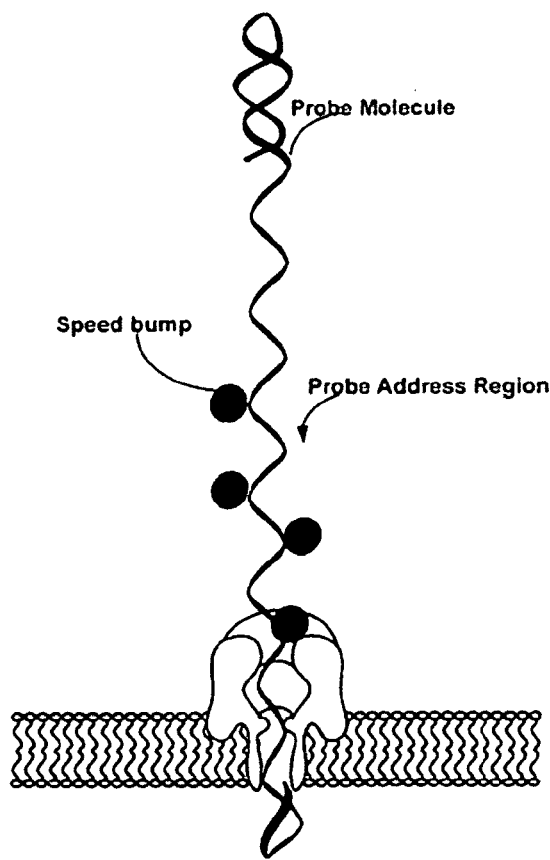
FIG. 21 illustrates binding of speed bumps to an address region of a probe molecule trapped in nanopore.

FIG. 21 illustrates binding of speed bumps to an address region of a probe molecule trapped in nanopore. The address-region-specific speed bumps can be bound to this region to allow it to be quickly identified and read using a nanopore detector. This region can be quickly identified by threading the probe molecule in a nanopore until the speed bumps are stop at the entrance of the nanopore and electrical signals are measured as the probe is stalled in the pore. The address region may be engineered so that it binds to specific types of speed bumps. For example, polynucleotides made of isodG and poly isodC in unique patterns may be engineered into the address region. Speed bumps (e.g., speed bumps made of isodG and/or isodC) that bind specifically to isodG and isodC in the address region can be positioned to allow easy reading of address information.

Figure 22:
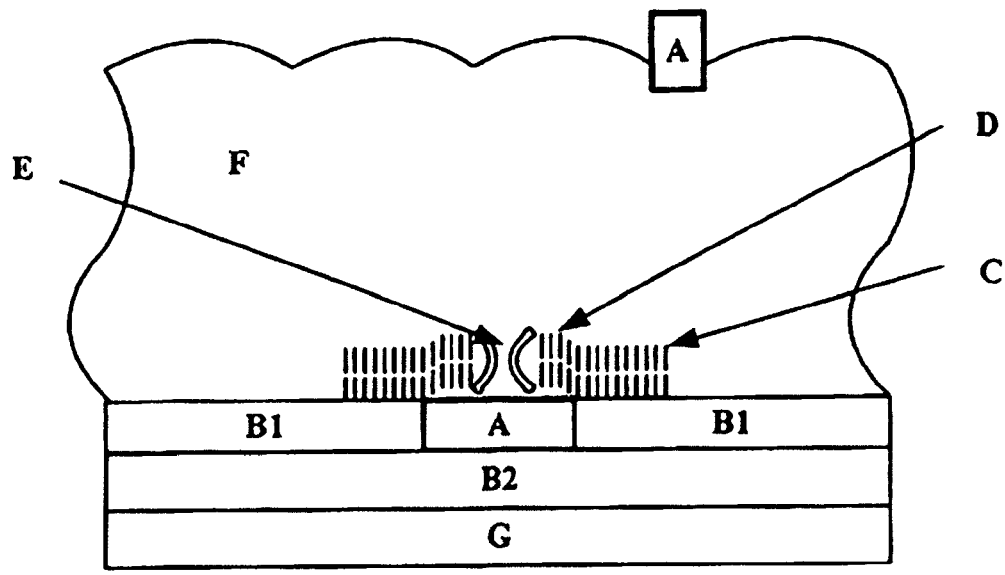
FIG. 22 illustrates an example nanopore detector.

FIG. 22 illustrates an example nanopore detector comprising electrodes A, a hydrophilic surface B which separates two purposely constructed independent wells with a small hole between them over which a bilayer C of lipid material is created. Nanopore D is inserted (e.g., by diffusion) through a conductive salt solution E. The nanopore detector of FIG. 22 may be one of a plurality of nanopore detectors in a nanopore detector array.

Figure 23:
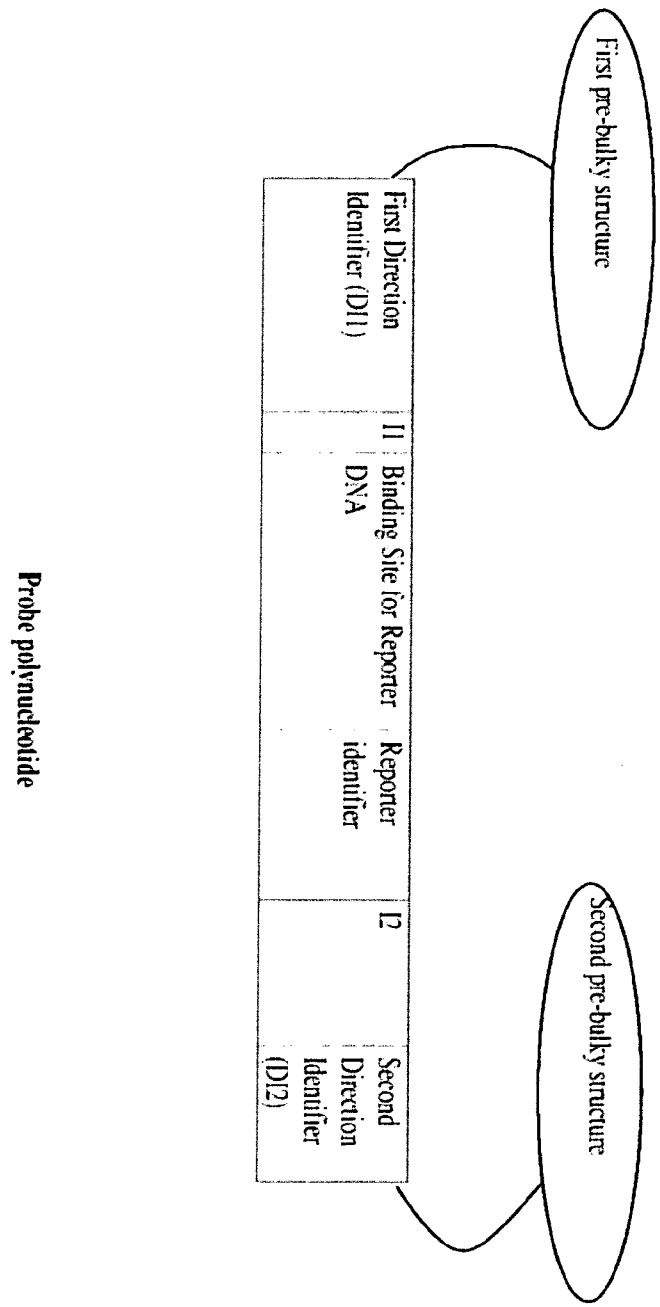
FIG. 23 shows a probe polynucleotide structure.

In another embodiment, a probe polynucleotide comprises a structure shown in FIG. 23. The probe molecule comprises a first pre-bulky structure on one end, a second pre-bulky structure on the other end, a first direction identifier (DI1), a second direction identifier (DI2), Binding Site for Reporter DNA, and reporter identifier.

The first pre-bulky structure forms a first bulky structure at a first condition. The second pre-bulky structure forms a second bulky structure at a second condition.

A pre-bulky structure, as used herein, is a structure that can form a bulky structure under certain conditions (e.g. at certain temperature, presence/absence of certain compound (s)).

A bulky structure, as used herein, is a structure that stalls the test polynucleotide molecule in a nanopore at a working condition until the working condition is changed to another condition wherein the bulky structure is converted to the pre-bulky structure or other structures that cannot stall the test polynucleotide molecule any more.

In an embodiment, a pre-bulky structure is an oligonucleotide structure in a polynucleotide molecule which can form a bulky structure under certain conditions. The pre-bulky structure can be a ss polynucleotide or a ds polynucleotide. Examples of the bulky structures include, without limitation, 2-D and 3-D structures such as polynucleotide duplex structures (RNA duplex, DNA duplex or RNA-DNA hybrid), polynucleotide hairpin structures, multi-hairpin structures and multi-arm structures.

In another embodiment the pre-bulky structure forms a bulky structure via interaction with a ligand specific to the pre-bulky structure. Examples of such pre-bulky structure/ligand pair include, without limitation, biotin/streptavidin, antigen/antibody, and carbohydrate/antibody.

In an embodiment, the bulky structure is formed from an oligonucleotide pre-bulky structure, e.g., an oligonucleotide structure formed from a pre-bulky structure in a ss test polynucleotide molecule. Examples of polynucleotide or oligonucleotide bulky structures include, without limitation, hairpin nucleic acid strands, hybridized antisense nucleic acid strands, multiple arms and three dimensional DNA or RNA molecules that are self-hybridized.

In another embodiment, the bulky structure is formed via interactions of a pre-bulky structure/ligand pair as described herein.

In one example, both the first and second pre-bulky structures are polynucleotide/oligonucleotide pre-bulky structures. The first pre-bulky structure forms the corresponding first bulky structure at a first temperature. The second pre-bulky structure forms the corresponding second bulky structure at a second temperature. And the first temperature is higher than the second temperature.

In another example, the first pre-bulky structure is a polynucleotide/oligonucleotide pre-bulky structure that forms the first bulky structure via interaction with a ligand specific to the first pre-bulky structure. In a preferred example, the formation of the first bulky structure is temperature-independent. The second pre-bulky structure is preferred to be such that the conversion between the pre-bulky structure and the corresponding bulky structure is temperature-dependent.

As shown in FIG. 23, the probe molecule further comprises direction identifiers: a first direction identifier close to the first pre-bulky structure, and a second direction identifier close to the second pre-bulky structure.

Sections DI1, and DI2 may further comprise one or more other identifiers such as reference signal identifiers, probe source identifiers, and probe identifiers.

Sections I1 and I2 in FIG. 23 can comprise one or more identifiers as described herein.

In an embodiment, a method of immobilizing a target that forms a complex/compound with a reporter molecule (reporter/target) comprises:

A1) preparing a probe polynucleotide, wherein the polynucleotide comprises a structure shown in FIG. 23 as described herein and the reporter molecule can bind to the Binding Site for Reporter molecule;

(B1) forming a first bulky structure (BS1) from the first pre-bulky structure at a first condition, (B2) applying an electric potential to flow the ss probe polynucleotide through a nanopore of a nanopore detector, (B3) forming a second bulky structure (BS2) from the second pre-bulky structure at a second condition, (B4) in some cases, applying another electric potential to reverse the flow of the ss test polynucleotide until the ss test polynucleotide is stopped by BS2 before the constriction area of the nanopore, (B5) in some cases, identifying identifiers of the probe polynucleotide (e.g. the first direction identifier, the second direction identifier, probe identifier, reference signal identifiers, and probe source identifiers) to confirm the proper formation(s) of the bulky structure(s) and to identify the probe polynucleotide, the latter is important when there are more than one nanopores in a nanopore array, wherein each nanopore is addressable, by identifying the probe polynucleotide, a connection between the addressable nanopore and the target is established, (B6) contacting the ss probe polynucleotide with reporter/target to form a ss probe polynucleotide complex comprising a reporter molecule-probe polynucleotide segment;

(B7) applying another electric potential to flow the probe polynucleotide complex through the nanopore until the reporter molecule-probe polynucleotide segment is stopped before a constriction area of the nanopore, (B8) obtaining a first set of electrical signals when the reporter molecule-probe polynucleotide segment is stalled inside the nanopore for a dwelling time, (B9) determining whether the reporter molecule is immobilized by identifying the structure that is in front of the reporter molecule-probe polynucleotide segment in the flow direction of the probe polynucleotide, when the reporter molecule forms a compound/complex with the target, the target is immobilized when the reporter molecule is immobilized, and (B10) in some cases, identifying one or more identifiers in I2 and LI (e.g. probe identifier, reference signal identifiers, and probe source identifiers).

The method described herein can be used to detect and/or quantify the reporter molecule and the target attached to the reporter molecule at a molecular level.

In some embodiments, the reporter molecule is the target.

In some embodiments, the method can be further applied to immobilizing multiple reporter/target molecules using an array of nanopores, wherein the method described herein is applied to individual probe polynucleotide, individual reporter/target molecule and each individually addressable nanopore. After the reporter/target molecules are immobilized and identified, the reporter/target molecules are detected/quantified at a molecular level. Furthermore, the reporter/target molecules immobilized can be further concentrated/sorted/purified by controlling the condition of the individual nanopores (e.g. electric potential thereof) wherein the probe polynucleotide is trapped.

This invention can be used on massively parallel, individually controllable, electrode/nanopore sensors. An array of these electrode/nanopore sensors containing more than 1,000, 10,000, 100,000, or millions of electrode/nanopore sensors can be fabricated on an essentially planar semiconductor surface. Control circuitry can be incorporated into the semiconductor to create individually controllable and individually readable electrode/nanopore sensors and these sensors can be used to read any polymer that will fit into the nanopore; including all forms of DNA and RNA including but not limited to methylated DNA.

Methods for detecting molecules may, in some cases, employ protein unfolding and flow-through a nanopore. See, e.g., J. Nivala, D. B. Marks and M. Akeson, "Unfoldase-mediated protein translocation through an α-hemolysin nanopore," Nature Biotechnology, 2013, DOI: 10.1038/nbt.2503, which is entirely incorporated herein by reference. An unfolded protein may be threaded through a nanopore of the present disclosure. An amino acid sequence of the unfolded protein may be generated upon flowing the protein through the nanopore.

EXAMPLES

The examples below are illustrative of various embodiments of the present disclosure and non-limiting.

Example 1. Forming Bilayers and Inserting Pores

Forming bilayers and inserting pores on the flow cell using a manual syringe setup and a syringe pump setup results in high bilayer and single hemolysin pore yield. Bilayers are formed on both setups via flowing 1M or 0.3M KCl solution and air bubbles across a lipid covered chip surface and applying electrical stimuli. Two hemolysin application methods result in high single pore yield. One method involves the following steps: (1) premix hemolysin with lipid in decane, (2) flow the hemolysin-lipid mixture over the chip surface and incubate for a few minutes, (3) form bilayers, and (4) apply an electrical stimulus to electroporate pores into bilayers. The second method involves the following steps: (1) flow lipid in decane over the chip surface, (2) form bilayers, (3) flow hemolysin across the chip surface, (4) immediately flow KCl wash, and (5) apply an electrical stimulus to electroporate pores into bilayers. During the electroporation step in both application methods, the chip can be heated up to make bilayers more fluidic for hemolysin insertion. The temperature is reduced to room temp or lower either during or after the electroporation step to increase longevity of pore life.

Example 2. Flow Cell Configuration

Figure 24:
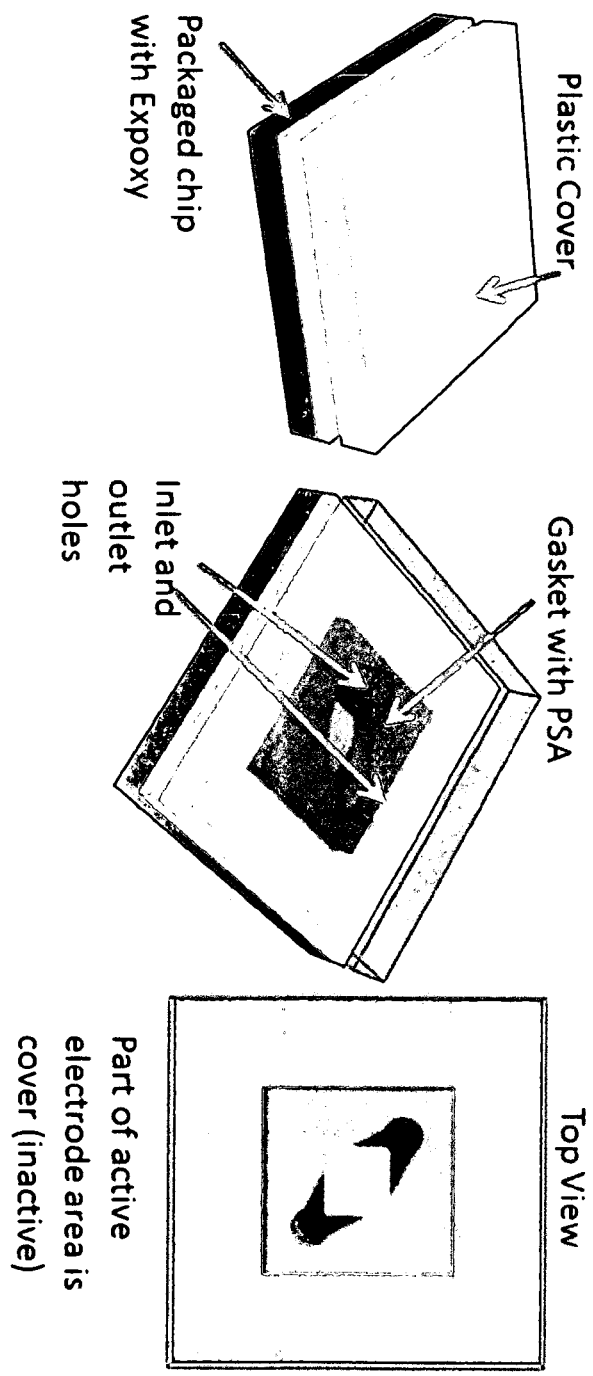
FIG. 24 shows an example flowcell configuration.
Figure 25:
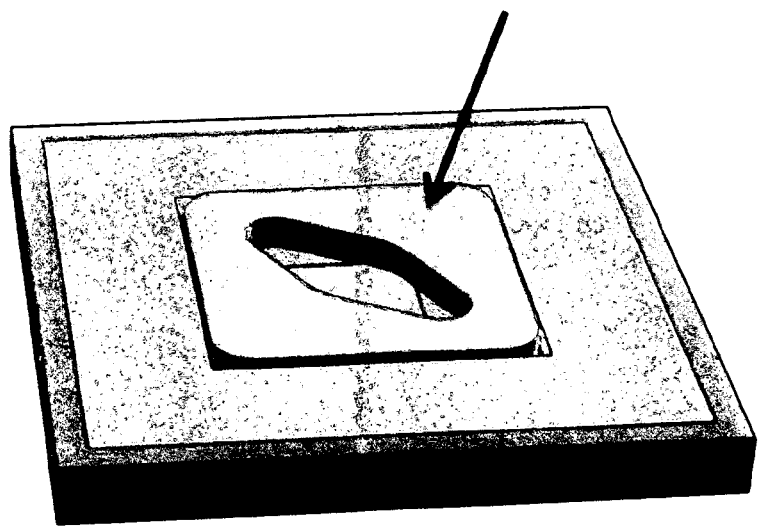
FIG. 25 shows an example of a packaged chip.

With reference to FIG. 24 and FIG. 25, the flow cell is assembled on the chip package by directly placing a gasket on top of the semiconductor chip. The gasket thickness varies from 50 um to 500 um. The gasket can be composed of plastic with pressure sensitive adhesives on one or both sides, silicone membrane, or flexible elastomer, such as EPDM. The gasket can be made into any shape. A rigid plastic top (e.g., made from PMMA) is positioned on top of the gasket (e.g., made from PSA laminated PMMA) and can be sealed to the gasket through the pressure sensitive adhesive or by a locking mechanism that applies a compression force to the gasket. The top has single or multiple inlet and outlet ports used to flow reagents and air through the flow cell.

In some instances the overall gasket size is 4 mm by 4 mm square. In some cases, the flowcell volume is about 1.5 ul for the 500 um thick gasket configuration. About 15 to 20 electrodes are covered under the gasket in some embodiments.

Example 3. Fluidic Syringe Pump

Figure 26:
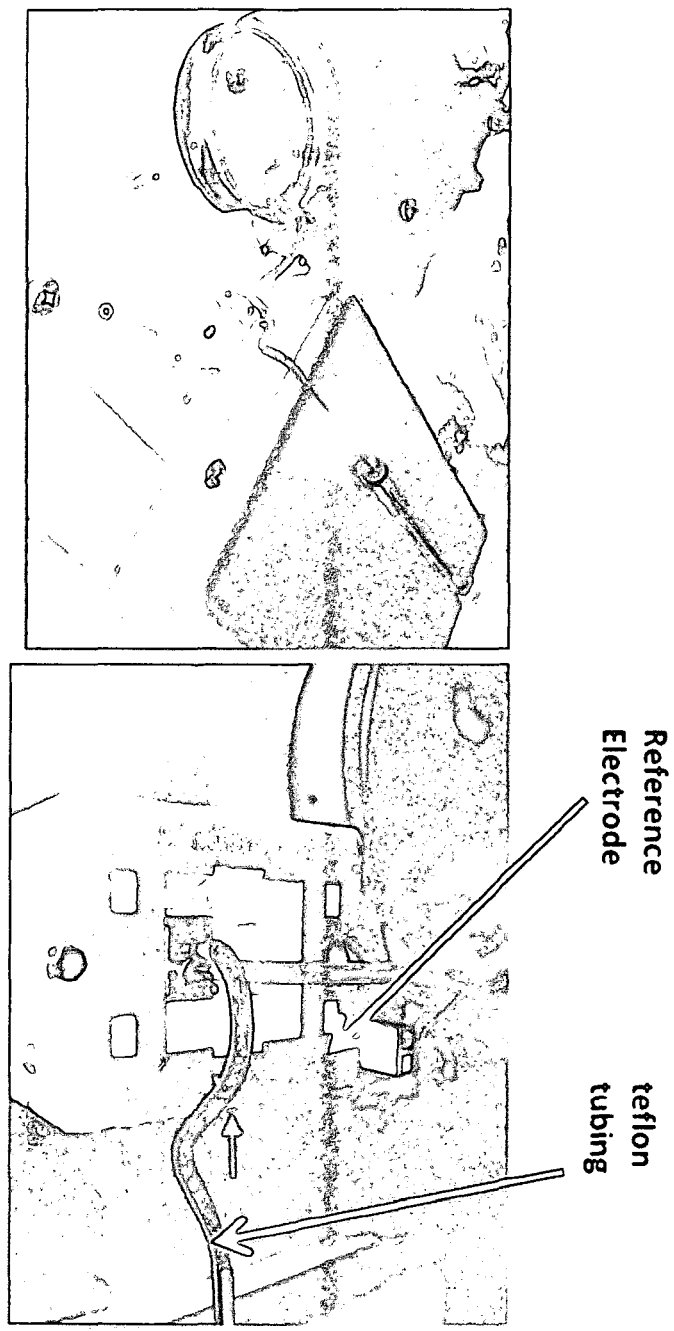
FIG. 26 shows an example of a syringe pump setup.
Figure 27:
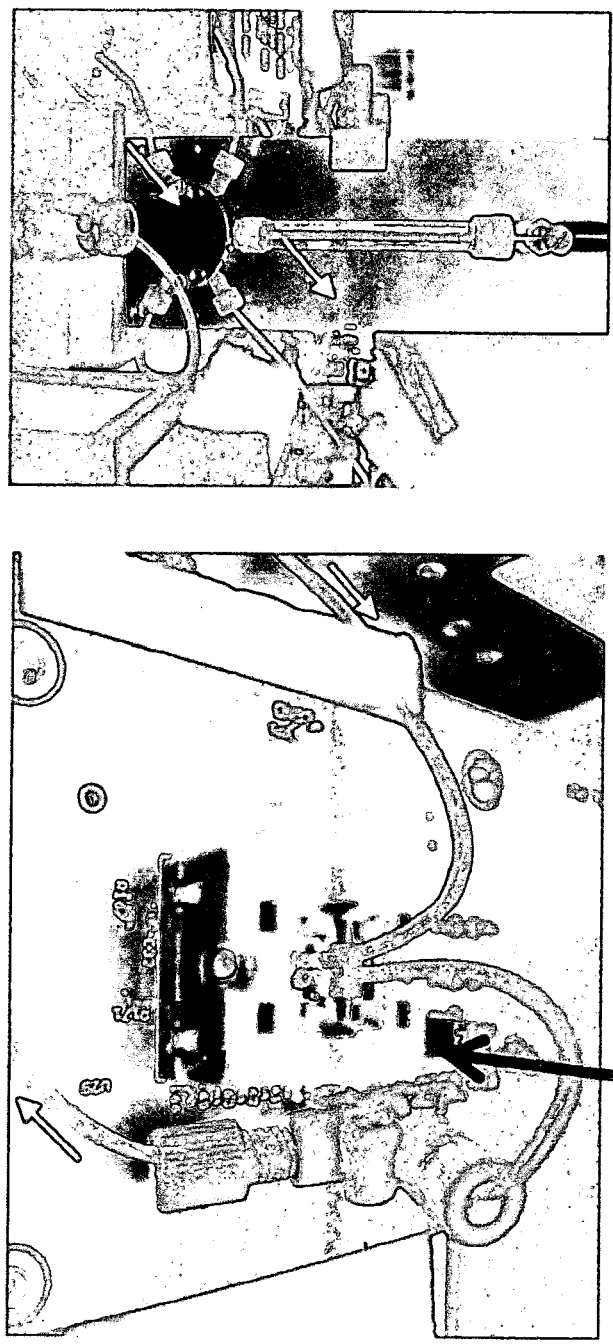
FIG. 27 shows an example of a manual syringe setup.

With reference to FIG. 26 and FIG. 27, the rate of air and liquid flow across the chip is controlled via a fluidic pump and injection valves. The flow rate generated by the pump varies from 0.01 ul/s to greater than 100 ul/s. The fluidic controller has a multi-port selection valve with a buffer inlet port, an outlet port, and lipid/hemo injection ports.

One laboratory fluidic pump example is the Kloehn Versapump 6 (V6) syringe pump. The pump has a face mount 5 port injection valve. During the experiment, different samples are pulled into the syringe and pushed out through the outlet port, flowing into the flow cell. The flow rate is controlled by a stepper motor in the pump.

Example 4. Flow Protocol on the Syringe Pump

The example achieves over 90% lipid coverage and 30% hemolysin pore insertion. Injection of a mixture of DPhPC and Hemolysin across the chip surface also achieved over 50% pore insertion yield.

Bilayer Preparation:
(a) Pull 100 ul of 1M KCl and flow across the flowcell system at 10 ul/s flow rate.
(b) Condition the chip electrodes by applying potential steps using a Ag/AgCl reference electrode.
(c) Inject 40 ul of 7.5 mg/ml DPhPC in decane across the chip at 1 ul/s flow rate.
(d) Inject 20 ul of air bubble across the chip.
(e) Inject 100 ul of KCl across the chip at 1 ul/s flow rate.

Hemolysin Pore Insertion:
(a) Inject 50 ul of Hemolysin solution across the chip surface at 1 ul/s flow rate.
(b) Flow 100 ul of KCl solution across the chip surface.
(c) Modulate electrode potential for pore insertion either immediately after step a) before step b) or after step b).

Example 5. Flow Protocol Using a Manual Syringe

Bilayer Preparation:
(a) Pull 100 ul of 1M KCl and flow across the flowcell system.
(b) Condition the chip electrodes by applying potential steps using a Ag/AgCl reference electrode.
(c) Flow through a hemolysin-lipid mix containing 7.2 mg/ml DPhPC in decane and 5 ug/ml Hemolysin, followed by 120 ul KCl
(d) Apply a series of negative electric pulses to remove lipid coverings.
(e) Flow through 20 uL KCl and 20 ul bubble two times, followed by 120 ul KCl. Repeat steps d and e approximately 4 times or until at least 80% of electrodes show currents higher than 300 pA while applying electric pulses.
(f) Flow through 20 uL KCl and 20 ul bubble two times, followed by 120 ul KCl to recover electrodes with bilayers.

Hemolysin Pore Insertion:
(a) Increase chip temperature to approximately 55 degree Celsius.
(b) Apply electric pulses to electroporate pores into bilayers.

The above experimental procedure results in 151 to 50 singles pore yield (approximately 60% to 20% hemolysin pore insertion, respectively).

The temperature of the chip can be modulated during the experiment. The reference electrode setup will also be adjusted to potentially include Ag/AgCl ink painted on the flow cell.

Example 6. Materials and Setup

Reagents: 0.3M KCl 20 mM Hepes pH 7
Hemolysin:
5 ug/ml hemo in 7.2 mg/ml DPhPC in decane & 2.5% glycerol
20 ug/ml hemo in 7.2 mg/ml DPhPC in decane & 2.5% glycerol DNA:
30 uM 30T DNA w/7.5 uM Strepavidin
30 uM 30T DNA w/7.5 uM Strepavidin and 0.83% glycerol Chips:
Rev 2 deep well large cap
Rev 1 deep well large cap Example 7. Bilayer Forming Protocol 1. Flow through 20 uL 7.5 mg/ml DPhPC in decane followed by 120 uL KCl
2. Run bilayerpop3b which applies a series of negative electric pulses ranging from −250 mV to −1V with a 300 pA deactivation current
3. Wash chip with 2*(20 uL KCl, 20 uL bubble) and 120 uL KCl.
4. bilayerpop3b
5. Repeat step 3 & 4 until at least 80% of cells deactivate between −400 mV and −700 mV pulse.
   a. About 4 to 8 repeats
6. Recover cells with 2*(20 uL KCl, 20 uL bubble) and 120 uL KCl.

Example 8. Pore Insertion Protocol

Method 1: mix hemo with lipid at start of experiment
1. After forming bilayers, set hand warmers on top of flow cell.
2. Electroporate pores into bilayers (getpore12b)

Method 2: flow hemo over bilayers followed with a wash-first electrodeporation:
1. After forming bilayers, flow 20 ul 100 ug/mlhemo in 0.3M KCl & 5% glycerol through flow cell
2. Wash with 20 ul bubble and 80 uL KCl
3. Electroporate pores into bilayers (getpore12b) with hand warmers on top of flow cell.

Example 9. Bilayer Formation and Pop Automated with Pump

Figure 28:
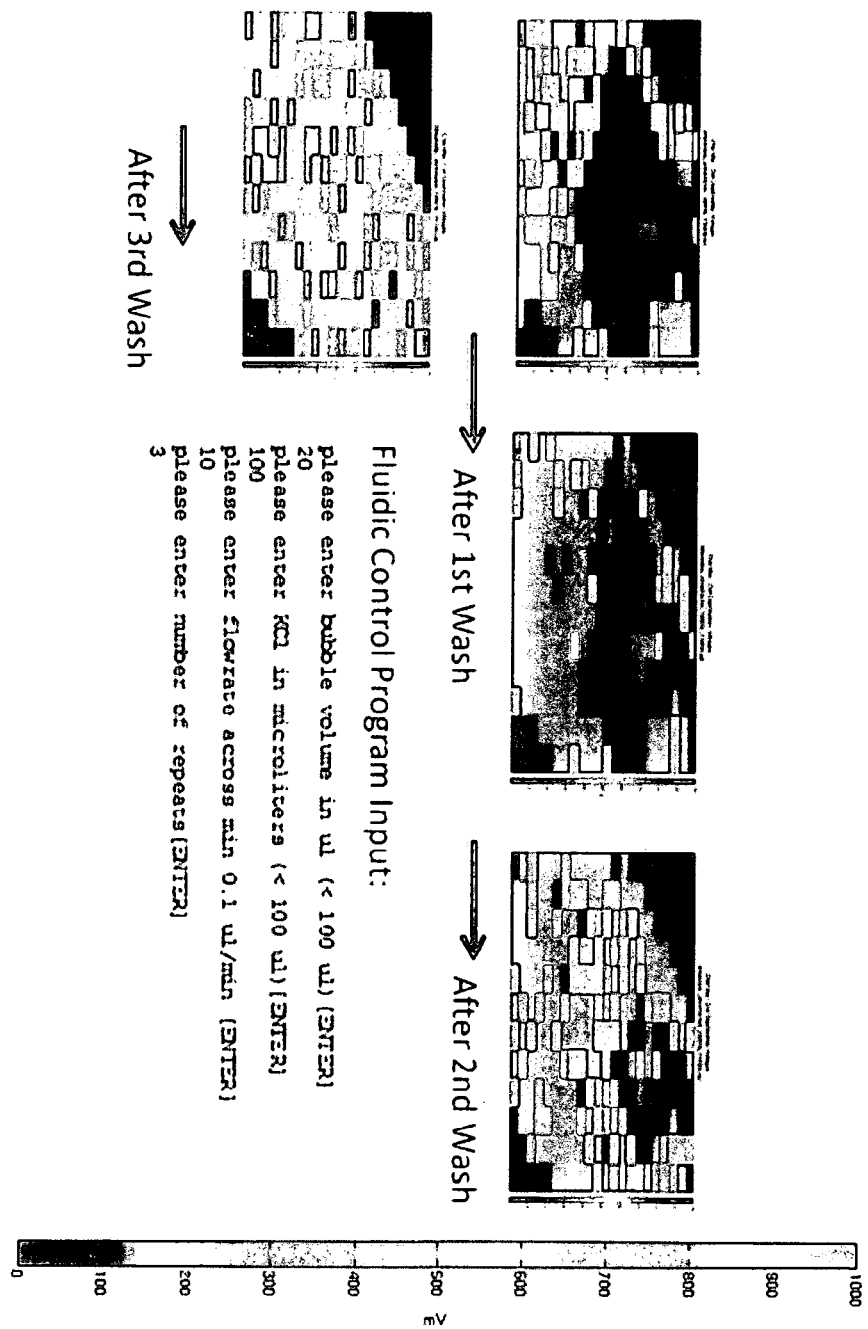
FIG. 28 shows an example of bilayer formation and pop automated with a pump.

FIG. 28 shows bilayer pop voltage vs. cell location under repeated bilayer generation wash conditions. Automated bubble and KCl washing protocol allow consistent bilayer formation. Table 1 shows bilayer formation and pop yield under various conditions (e.g., with hemolysin and lipid or without hemolysin).

TABLE 1

| Bilayer formation and pop | | |
|---|---|---|
| Chip ID | % Covered | % Pop |
| 120830_CC 01-1 | 99% | 76% |
| 120824_CC 06-1 | 94% | 59% |
| 120801_CC 01-1 | 92% | 81% |
| 120803_MT 01-1 | 73% | 51% |
| 120802_CC - 01-1 | 87% | 93% |
| 120731_MT 01-1 | 100% | 89% |
| 120803_MT 01-1 | 73% | 51% |

Example 10. Applied Waveform

Figure 29:
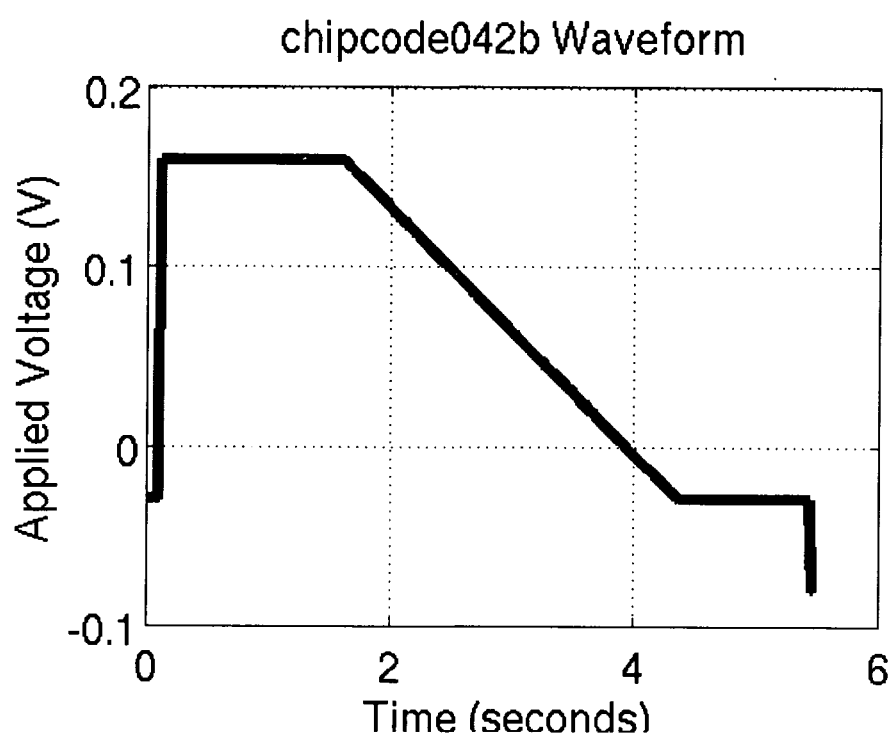
FIG. 29 shows an example of an applied waveform.

FIG. 29 shows an example of an applied waveform of open channel and DNA capture data. The waveform is entitled chipcode042b and has applied voltage on the vertical axis ranging from −0.1 to 0.2 volts. Time is displayed on the horizontal axis and ranges from 0 to 6 seconds. The trap waveform is followed by a −50 mV recharge for 33 seconds.

Example 11. Open Channel Data

Method 1 of Example 8 is used to conduct various protocols. The results of the protocols are provided in FIGS. 30-32.

Figure 30:
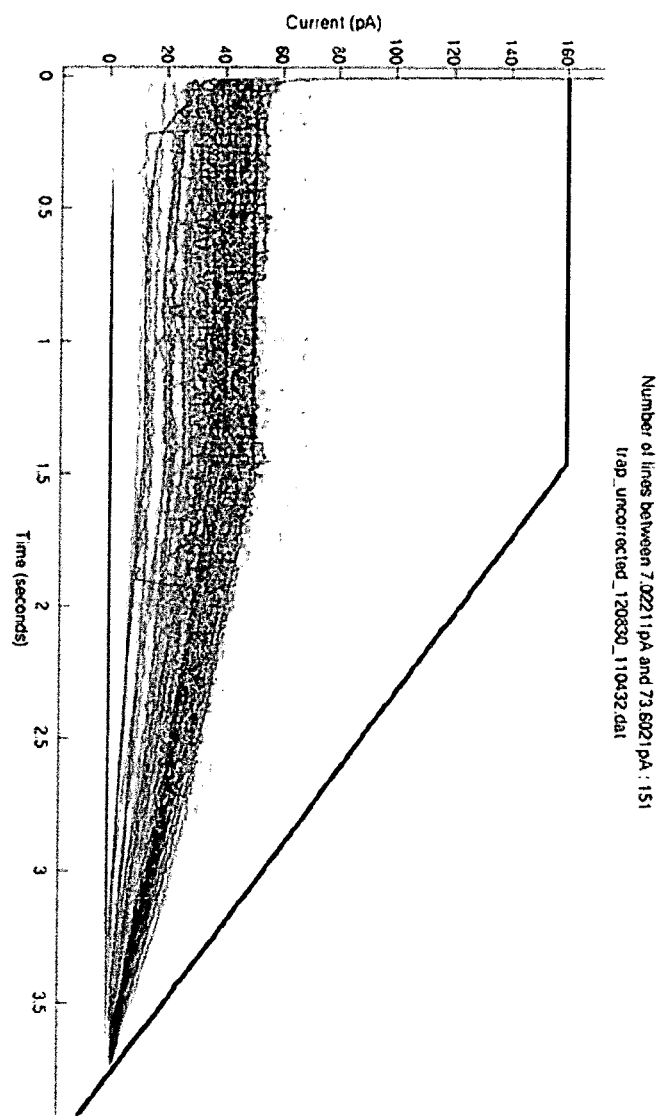
FIG. 30 shows an example of current versus time for an open channel.

FIG. 30 shows a plot of current on the vertical axis ranging from 0 to 160 pA and time on the horizontal axis ranging from 0 to 4 seconds. There are 151 lines between 7.02211 and 73.6021 pA. The protocol is Method 1 of Example 8.

Figure 31:
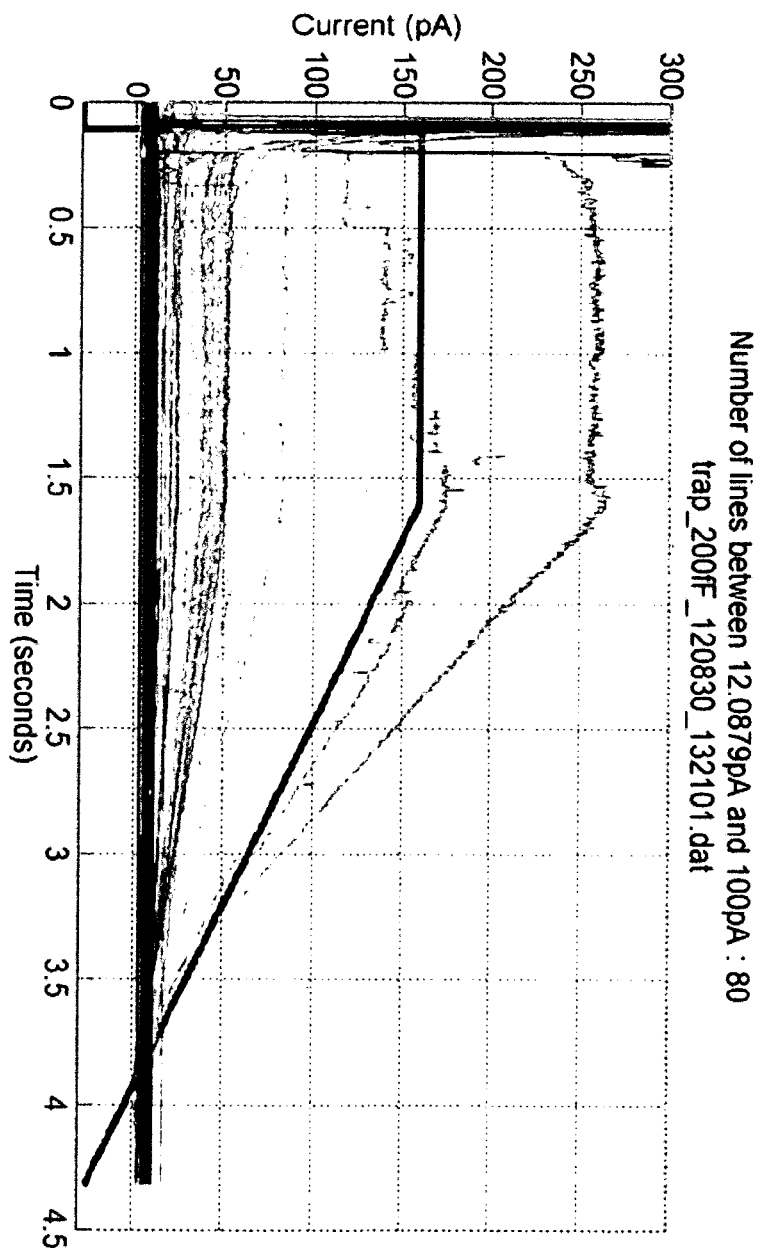
FIG. 31 shows an example of current versus time for an open channel.

FIG. 31 shows a plot of current on the vertical axis ranging from 0 to 300 pA and time on the horizontal axis ranging from 0 to 4.5 seconds. There are 80 lines between 12.0879 and 100 pA. The graph depicts data collected when using a syringe pump. The protocol is Method 1 of Example 8.

Figure 32:
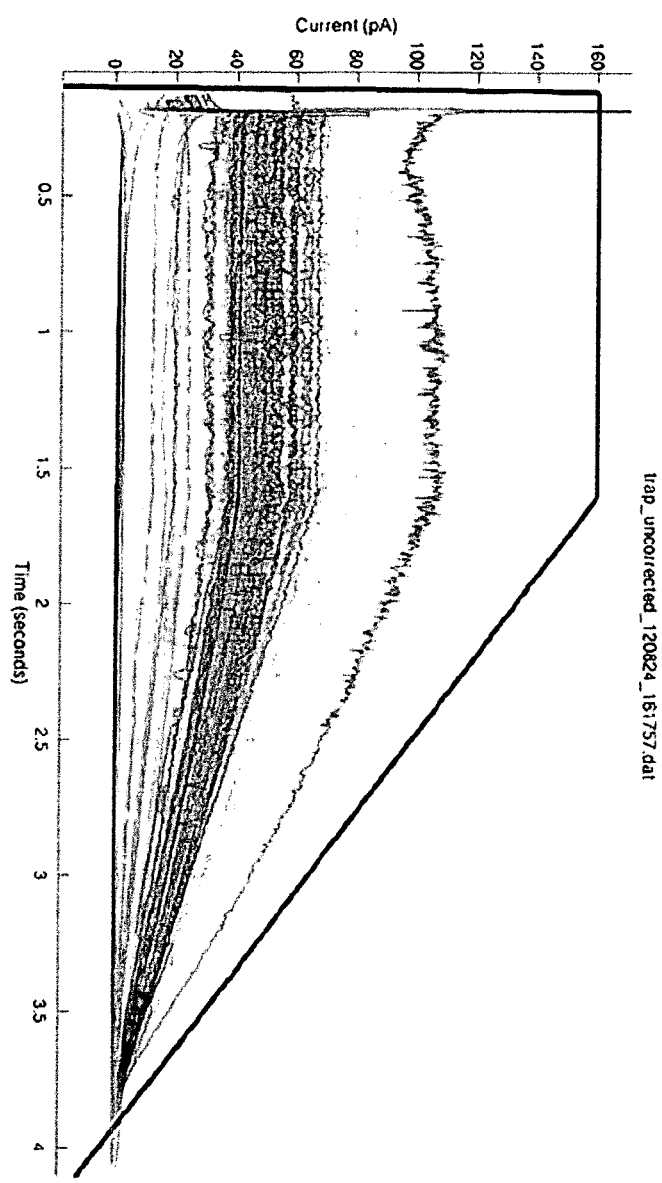
FIG. 32 shows an example of current versus time for an open channel.

FIG. 32 shows a plot of current on the vertical axis ranging from 0 to 160 pA and time on the horizontal axis ranging from 0 to 4 seconds. There are 117 lines between 26.2679 and 75.6827 pA. The protocol is Method 2 of Example 8.

Table 2 shows a summary of open channel data.

TABLE 2

Open channel data

| Experiment | Hemo Insertion Method | Pore Count |
| --- | --- | --- |
| 01-1_120830 | Mix hemo and lipid | 151 |
| 02-1_120830 | Mix hemo and lipid | 67 |
| 01-1_120829 | Mix hemo and lipid | 135 |
| 02-1_120829 | Mix hemo and lipid | 80 |
| 01-1_120828 | Mix hemo and lipid | 50 |
| 01-1_120823 | Mix hemo and lipid | 70 |
| 02-1_120823 | Mix hemo and lipid | 56 |
| 04-1_120824 | Flow hemo over bilayer | 46 |
| 06-1_120824 | Flow hemo over bilayer | 117 |
| 07-1_120824 | Flow hemo over bilayer | 85 |

Example 12. DNA Capture

Method 1 of Example 8 is used to conduct various protocols. The results of the protocols are provided in FIGS. 33-37.

Figure 33:
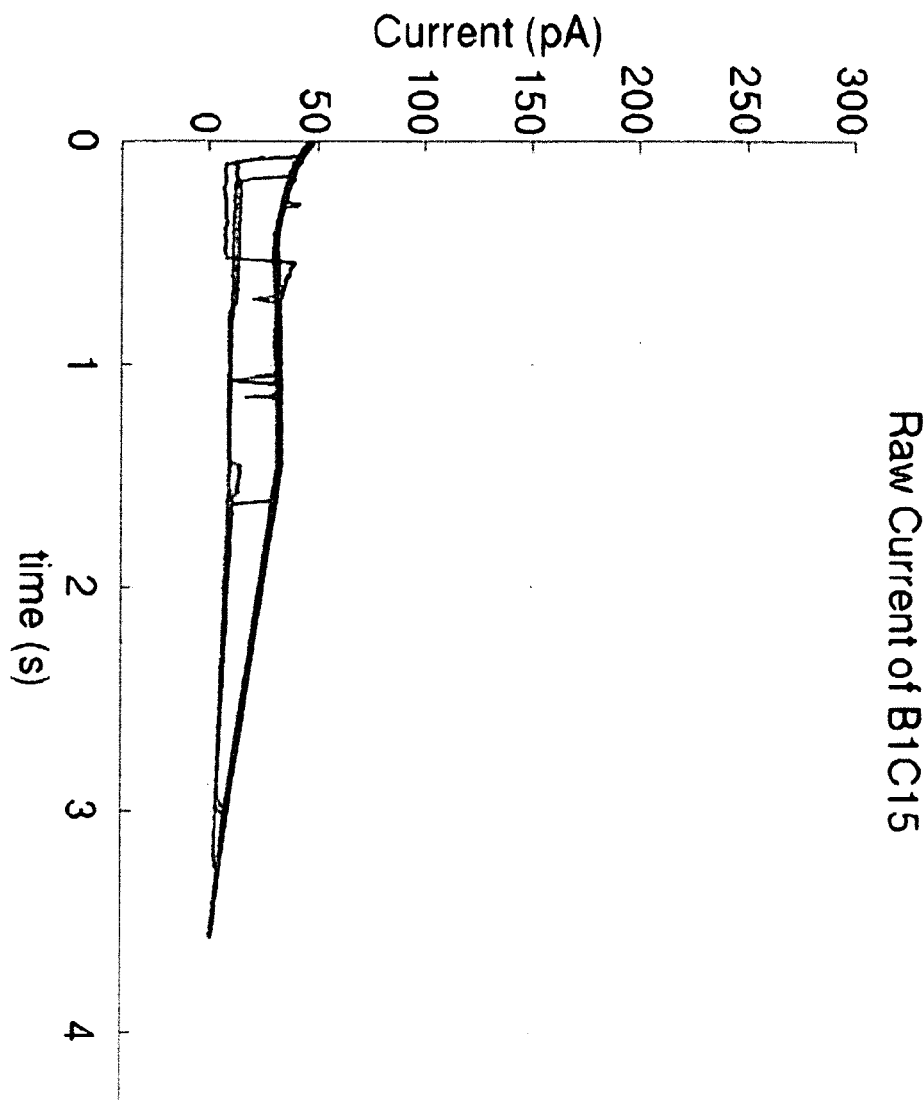
FIG. 33 shows an example of current versus time for deoxyribonucleic acid (DNA) capture.

FIG. 33 shows a plot of current on the vertical axis ranging from 0 to 300 pA and time on the horizontal axis ranging from 0 to 4 seconds. The protocol is Method 1 of Example 8 and at 160 mV.

Figure 34:
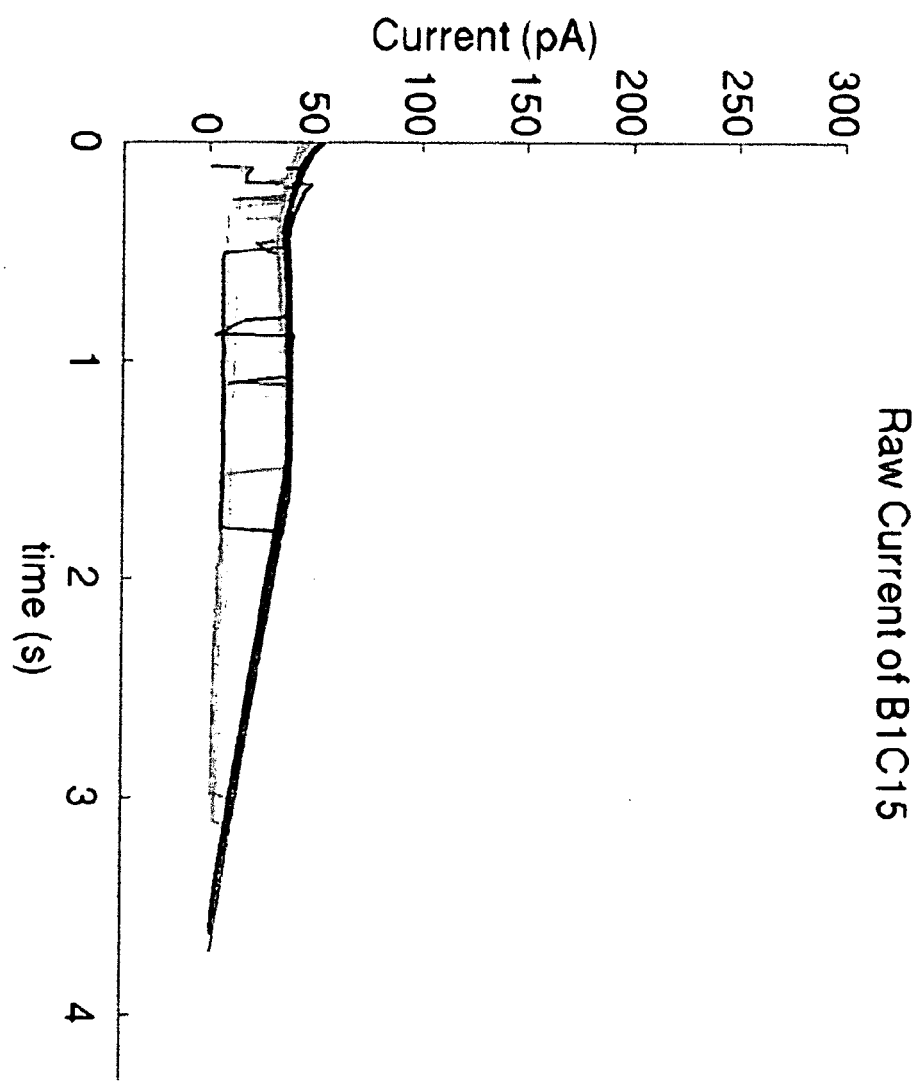
FIG. 34 shows an example of current versus time for DNA capture.

FIG. 34 shows a plot of current on the vertical axis ranging from 0 to 300 pA and time on the horizontal axis ranging from 0 to 4 seconds. The protocol is Method 1 of Example 8 and at 80 mV.

Figure 35:
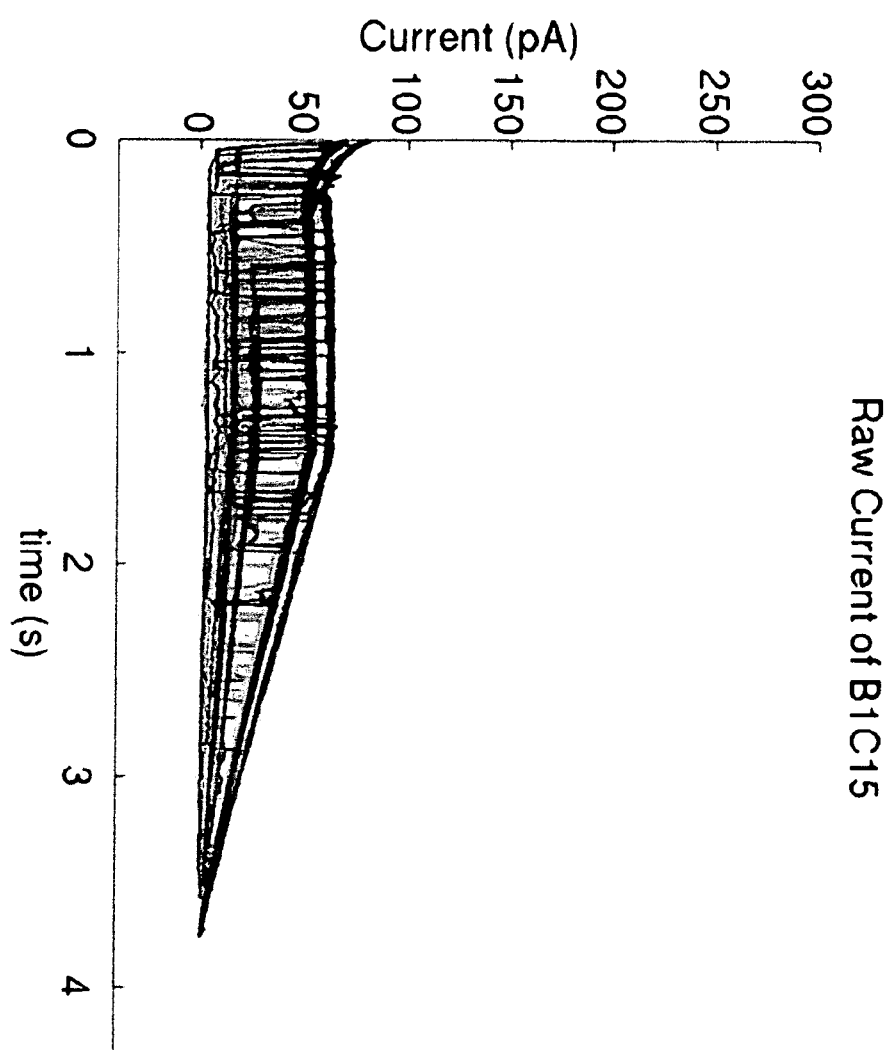
FIG. 35 shows an example of current versus time for DNA capture.

FIG. 35 shows a plot of current on the vertical axis ranging from 0 to 300 pA and time on the horizontal axis ranging from 0 to 4 seconds. The protocol is Method 1 of Example 8 and at 220 mV. In some embodiments, increasing voltage increases the capture rate. Increasing the voltage does not necessarily increase DNA catches. In some cases (e.g., about 50% of instances) adding DNA breaks the bilayer and/or knocks the pore out of the bilayer.

Figure 36:
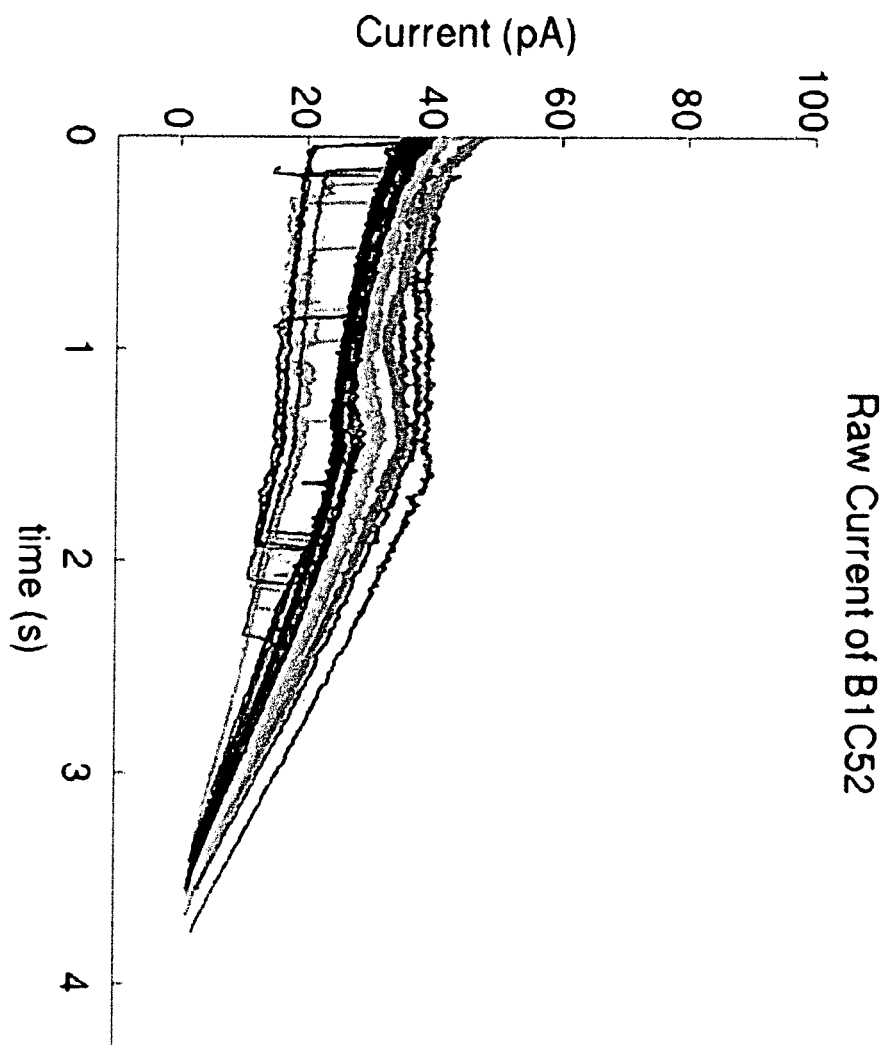
FIG. 36 shows an example of current versus time for DNA capture.

FIG. 36 shows a plot of current on the vertical axis ranging from 0 to 100 pA and time on the horizontal axis ranging from 0 to 4 seconds. The protocol is Method 2 of Example 8. The capture rate is 30T DNA at 0.3M KCl on the flow cell using a 160 mV capture voltage.

Figure 37:
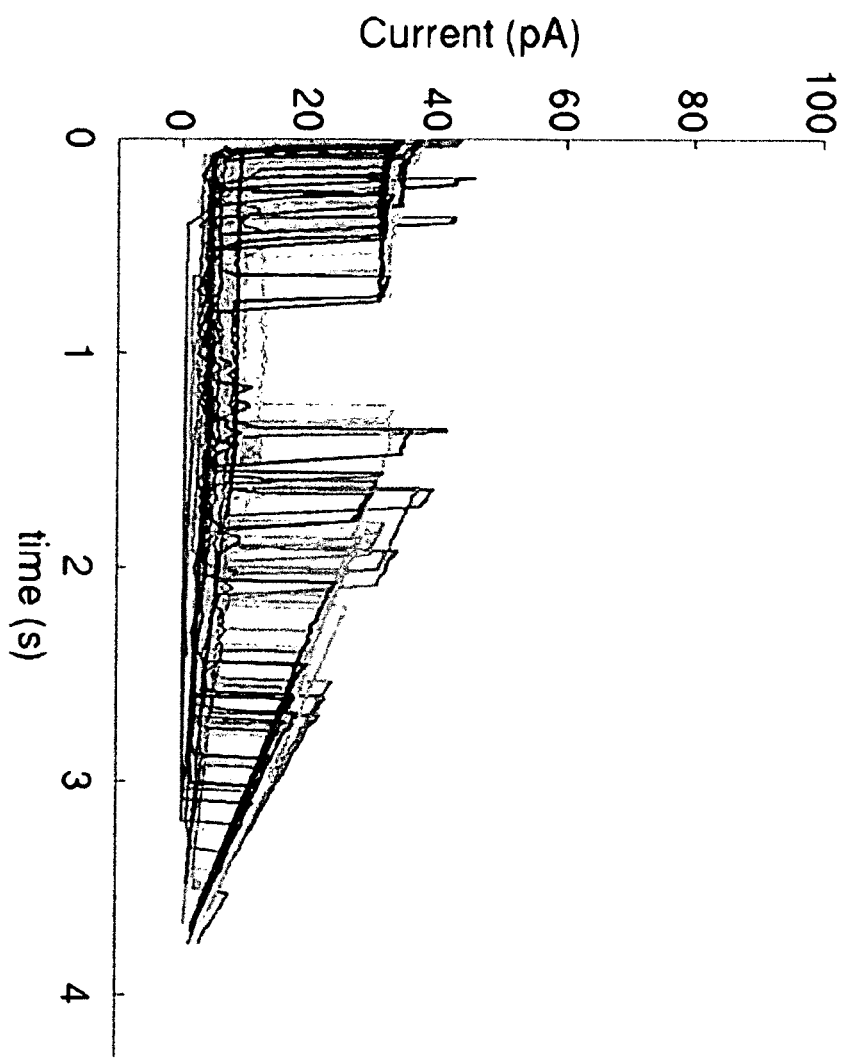
FIG. 37 shows an example of current versus time for DNA capture.

FIG. 37 shows a plot of current on the vertical axis ranging from 0 to 100 pA and time on the horizontal axis ranging from 0 to 4 seconds. The protocol is Method 2 of Example 8 with 0.3M KCl and 30 uM 30T DNA with 7.5 uM streptavidin.

Example 13. DNA Capture

Figure 38:
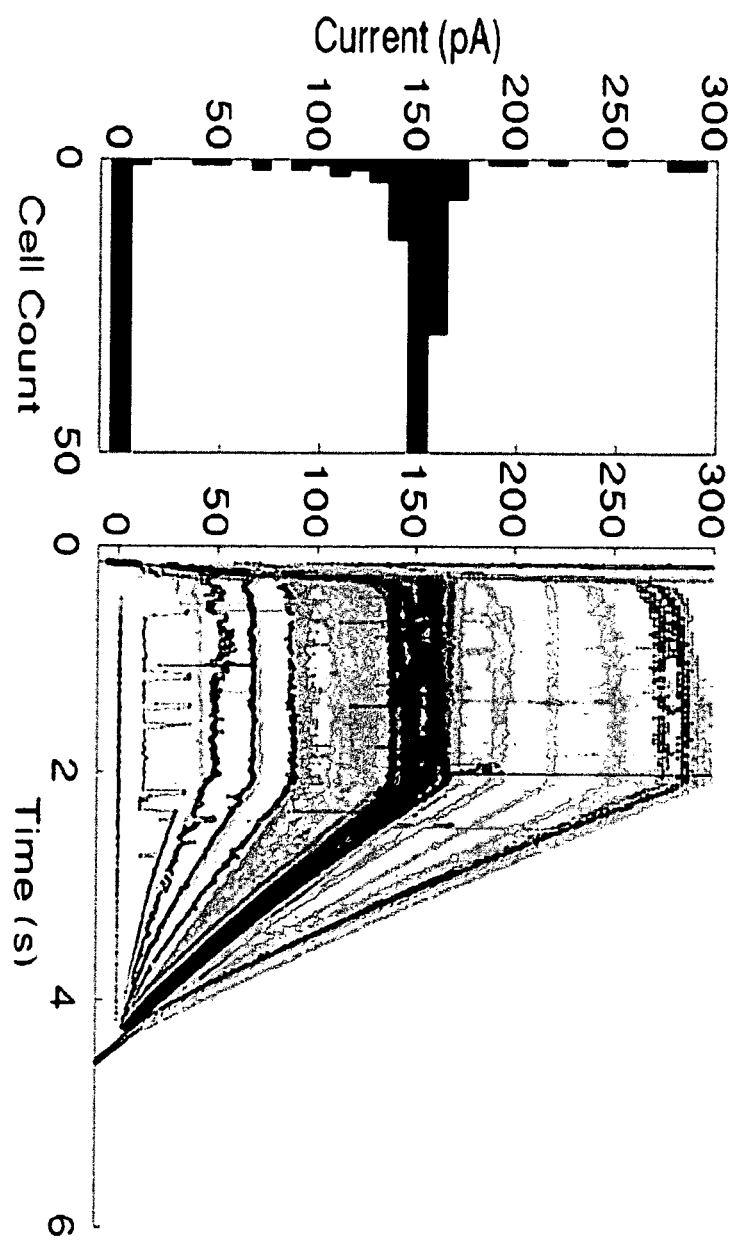
FIG. 38 shows an example of current versus time for pores after bilayer formation.

FIG. 38 shows a plot of current versus time or cell count for pores after bilayer formation (e.g., following an automated protocol). The pore formation conditions are 1M KCl, pH 7.5, room temperature, 15 mg/mL DPhPC lipid in decane and 20 ug/mL hemolysin in pH 7.5 water.

It should be understood from the foregoing that, while particular implementations have been illustrated and described, various modifications can be made thereto and are contemplated herein. It is also not intended that the invention be limited by the specific examples provided within the specification. While the invention has been described with reference to the aforementioned specification, the descriptions and illustrations of the preferable embodiments herein are not meant to be construed in a limiting sense. Furthermore, it shall be understood that all aspects of the invention are not limited to the specific depictions, configurations or relative proportions set forth herein which depend upon a variety of conditions and variables. Various modifications in form and detail of the embodiments of the invention will be apparent to a person skilled in the art. It is therefore contemplated that the invention shall also cover any such modifications, variations and equivalents. It is intended that the following claims define the scope of the invention and that methods and structures within the scope of these claims and their equivalents be covered thereby.

What is claimed is:

1. A method for forming a lipid bilayer for use in a nanopore sensor, comprising:
   (a) directing an electrically conductive buffer solution in a flow channel comprising an electrode having a lipid material layer dried down thereon, wherein said lipid material layer comprises one or more lipids, and is capable of forming the lipid bilayer;
      (i) directing a bubble through said flow channel and bringing said bubble in contact with said lipid material layer to smooth and/or thin said lipid material layer;
      (ii) flowing a solution comprising a pore protein adjacent to said lipid material layer to deposit said pore protein in said lipid material layer, and thinning said lipid material layer with an additional bubble in said flow channel;
   (b) bringing said buffer solution in contact with said lipid material layer to facilitate the formation of the lipid bilayer on top of said electrode, the pore protein solution and the buffer solution being separated by the additional bubble;
   (c) measuring a current through said electrode to determine if at least a portion of said lipid material layer has formed said lipid bilayer adjacent to said electrode;

(d) based on the determination of (c), applying a stimulus to said electrode to induce said at least the portion of the material layer to form said lipid bilayer adjacent to said electrode; and (e) applying a stimulus through said electrode to facilitate the insertion of the pore protein in said lipid bilayer.

2. The method of claim 1, wherein, in (c), one or more voltages are applied to said electrode.

3. The method of claim 2, wherein said voltage is selected to break or disrupt the bilayer over the electrode.

4. The method of claim 1, wherein the stimulus is selected from the group consisting of a liquid flow over the surface of the electrode, a sequential flow of one or more different liquids over the surface of the electrode, a flow of one or more bubbles over the surface of the electrode, an electrical pulse, a sonication pulse, a pressure pulse, and a sound pulse.

5. The method of claim 1, wherein the material layer comprising one or more porin proteins and one or more surfactants at a concentration less than the critical micelle concentration of the surfactant.

6. The method of claim 1, wherein said flow channel comprises a plurality of electrodes, wherein said plurality of electrodes comprises said electrode.

7. The method of claim 6, wherein the stimulus is applied simultaneously to said plurality of electrodes.

8. The method of claim 1, wherein the material layer comprises at least two types of lipids.

9. The method of claim 1, wherein the pore protein is selected from the group consisting of *mycobacterium smegmatis* porin A (MspA), alpha-hemolysin, and any protein having at least 70% homology to at least one of *smegmatis* porin A (MspA) or alpha-hemolysin.

10. The method of claim 1, wherein said lipid bilayer and said pore protein together exhibit a resistance of about 1 GΩ or less.

11. The method of claim 1, wherein said lipid bilayer without a pore protein exhibits a resistance greater than about 1 GΩ.

12. The method of claim 1, wherein a pressure of said buffer solution is selected such that said material layer forms said lipid bilayer without said stimulus.

13. The method of claim 1, further comprising, prior to (a), generating said material layer adjacent to said electrode.

14. The method of claim 13, wherein said generating comprises:
directing a lipid solution comprising said one or more lipids through said flow channel; and
depositing said material layer on said electrode.

15. The method of claim 14, wherein said lipid solution comprises an organic solvent.

16. The method of claim 15, wherein said organic solvent comprises decane.

17. The method of claim 1, wherein said buffer solution comprises an ionic solution.

18. The method of claim 17, wherein the ionic solution comprises a chloride anion.

19. The method of claim 18, wherein the ionic solution comprises sodium acetate.

20. The method of claim 1, wherein said bubble is a vapor bubble.

21. The method of claim 1, wherein said one or more lipids are selected from the group consisting of diphytanoyl-phosphatidylcholine (DPhPC), palmitoyl-oleoyl-phosphatidyl-choline (POPC), dioleoyl-phosphatidyl-methylester (DOPME), dipalmitoylphosphatidylcholine (DPPC), phosphatidylcholine, phosphatidylethanolamine, phosphatidylserine, phosphatidic acid, phosphatidylinositol, phosphatidylglycerol and sphingomyelin.

22. The method of claim 1, wherein a surface of said electrode that is exposed to said flow channel is hydrophilic.

23. The method of claim 1, wherein said electrode is disposed adjacent to one or more hydrophobic surfaces of the flow channel.

24. The method of claim 23, wherein said one or more hydrophobic surfaces are silanized.

25. The method of claim 1, wherein said flow channel is formed in a chip.

26. The method of claim 1, wherein said electrode is formed in a surface of said flow channel.

27. The method of claim 1, wherein said flow channel is sealed.

28. The method of claim 1, wherein said one or more flow channels comprise a plurality of flow channels.

29. The method of claim 28, wherein said plurality of flow channels are fluidically separated from one another with the aid of guide rails along said plurality of flow channels.

30. The method of claim 1, wherein said electrode is an individually addressable electrode.

31. The method of claim 1, wherein (c) further comprises determining if at least a portion of said material layer has formed a lipid bilayer over all or a portion of said electrode.

32. A method for forming a lipid bilayer for use in a nanopore sensor, comprising:

(a) providing a chip comprising a plurality of electrodes and lipid material layers adjacent to said plurality of electrodes, wherein each of said lipid material layers comprises a lipid capable of forming the lipid bilayer;
  (i) directing a bubble through said flow channel and bringing said bubble in contact with said lipid material layer to smooth and/or thin said lipid material layer;
  (ii) flowing a solution comprising a pore protein adjacent to said lipid material layer to deposit said pore protein in said lipid material layer, and thinning said lipid material layer with an additional bubble in said flow channel;

(b) contacting said lipid material layers with a buffer solution, wherein said buffer solution is electrically conductive, the pore protein solution and the buffer solution being separated by the additional bubble;

(c) applying a stimulus to at least a subset of said plurality of electrodes to induce said material layers to form lipid bilayers adjacent to the plurality of the electrodes; and (d) repeating steps (b) and (c), as needed, until at least about 20% of said plurality of electrodes deactivate at a voltage pulse between about −100 millivolts (mV) and −1000 mV applied to said plurality of electrodes; and (e) applying a stimulus through at least a subset of said plurality of electrodes to facilitate the insertion of said pore protein in each of said lipid bilayers.

33. The method of claim 32, wherein said plurality of electrodes are each individually addressable.

34. The method of claim 32, wherein steps (b) and (c) are repeated as needed until at least about 60% of said plurality of electrodes deactivate at said applied voltage pulse.

35. The method of claim 32, wherein said applied voltage pulse is between about −400 mV and −700 mV.

36. The method of claim 32, wherein the stimulus selected from the group consisting of a liquid flow over the surface of the electrode, a sequential flow of one or more different liquids over the surface of the electrode, a flow of one or more bubbles over the surface of the electrode, an electrical pulse, a sonication pulse, a pressure pulse, and a sound pulse.

37. The method of claim 32, wherein the pore protein is selected from the group consisting of *mycobacterium smegmatis* porin A (MspA), alpha-hemolysin, and any protein having at least 70% homology to at least one of *smegmatis* porin A (MspA) or alpha-hemolysin.

38. The method of claim 32, wherein (a) further comprises:
   contacting the plurality of electrodes with a lipid solution to form said material layers, wherein said lipid solution comprises said lipid.

39. The method of claim 38, wherein said lipid solution comprises an organic solvent.

40. The method of claim 39, wherein said organic solvent comprises decane.

41. The method of claim 32, wherein said buffer solution comprises an ionic solution.

42. The method of claim 41, wherein the ionic solution comprises a chloride anion.

43. The method of claim 42, wherein the ionic solution comprises sodium acetate.

44. The method of claim 32, wherein said electrodes are sealed in one or more flow channels of said chip.

* * * * *